United States Patent
Maw

(10) Patent No.: US 6,514,975 B1
(45) Date of Patent: *Feb. 4, 2003

(54) ANTI-INFLAMMATORY PIPERAZINYL-BENZYL-TETRAZOLE DERIVATIVES AND INTERMEDIATES THEREOF

(75) Inventor: Graham N. Maw, Sandwich (GB)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,322

(22) PCT Filed: Apr. 17, 1998

(86) PCT No.: PCT/EP98/02277

§ 371 (c)(1),
(2), (4) Date: Aug. 11, 1999

(87) PCT Pub. No.: WO98/52929

PCT Pub. Date: Nov. 26, 1998

(30) Foreign Application Priority Data

May 19, 1997 (GB) ................................ 9709972

(51) Int. Cl.[7] .................. A61K 31/496; C07D 403/10; C07D 417/14
(52) U.S. Cl. .................. 514/252.19; 514/253.09; 514/254.02; 514/254.03; 514/254.05; 544/295; 544/364; 544/366; 544/367; 544/369; 544/371
(58) Field of Search ............... 544/366, 364, 544/367, 369, 295, 371; 514/254.05, 253.09, 254.03, 254.02, 252.19

(56) References Cited

U.S. PATENT DOCUMENTS 3,453,285 A  * 7/1969 Hayao .................. 260/308

FOREIGN PATENT DOCUMENTS

| EP | 676 396 | * 10/1995 |
| WO | 93/15062 | * 8/1993 |
| WO | 95/04051 | * 2/1995 |
| WO | 97/26252 | * 7/1997 |

OTHER PUBLICATIONS

Schiller et al, Medline Abstract for Journal of Receptor & Signal Transduction Research 19, pp. 573–588, 1999.*

Pasternak, Medline Abstract for Clinical Neuropharmacology 16, p 1–8, 1993.*

* cited by examiner

*Primary Examiner*—Emily Bernhardt
(74) *Attorney, Agent, or Firm*—Peter C. Richardson; Gregg C. Benson; Robert T. Ronau

(57) ABSTRACT

This invention relates to tetrazoles and their pharmaceutically acceptable salts which are selective agonists for the delta opioid receptor, particularly useful in the treatment of inflammatory diseases such as arthritis, psoriasis, asthma, inflammatory bowel disease, disorders or respiratory function, gastrointestinal disorders such as functional bowel disease and functional GI disorders, of formula (I)

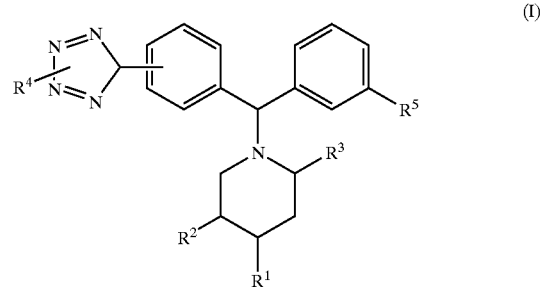

(I)

wherein $R^1$ is H, $C_2$–$C_6$ alkanoyl, $C_1$–$C_6$ alkyl, $C_2$–$C_6$ alkenyl, $C_2$–$C_6$ alkynyl, ($C_3$–$C_7$ cycloalkyl)-($C_1$–$C_4$ alkyl), ($C_1$–$C_4$ alkoxy)-($C_1$–$C_4$ alkyl), carboxy-($C_1$–$C_4$ alkyl), aryl-($C_1$–$C_4$ alkyl) or heteroaryl-($C_1$–$C_4$ alkyl); $R^2$ and $R^3$ are each independently H or $C_1$–$C_4$ alkyl; $R_4$ is selected from (i) H, (ii) a group of the formula $R^6$—$(CH_2)_m$—Z—$(CH_2)_n$—, where m is 0, 1, 2 or 3, n is 1, 2 or 3, Z is a direct link or O, and $R^6$ is —$CO_2H$ or —$CO_2(C_1$–$C_4$ alkyl), and (iii) a group of formula (a)

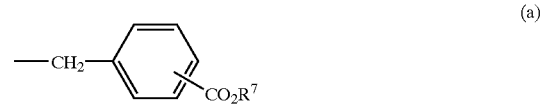

(a)

where $R^7$ is H or $C_1$–$C_4$ alkyl; and $R^5$ is hydroxy, $C_1$–$C_4$ alkoxy or —$NHSO_2(C_1$–$C_4$ alkyl); with the proviso that when Z is O, m is 1, 2 or 3 and n is 2 or 3.

17 Claims, No Drawings

ANTI-INFLAMMATORY PIPERAZINYL-BENZYL-TETRAZOLE DERIVATIVES AND INTERMEDIATES THEREOF

CROSS REFERENCE TO RELATED APPLICATIONS

This application is a 371 of PCT/EP98/02277 filed Apr. 17, 1998 which is a 365 (a–b) of GB 9709972.5 filed May 19, 1997.

This invention relates to tetrazole derivatives which have utility as ligands for opioid receptors.

More particularly, this invention relates to tetrazoles, their preparation and their use as selective agonists for the delta receptor.

At least three subtypes of opioid receptors (mu, delta and kappa) are described and documented in the scientific literature. All three receptors are to be present in the central and peripheral nervous systems of many species including man. Activation of delta receptors is known to produce antinociception in rodents and can induce analgesia in man, in addition to influencing motility of the gastrointestinal tract [see Burks, T. F. (1995) in "The pharmacology of opioid peptides", Tseng L. F. ed. Harwood Academic Publishers].

We have discovered a novel class of tetrazole derivatives which are potent and selective delta opioid agonists which are useful for preventing or treating inflammatory diseases such as arthritis, psoriasis, asthma, or inflammatory bowel disease, disorders of respiratory function, gastrointestinal disorders such as functional bowel disease, functional GI disorders such as irritable bowel syndrome, functional diarrhoea, functional distension, functional pain, non-ulcerogenic dyspepsia or others associated with disorders of motility or secretion, urogenital tract disorders such as incontinence, as analgesics for treating pain including non-somatic pain, or as immunosuppressants to prevent rejection in organ transplant and skin graft. Thus the invention provides compounds of the formula:

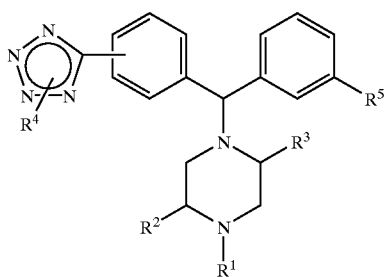

(I)

and their pharmaceutically acceptable salts; wherein $R^1$ is H, $C_2$–$C_6$ alkanoyl, $C_1$–$C_6$ alkyl, $C_2$–$C_6$ alkenyl, $C_2$–$C_6$ alkynyl, $C_3$–$C_7$ cycloalkyl, ($C_3$–$C_7$ cycloalkyl)-($C_1$–$C_4$ alkyl), ($C_1$–$C_4$ alkoxy)-($C_1$–$C_4$ alkyl), carboxy-($C_1$–$C_4$ alkyl), aryl-($C_1$–$C_4$ alkyl) or heteroaryl-($C_1$–$C_4$ alkyl);

$R^2$ and $R^3$ are each independently H or $C_1$–$C_4$ alkyl;

$R^4$ is selected from (i) H, (ii) a group of the formula $R^6$—$(CH_2)_m$—Z—$(CH_2)_n$—, where m is 0, 1, 2 or 3, n is 1, 2 or 3, Z is a direct link or O, and $R^6$ is —$CO_2H$ or —$CO_2(C_1$–$C_4$ alkyl), and (iii) a group of the formula

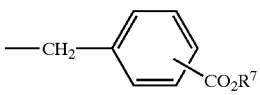

where $R^7$ is H or $C_1$–$C_4$ alkyl;

and $R^5$ is hydroxy, $C_1$–$C_4$ alkoxy or —$NHSO_2(C_1$–$C_4$ alkyl);

with the proviso that when Z is O, m is 1, 2 or 3 and n is 2 or 3.

Where appropriate, the alkyl alkanoyl, alkoxy, alkenyl and alkynyl groups can be straight or branched chain.

Preferred aryl groups are phenyl and naphthyl, both optionally substituted by up to three substituents each independently selected from halo, trifluoromethyl, $C_1$–$C_4$ alkyl and $C_1$–$C_4$ alkoxy.

More preferably, "aryl" is phenyl optionally substituted by one or two substituents as defined above.

"Halo" means F, Cl, Br or I.

Preferred heteroaryl groups include 5- or 6-membered aromatic heterocyclic groups such as thiazolyl, oxazolyl, oxadiazolyl, thiadiazolyl, pyridinyl, pyrimidinyl and pyrazolyl.

Thiazol-2-yl is the most preferred heteroaryl group.

The preferred alkyl groups are methyl and ethyl. The preferred alkoxy groups are methoxy and ethoxy The preferred alkanoyl group is acetyl. The preferred alkenyl group is allyl. The preferred alkynyl group is vinyl. The preferred cycloalkyl group is cyclopropyl.

The tetrazole group is preferably attached to the 3- or 4-position of the adjacent phenyl ring.

$R^1$ is preferably H, allyl, benzyl, $C_1$–$C_4$ alkyl, or ($C_3$–$C_7$ cycloalkyl)methyl; most preferably allyl.

$R^2$ and $R^3$ are preferably each independently H or methyl; more preferably both methyl or both H; most preferably both methyl.

$R^5$ is preferably hydroxy, methoxy or —$NHSO_2Me$; most preferably hydroxy.

$R^4$ is preferably H or a group of the formula (a) —$(CH_2)_pCO_2H$ or —$(CH_2)_pCO_2$ ($C_1$–$C_4$ alkyl) where p is 1, 2, 3 or 4, (b) —$(CH_2)_2$—O—$CH_2CO_2H$, (c) —$(CH_2)_2$—O—$CH_2CO_2(C_1$–$C_4$ alkyl) or (d),

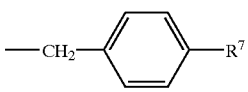

where $R^7$ is H or $C_1$–$C_4$ alkyl.

In $R^4$, the preferred alkyl group is ethyl.

Preferred individual compounds are those of Examples 1, 4, 24, 27, 36, 42, 94, 96, 104 and 107.

The preferred stereo chemistry of the compounds of the formula (i) is as follows:

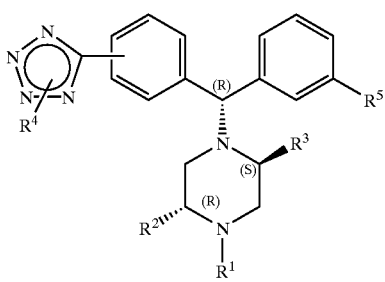
(IA)

Such compounds are most readily prepared by using starting materials with the appropriate stereochemistry.

The compounds of the formula (I) can be prepared by conventional routes such as those set out in the following Examples and Preparations and in WO-A-9315062.

Route A

Compounds of the formula (I) in which $R^5$ is hydroxy can be prepared by the reaction of the corresponding methoxy compounds of the formula (I) with boron tribromide. Preferably boron tribromide in dichloromethane is added to a solution of the methoxy starting material in dichloromethane and the mixture is stirred at room temperature for a few hours. The product can then be isolated and purified by conventional techniques.

Removal of a hydroxy-protecting group from the corresponding hydroxy-protected compound is also possible, typified by the conversion of t-butyldimethylsilyloxy to hydroxy using tetraethylammnonium fluoride.

Route B

The compounds (I) in which $R^4$ is H, can be prepared by the reaction of a corresponding nitrile of the formula:

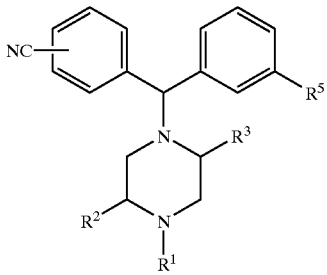
(II)

where $R^1$, $R^2$, $R^3$ and $R^5$ are as defined for formula (I), with dibutyltin oxide and trimethylsilyl azide.

The reaction is typically carried out in a suitable organic solvent such as dry toluene at from about 50° C. to the reflux temperature. If necessary, a hydroxy group represented by $R^5$ can be protected prior to reaction, e.g. by a t-butyldimethylsilyl protecting group, and the protecting group can be removed subsequently by a conventional technique.

Route C

Compounds (I) in which $R^4$ is either (i) $R^6$—$(CH_2)_m$—Z—$(CH_2)_n$— where $R^6$ is —$CO_2(C_1$–$C_4$ alkyl) and Z, m and n are as defined for formula (I) or (ii)

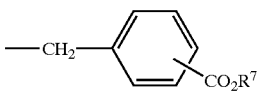

where $R^7$ is $C_1$–$C_4$ alkyl can be prepared by the alkylation of the corresponding compounds in which $R^4$ is H with an alkylating agent of the formula, respectively, $$R^6—(CH_2)_m—Z—(CH_2)_n—Q^1 \quad \text{(IIIA)}$$

or

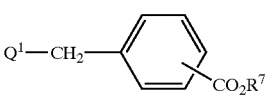
(IIIB)

where Z, m and n are as defined for formula (I), $R^6$ and $R^7$ are defined in this method and $Q^1$ is a leaving group, preferably Br.

The reaction is typically carried out in the presence of a base such as potassium or cesium carbonate in a suitable organic solvent, e.g. acetonitrile, under gentle reflux.

This reaction generally produces a mixture of compounds in which the group $R^4$ is attached to the 1- and 2- positions of the tetrazole ring.

When a compound in which $R^5$ is hydroxy is required, it may be necessary to protect the hydroxy group before reaction, such as by a t-butyldimethylsilyl group, which can be removed conventionally after reaction, e.g. by the use of tetraethylammonium fluoride.

In an alternative alkylation procedure, the corresponding compound in which $R^4$ is H is reacted firstly with a strong base such as sodium ethoxide (prepared by adding sodium metal to ethanol) and then with the compound III, no additional base being necessary.

Route D

Compounds (I) in which $R^6$ is —$CO_2H$ can also be prepared by the hydrolysis, preferably alkaline hydrolysis, of the corresponding esters in which $R^6$ is $C_1$–$C_4$ alkyl.

The reaction is typically carried out with aqueous sodium hydroxide in methanol or a mixture of dioxane and methanol at room temperature.

Route E

Compounds (I) in which $R^6$ is —$CO_2H$ can also be prepared by the hydrolysis of the corresponding compounds in which $R^4$ is NC—$(CH_2)_m$—Z—$(CH_2)_n$— where Z, m and n are as defined for formula (I). Acidic hydrolysis using hydrogen chloride gas in ethanol is preferred.

Route F

Compounds (I) in which $R^4$ is 1-[$CH_2CO_2(C_1$–$C_4$ alkyl)] and $R^5$ is —OH can be prepared by ring closure by the reaction of a compound of the formula:

(IV)

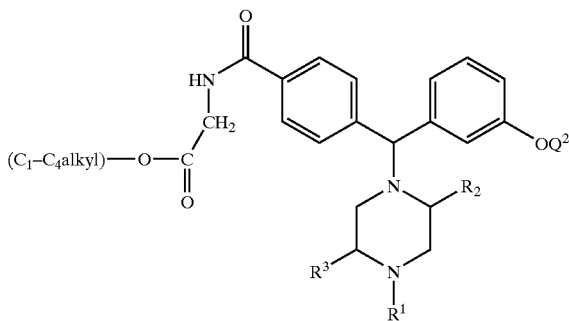

where $R^1$, $R^2$ and $R^3$ are as defined for formula (I) and $Q^2$ is a hydroxy-protecting group such as t-butyldimethylsilyl, with diethyl acidodicarboxylate, triphenyl phosphine and trimethylsilyl azide in a suitable organic solvent such as toluene. Generally the protecting group $Q^2$ is removed under the reaction conditions.

Route G

Compounds (I) can be prepared by reaction of an aldehyde of the formula:

(V)

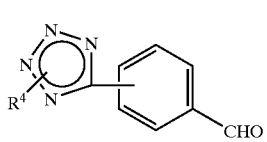

where $R^4$ is as defined for formula (I), with a compound of the formula:

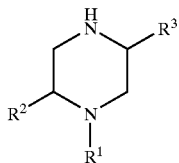

where $R^1$, $R^2$ and $R^3$ are as defined for formula (I), in the presence of benzotriazole, typically under reflux in an organic solvent such as toluene with azeotropic removal of water, following by cooling, e.g. to $-20°$ C., and reaction with a Grignard reagent of the formula:

(VI)

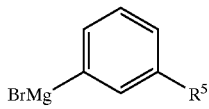

where $R^5$ is $-OQ^2$ where $Q^2$ is a hydroxy-protecting group such as trimethylsilyl.

Any hydroxy-protecting groups which are present are generally removed by the reaction conditions, or can be subsequently removed by a conventional technique.

Route H

Compounds in which $R^1$ is H can be prepared by reaction of the corresponding compound in which $R^1$ is allyl with tris(triphenylphosphine)rhodium(I) chloride, typically under gentle reflux in a solvent system such as aqueous acetonitrile.

Route I

Compounds of the formula (I) in which $R^4$ is $R^6$—$(CH_2)_m$—Z—$(CH_2)_n$— attached to the 1-position of the tetrazole ring and Z,m,n,$R^1$,$R^2$,$R^3$,$R^5$ and $R^6$ are as defined for formula (I) can be prepared as follows:

(VII)

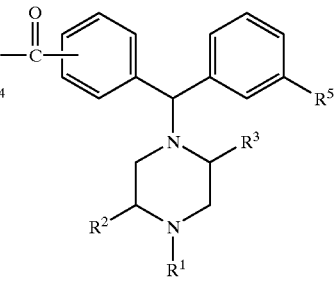

1. $PCl_5$ toluene
2. Trimethylsilyl azide

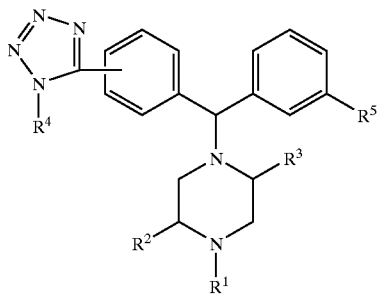

Route J

Compounds of the formula (I) in which $R^5$ is $-NHSO_2$ ($C_1$–$C_4$ alkyl) can be prepared by the reaction of the corresponding amino-substituted compound with a $C_1$–$C_4$ alkanesulphonyl chloride, typically in the presence of an acid-acceptor.

Route K

Compounds of the formula (I) in which $R^1$ is $C_2$–$C_6$ alkyl, aryl-$C_1$–$C_4$ alkyl) or heteroaryl-($C_1$–$C_4$ alkyl) can be prepared by the reductive alkylation of the corresponding compounds in which $R^1$ is H using the appropriate aldehyde ($C_1$–$C_5$ alkyl)CHO, aryl CHO or heteroaryl CHO and a reducing agent such as sodium triacetoxyborohydride.

The invention also includes any novel intermediates described herein, particularly those of the formula (II).

The necessary intermediates for the processes described above can be prepared by conventional methods such as those set out in the following Preparations, e.g. as follows:

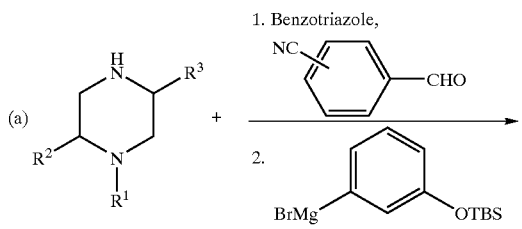

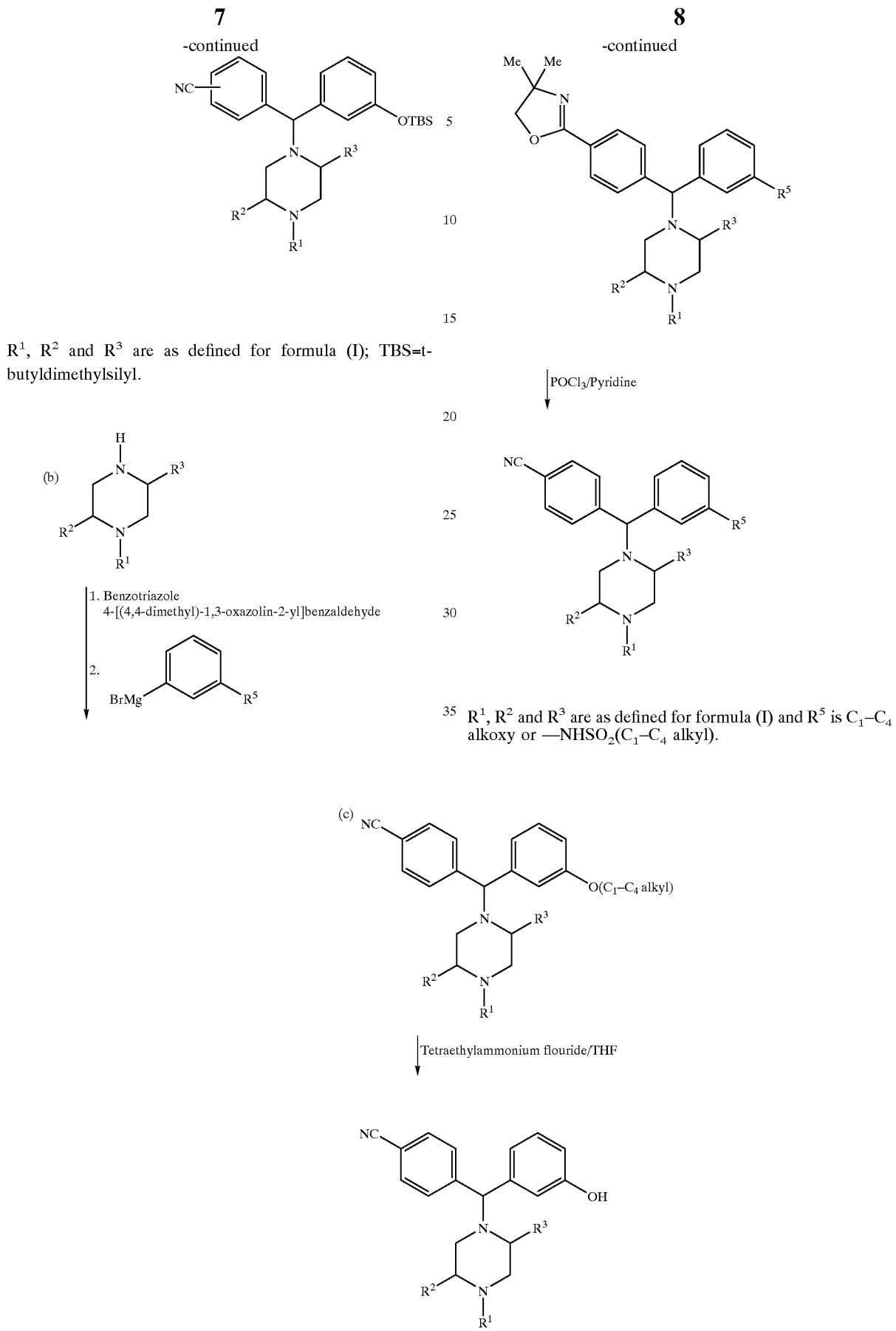
$R^1$, $R^2$ and $R^3$ are as defined for formula (I); TBS=t-butyldimethylsilyl.
$R^1$, $R^2$ and $R^3$ are as defined for formula (I) and $R^5$ is $C_1$–$C_4$ alkoxy or —$NHSO_2(C_1$–$C_4$ alkyl).

-continued
(d) 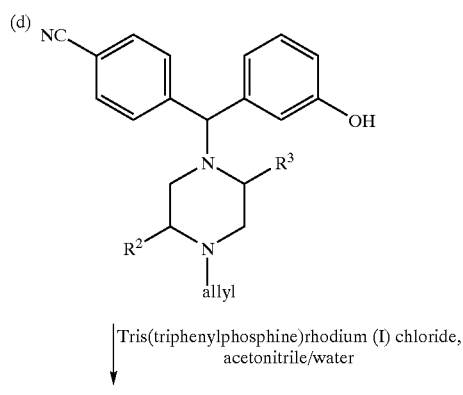
|
Tris(triphenylphosphine)rhodium (I) chloride,
acetonitrile/water
↓
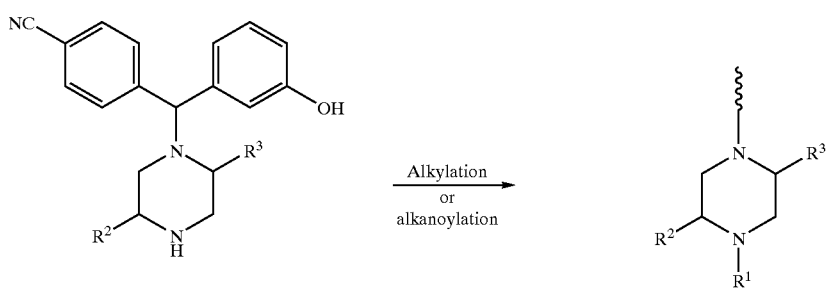
Alkylation
or
alkanoylation
→
(e) 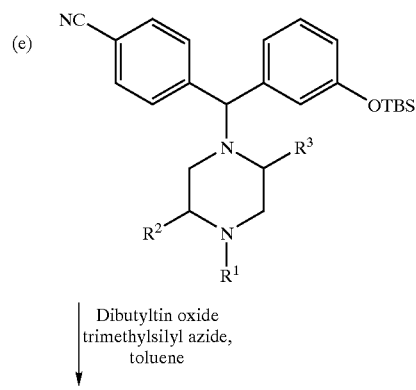
|
Dibutyltin oxide
trimethylsilyl azide,
toluene
↓
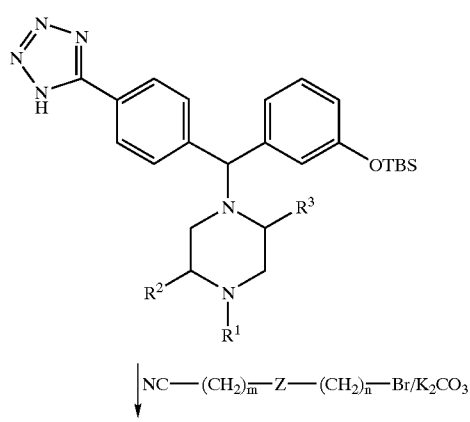
|
NC—(CH$_2$)$_{\overline{m}}$—Z—(CH$_2$)$_{\overline{n}}$—Br/K$_2$CO$_3$
↓

-continued
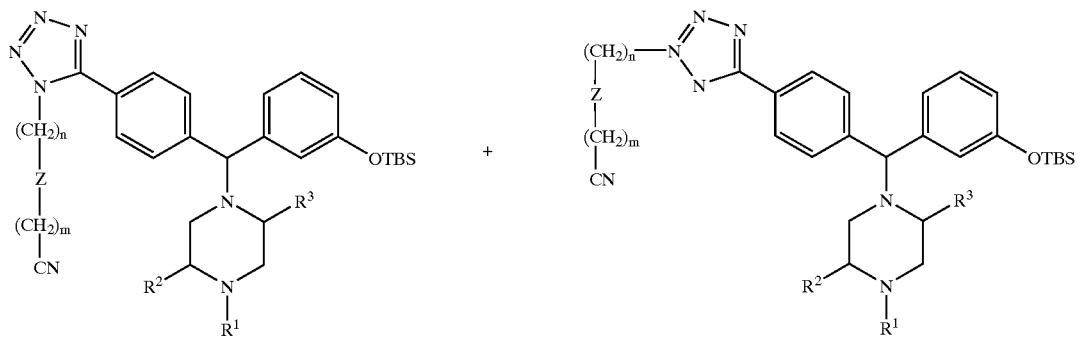
(f)
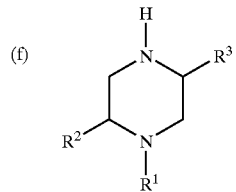
1. Benzotriazole, (C$_1$–C$_4$ alkoxy).
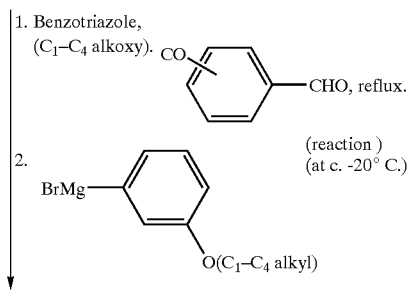
CHO, reflux.
(reaction) (at c. −20° C.)
2.
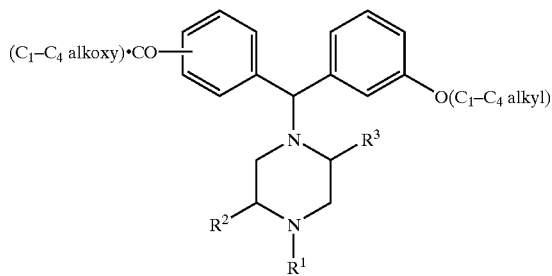
↓ Hydrolysis (e.g. aqueous NaOH)
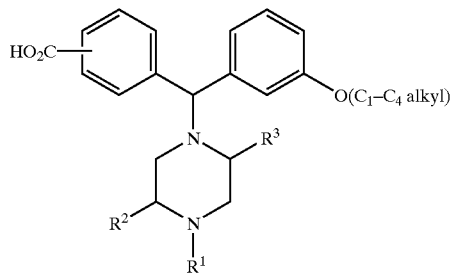
1. 1-Hydroxybenzotriazole, diisopropylethylamine, 1-(3-dimethylaminopropyl)-3-ethylcarbodiimide hydrochloride
2. R$^6$—(CH$_2$)$_{\overline{m}}$—Z—(CH$_2$)$_n$NH$_2$·HCl[R$^6$ = —CO$_2$(C$_1$–C$_4$ alkyl].
↓

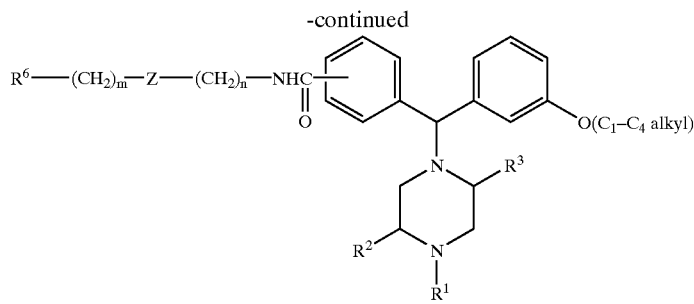

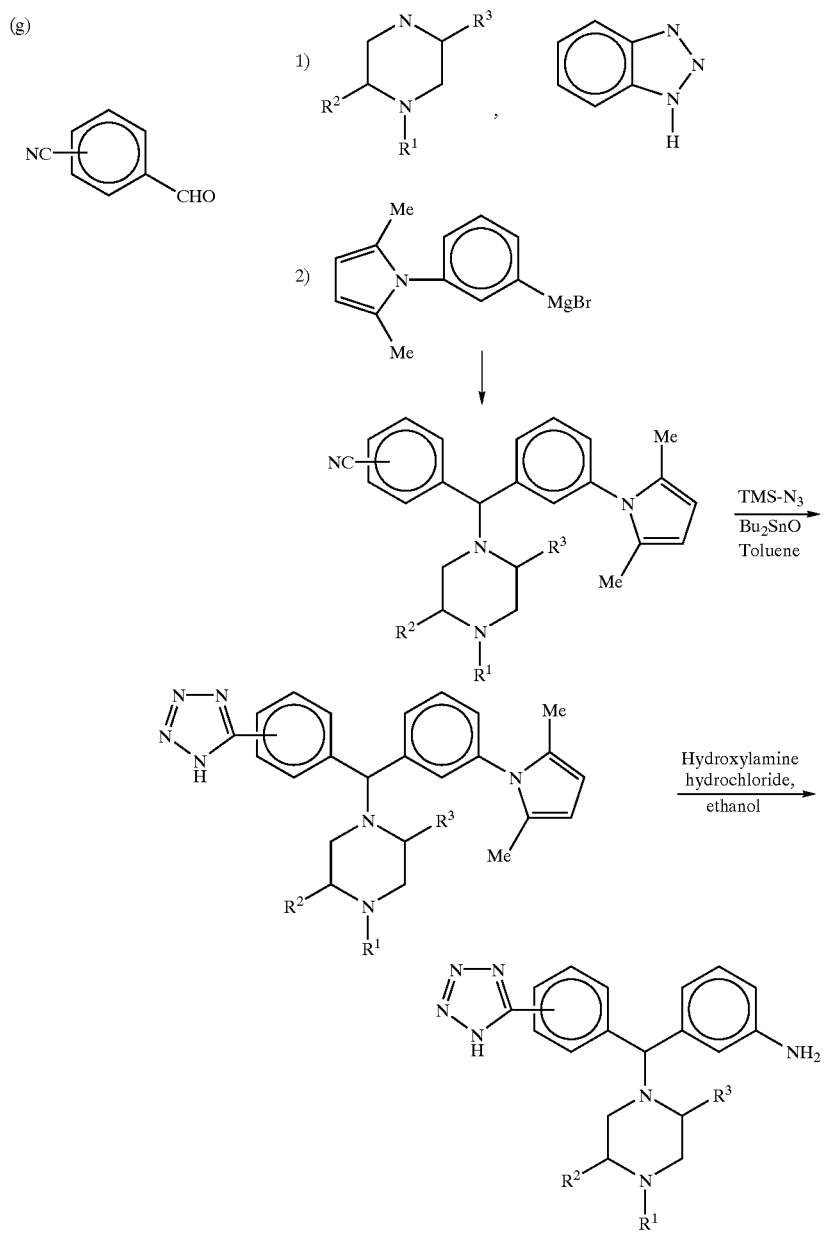

Suitable pharmaceutically acceptable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable pharmaceutically acceptable base salts are formed from bases which form non-toxic salts and examples are the calcium, lithium, magnesium, potassium, sodium, zinc, ethanolamine, diethanolamine and triethanolamine salts.

For a review on suitable salts see Berge et al, J.Pharm.Sci., 66 1–19 (1977).

As will already be apparent the compounds of the formula (I) will contain one or more asymmetric carbon atoms and will therefore exist in two or more stereoisomeric forms, or they may exist as tautomers. The present invention includes the individual stereoisomers and tautomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

Receptor Binding Assays

Opioid (mu and kappa) receptor binding assays were performed in guinea-pig brain membrane preparations. Binding assays were carried out at 25° C. for 60 minutes in 50 mM Tris (pH 7.4) buffer. [$^3$H]-DAMGO (2 nM) and [$^3$H]-U-69,593 (2 nM) were used to label mu and kappa receptor binding sites respectively. The protein concentration was approximately 200 μg/well. Non-specific binding was defined with 10 μM naloxone.

Delta receptor binding assay was performed in a stable line of CHO cells expressing the human delta receptor. The binding assay was carried out at 25° C. for 120 minutes in 50 mM Tris (pH 7.4) buffer. [$^3$H]-SNC-80 was used to label delta receptor binding sites. The protein concentration was approximately 12.5 μg/well. Non-specific binding was defined with 10 μM naltrexone.

The binding reaction was terminated by rapid filtration through glass fiber filters, and the samples washed with ice-cold 50 mM Tris buffer (pH 7.4). All assays were performed in duplicate/triplicate.

Isolated Tissue Studies

Opioid (delta, mu and kappa) activity was studied in two isolated tissues, the mouse vas deferens (MVD)(δ) and the guinea-pig myentric plexus with attached longitudinal muscle (GPMP)(μ and κ).

MVD (DC1 strain, Charles River, 25–35 g) were suspended in 15 ml organ baths containing Mg$^{++}$-free Krebs' buffer of the following composition (mM): NaCl, 119; KCl, 4.7; NaHCO$_3$, 25; KH$_2$PO$_4$, 1.2; CaCl$_2$, 2,5 and glucose, 11. The buffer was gassed with 95% O$_2$ and 5% CO$_2$. The tissues were suspended between platinum electrodes, attached to an isometric transducer with 500 mg tension and stimulated with 0.03 Hz pulses of 1-msec pulse-width at supramaxinal voltage. IC$_{50}$ values were determined by the regression analysis of concentration-response curves for inhibition of electrically-induced contractions in the presence of 300 nM of the mu-selective antagonist CTOP. This test is a measure of δ agonism.

Guinea-pig (Porcellus strain, male, 450–500 g, Dunkin Hartley) myentric plexus with attached longitudinal muscle segments were suspended with 1 g of tension in Krebs' buffer and stimulated with 0.1 Hz pulses of 1-msec pulse-width at supramaximal voltage. Mu functional activity was determined in the presence of 10 nM nor-BNI with 1 μM of the mu selective agonist, DAMGO, added to the bath at the end of the experiment to define a maximal response. This test is a measure of mu functional agonism.

Kappa functional activity was determined in the presence of and 1 μM CTOP with 1 μM of the kappa selective agonist U-69,593 added at the end of the experiment to define a maximal response. All inhibitions of twitch height for test compounds were expressed as a percentage of the inhibition obtained with the standard agonist and the corresponding IC$_{50}$ value determined.

DAMGO is [D-Ala2,N-MePhe4,Gly5-ol]enkephalin)

U69593 is ((5a, 7a, 8b)-(+)-N-methyl-N-(7-[1-pyrrolidinyl]-1-oxaspiro[4,5]dec-8-yl)-benzeneacetamide)

SNC-80 is (+)-4-[(αR)-α((2S,5R)-4-allyl-2,5-dimethyl-1-piperazinyl)-3-methoxybenzyl]-N,N-diethylbenzamide norBNI is nor-binaltorphimine CTOP is 1,2-Dithia-5,8,11,14,17-pentaazacycloeicosane, cyclic peptide derivative DPDPE is [D-Pen2,D-Pen5]enkephalin)

[3H]-DAMGO, [3H]-U69593, norBNI, and CTOP are all commercially available from DuPont, Amersham International, RBI and DuPont respectively. [3H]-SNC80 was prepared by Amersham International.

In general, a therapeutically effective daily oral or intravenous dose of the compounds of formula (I) and their salts is likely to range from 0.01 to 50 mg/kg body weight of the subject to be treated, preferably 0.1 to 20 mg/kg. The compounds of the formula (I) and their salts may also be administered by intravenous infusion, at a dose which is likely to range from 0.001–10 mg/kg/hr.

Tablets or capsules of the compounds may be administered singly or two or more at a time, as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

The following Examples illustrate the preparation of the compounds (I) and the Preparations illustrate the preparation of novel starting materials.

EXAMPLE 1

(+)-5-{4-[(R)-α-(2(S),5(R)-4-Allyl-2,5-dimethyl-1-piperazinyl)-3-hydroxybenzyl]phenyl}-1H-tetrazole

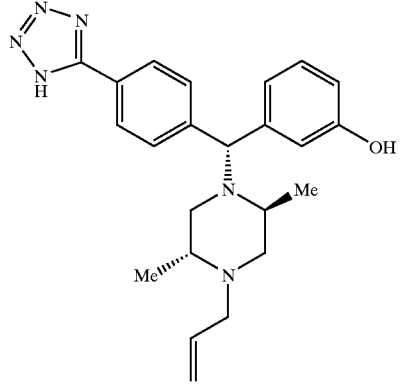

Boron tribromide (1M solution in dichloromethane; 10 ml) was added to a solution of the compound from Example 52 (1 g) in dry dichloromethane (20 ml) and the resulting solution/suspension was stirred at room temperature for 5 hours. The solvent was evaporated in vacuo and the residue basified with methanolic ammonium hydroxide solution and evaporated once again. The residue was purified by column chromatography over silica gel using gradient elution (dichloromethane/methanol/anmonium hydroxide; 93/7/1 to 80/20/3) to afford a foam. This material was further purified over a polystyrene reverse phase resin using gradient elution (100% water/0% acetonitrile to 0% water/100% acetonitrile). The acetonitrile was evaporated in vacuo and the remaining aqueous solution was frozen and lyophilised to afford the title compound as a fine white powder, 762 mg.

$\delta_H$ (300 MHz, $d_6$-DMSO): 9.27 (1H, br s), 7.93 (2H, d), 7.52 (2H, d), 7.13 (1H, t), 6.80–6.60 (3H, m), 5.82 (1H, m), 5.30–5.15 (2H, m), 5.04 (1H, s), 3.37 (1H dd), 3.10 (1H, dd), 2.92 (1H, m), 2.82 (1H, m), 2.70 (1H, m), 2.66 (1H, m), 2.36 (1H, m), 1.97 (1H, dd), 1.10 (3H, d), 1.02 (3H, d). m/z: 405 (HM+). Found: C, 63.82; H, 7.04; N, 20.09. $C_{23}H_{28}N_6O$. 0.1NH$_4$Br requires C, 63.90; H, 7.09; 19.76%. $[\alpha]_D$+13.4° c=0.112, methanol.

EXAMPLE 2

(+)-5-{4-[(R)-α-(2(S),5(R)-4-Ethyl-2,5-dimethyl-1-piperazinyl)-3-hydroxybenzyl]phenyl}-1H-tetrazole

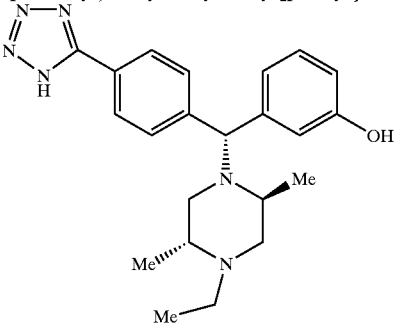

A solution of the compound of Preparation 8 (241 mg), dibutyltin oxide (102 mg) and trimethylsilyl azide (619 mg) in dry toluene (10 ml) were heated together under a gentle reflux for 18 hours. The reaction mixture was evaporated to dryness in vacuo and the residue purified by column chromatography over silica gel (80/22/3 dichloromethane/methanol/ammonia) to afford the title compound after trituration with ethyl acetate, 193 mg.

m/z: 393 (MH+). $R_f$: 0.22 (80/20/3 dichloromethane/methanol/ammonia). Found: C, 64.99; H, 7.31; N, 19.89. $C_{22}H_{28}N_6O$. 3/5$H_2O$. 1/6EtOAc requires C, 65.12; H, 7.36; N, 20.09%. $[\alpha]_D$+10.8° (c 0.12, methanol).

EXAMPLES 3 TO 12

The following compounds of the general formula:

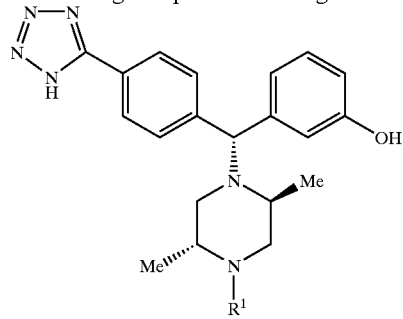

or salts thereof, were prepared from the corresponding nitriles (see Preparations 9 to 13, 16, and 21 to 24) by similar methods to that used in Example 2.

| Ex | R¹ | m/z | $R_f$(a) | $[\alpha]_D$ (b) | Micro Analysis |
|----|----|----|----|----|----|
| 3 | Pr | 407 | 0.25 | +9 c 0.1 | Found: C, 65.61; H, 7.69; N, 19.42. $C_{23}H_{30}N_6O$.3/5$H_2O$.1/5EtOAc requires C, 65.72; H, 7.60; N, 19.32% |
| 4 | Benzyl | 455 | 0.18 | −23 | Found: C, 68.70; H, 6.73; N, 17.68. $C_{27}H_{30}N_6O$.$H_2O$ requires C, 68.62; H, 6.83; N, 17.78% |
| 5 | Thiazol-2-yl.CH$_2$— | 362 | 0.30 | −34 | Found: C, 59.01; H, 6.15; N, 20.11. $C_{24}H_{27}N_7OS$.3/2$H_2O$ requires C, 59.00; H, 6.19; N, 20.01% |
| 6 | Me | 379 | 0.24 | +43 | Found: C, 63.84; H, 6.99; N, 21.68. $C_{21}H_{26}N_6O$.9/10$H_2O$ requires C, 63.91; H, 7.10; N, 21.29% |
| 7 | —CH$_2$CO$_2$H | 423 | 0.04 | +5 | Found: C, 58.86; H, 6.58; N, 20.41. $C_{22}H_{26}N_6O_3$.$H_2O$.1/3NH$_3$ requires C, 58.85; H, 6.62; N, 20.28% |
| 8 | —COMe | 407 | 0.29 | −60 | Found: C, 60.77; H, 6.81; N, 21.86. $C_{22}H_{26}N_6O_2$.$H_2O$.4/5NH$_4$OH requires C, 60.78; H, 7.00; N, 21.91% |
| 9 | Cyclopropyl.CH$_2$— | 419 | 0.32 | −7 | Found: C, 65.79; H, 7.19; N, 19.49. $C_{24}H_{30}N_6O$.$H_2O$ requires C, 66.03; H, 7.39; N, 19.25% |

-continued

| Ex | R¹ | m/z | $R_f$(a) | $[\alpha]_D$ (b) | Micro Analysis |
|---|---|---|---|---|---|
| 10 | 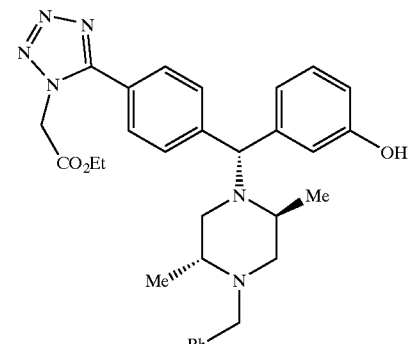 | 473 | 0.42 | −1° * | Found: C, 66.36; H, 6.24; N, 17.56. $C_{27}H_{29}FN_6O \cdot H_2O$ requires C, 66.59; H, 6.33; N, 17.26% |
| 11 | 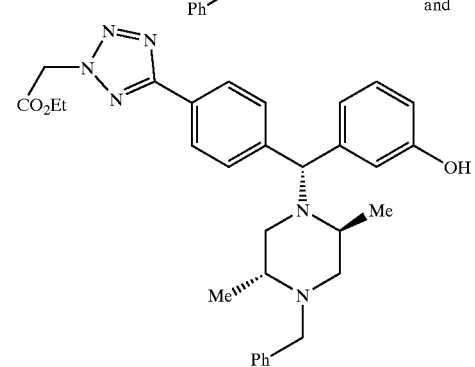 | 485 | 0.43 | −4° ** | Found: C, 66.75; H, 6.70; N, 16.82. $C_{28}H_{32}N_6O_2 \cdot H_2O$ requires C, 66.91; H, 6.82; N, 16.72% |
| 12 | 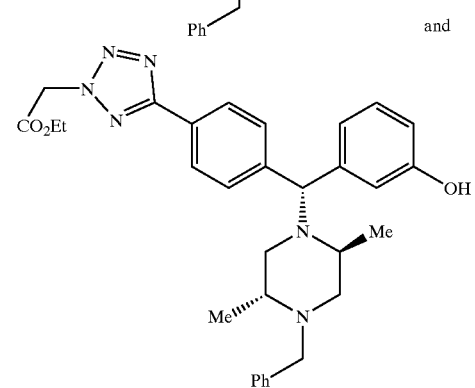 | 523 | 0.44 | 0° *** | Found: C, 62.29; H, 5.73; N, 16.38. $C_{28}H_{29}F_3N_6O \cdot 1/3NH_3 \cdot 2/3H_2O$ requires C, 62.25; H, 5.85; N, 16.41% |

Notes:
(a) solvent system 80/20/3 dichloromethane/methanol/ammonia;
(b) c = 0.1, methanol;
(c) $[\alpha]_{365} -45°$
*(c0.1, methanol);
**(d) $[\alpha]_{436} -28°$ (c0.1, methanol);
***(e) $[\alpha]_{365} -34°$
(c0.1, methanol);

Example 3. (+)-5-{4-[(R)-α-(2(S),5(R)-4-propyl-2,5-dimethyl-1-piperazinyl)-3-hydroxybenzyl]phenyl}-1H-tetrazole Example 4. (−)-5-{4-[(R)-α-(2(S),5(R)-4-benzyl-2,5-dimethyl-1-piperazinyl)-3-hydroxybenzyl]phenyl}-1H-tetrazole Example 5. (−)-5-{4-[(R)-α-(2(S),5(R)-4-thiazol-2-ylmethyl-2,5-dimethyl-1-piperazinyl)-3-hydroxybenzyl]phenyl}-1H-tetrazole Example 6. (+)-5-{4-[(R)-α-(2(S),5(R)-4-methyl-2,5-dimethyl-1-piperazinyl)-3-hydroxybenzyl]phenyl}-1H-tetrazole Example 7. (+)-5-{4-[(R)-α-(2(S),5(R)-4-carboxymethyl-2,5-dimethyl-1-piperazinyl)-3-hydroxybenzyl]phenyl}-1H-tetrazole Example 8. (−)-5-{4-[(R)-α-(2(S),5(R)-4-acetyl-2,5-dimethyl-1-piperazinyl)-3-hydroxybenzyl]phenyl}-1H-tetrazole Example 9. (−)-5-{4-[(R)-α-(2(S),5(R)-4-cyclopropylmethyl-2,5-dimethyl-1-piperazinyl)-3-hydroxybenzyl]phenyl}-1H-tetrazole Example 10. (−)-5-{4-[(R)-α-(2(S),5(R)-4-(4-fluorobenzyl)-2,5-dimethyl-1-piperazinyl)-3-hydroxybenzyl]phenyl}-1H-tetrazole Example 11. (−)-5-{4-[(R)-α-(2(S),5(R)-4-(4-methoxybenzyl)-2,5-dimethyl-1-piperazinyl)-3-hydroxybenzyl]phenyl}-1H-tetrazole Example 12. 5-{4-[(R)-α-(2(S),5(R)-4-(4-trifluromethylbenzyl)-2,5-dimethyl-1-piperazinyl)-3-hydroxybenzyl]phenyl}-1H-tetrazole

EXAMPLES 13 AND 14

Ethyl (5-{4-[(R)-α-(2(S),5(R)-4-Benzyl-2,5-dimethyl-1-piperazinyl)-3-hydroxybenzyl]phenyl}-2-tetrazolyl)acetate Ethyl (5-{4-[(R)-α-(2(S),5(R)-4-Benzyl-2,5-dimethyl-1-piperazinyl)-3-hydroxybenzyl]phenyl}-1-tetrazolyl)acetate

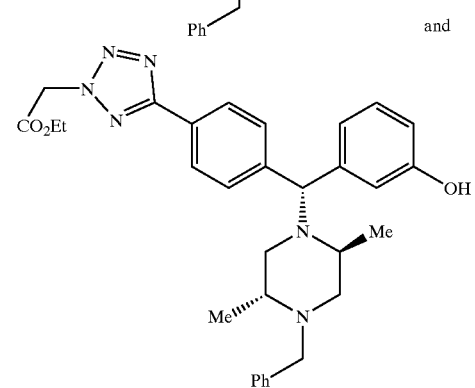

and

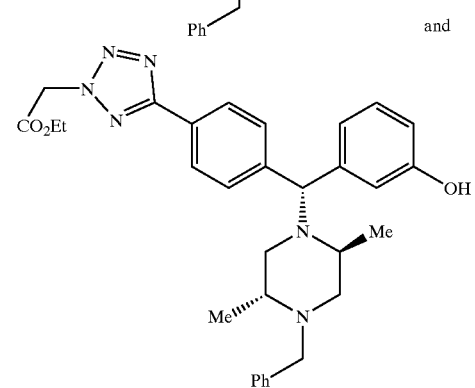

A solution of the compound of Preparation 28 (1.704 g), ethyl bromoacetate (501 mg)) and potassium carbonate (1.38 g) in acetonitrile (40 ml)) was heated under a gentle reflux for 2 hours. The cooled reaction mixture was partitioned between water and ethyl acetate. The aqueous layer was separated and extracted with further ethyl acetate. The combined organic extracts were washed with water, saturated brine solution, dried (Na2SO4) and evaporated to dryness in vacuo. The residue was dissolved in tetrahydrofuran (20 ml) and tetraethylammonium fluoride (1.11 g) in water (2 ml) added. The mixture was stirred at room temperature for 18 hours then partitioned between ethyl acetate and water. The layers were separated and the organic phase was washed with water and saturated brine solution, dried (MgSO4) and evaporated to dryness in vacuo. The residue was purified by column chromatography over silica gel (100% hexane to 40% ethyl acetate/hexane) to afford the N-2 isomer, 1.20 g, followed by the N-1 isomer, 248 mg,.

N-2 Isomer: (Example 13). m/z: 541 (MH+). Rf: 0.33 (1/1 hexane/ethyl acetate).

N-1 Isomer: (Example 14). m/z: 541 (MH+). Rf: 0.26 (1/1 hexane/ethyl acetate).

Example 13: $\delta_H$ (300 Mhz, CDCl$_3$): 7.60 (2H, d), 7.48 (2H, d), 7.34–7.16 (6H, m), 6.80–6.62 (3H, m), 5.18 (2H, s), 5.12 (1H, s), 4.24 (2H, q), 3.92 (1H, d), 3.20 (1H, d), 2.80–2.56 (4H, m), 2.04 (2H, m), 1.24 (3H, q), 1.10 (6H, m).

Example 14 $\delta_H$ (300 Mhz, CDCl$_3$): 8.18 (2H, d), 7.56 (2H, d), 7.36–7.12 (6H, m), 6.82–6.64 (3H, m), 5.42 (2H, s), 5.20 (1H, br s), 5.10 (1H, s), 4.28 (2H, q), 3.92 (1H, d), 3.20 (1H, d), 2.78–2.56 (4H, m), 2.02 (2H, m), 1.28 (3H, q), 1.10 (6H, m).

EXAMPLES 15 TO 18

The following compounds of the general formula:

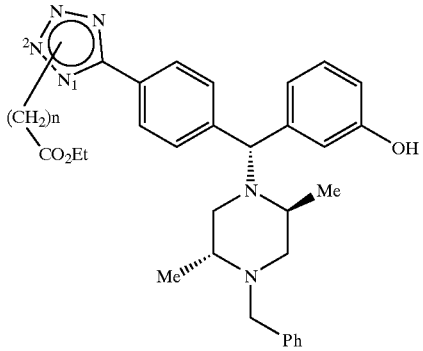

were prepared by alkylation of the compound of Preparation 28 with a ethyl 4-bromobutyrate or ethyl 5-bromovalerate as appropriate by similar methods to that used in Example 13/14.

| Ex | Isomer | n | m/z | Rf 1/1 hexane/ethyl acetate |
|---|---|---|---|---|
| 15 | N-1 | 3 | 569 | 0.29 |
| 16 | N-2 | 3 | 569 | 0.42 |
| 17 | N-1 | 4 | 583 | 0.40 |
| 18 | N-2 | 4 | 583 | 0.53 |

Example 15. Ethyl 4-(5-{4-[(R)-α-(2(S),5(R)-4-benzyl-2,5-dimethyl-1-piperazinyl)-3-hydroxybenzyl]phenyl}-1-tetrazolyl)butyrate.

Example 16. Ethyl 4-(5-{4-[(R)-α-(2(S),5(R)-4-benzyl-2,5-dimethyl-1-piperazinyl)-3-hydroxybenzyl]phenyl}-2-tetrazolyl)butyrate Example 17. Ethyl 5-(5-{4-[(R)-α-(2(S),5(R)-4-benzyl-2,5-dimethyl-1-piperazinyl-3-hydroxybenzyl]phenyl}-1-tetrazolyl)valerate Example 18. Ethyl 5-(5-{4-[(R)-α-(2(S),5(R)-4-benzyl-2,5-dimethyl-1-piperazinyl)-3-hydroxybenzyl]phenyl}-2-tetrazolyl)valerate Example 15 $\delta_H$ (300 Mhz, CDCl$_3$): 7.60 (4H, m), 7.36–7.16 (6H, m), 6.80–6.70 (2H, m), 6.62 (1H, m), 5.28 (1H, s), 5.16 (1H, s), 4.52(2H, t), 4.06 (2H, q), 3.96 (1H, d), 3.20 (1H, d), 2.80–2.56 (4H, m), 2.40 (2H, m), 2.24 (2H, m), 2.00 (2H, m), 1.22(3H, t), 1.10 (6H, m).

Example 16 $\delta_H$ (300 Mhz, CDCl$_3$): 8.02 (2H, d), 7.48 (2H, d), 7.36–7.10 (6H, m), 6.78 (1H, d), 6.70 (1H, d), 6.64 (1H, s), 5.40 (1H, br s), 5.10 (1H, s), 4.72 (2H, m), 4.16 (2H, m), 3.96 (1H, d), 3.20 (1H, d), 2.80–2.56 (4H, m), 2.40 (4H, m), 2.02 (2H, m), 1.24 (3H, t), 1.10 (3H, d), 1.08 (3H, d).

Example 17 $\delta_H$ (300 Mhz, CDCl$_3$): 8.02 (2H, d), 7.56 (2H, d), 7.36–7.16 (6H, m), 6.80 (1H, d), 6.70 (2H, m), 5.18 (1H, br s), 5.18 (1H, s), 5.10 (1H, s), 4.64 (2H, t), 4.16 (2H, q), 3.92 (1H, d), 3.20 (1H, d), 2.78–2.54 (4H, m), 2.38 (2H, t), 2.18–1.98 (4H, m), 1.72 (2H, m), 1.24 (3H, t), 1.08 (6H, m).

Example 18 $\delta_H$ (300 Mhz, CDCl$_3$): 7.64 (2H, d), 7.58 (2H, d), 7.36–7.18 (6H, m), 6.78 (2H, m), 6.60 (1H, s), 5.20 (1H, s), 4.42 (2H, t), 4.10 (2H, t), 3.96 (1H, d), 3.20 (1H, d), 2.80–2.56 (4H, m), 2.28 (2H, t), 2.00 (3H, m), 1.60 (4H, m), 1.22 (3H, t), 1.10 (6H, m).

EXAMPLE 19

(+)-5-{4-[(R-α-(2(S),5(R)-4-Benzyl-2,5-dimethyl-1-piperazinyl)-3-hydroxybenzyl]phenyl}-2-tetrazolyl) acetic Acid

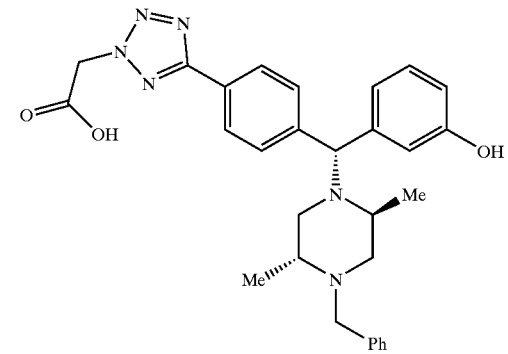

Aqueous sodium hydroxide (2 N, 3 ml) was added to a solution of the compound of Example 13 (1.15 g) in methanol (30 ml) and the mixture stirred at room temperature for 18 hours. The reaction was quenched with 2 N hydrochloric acid (3 ml) and then evaporated to dryness in vacuo. The residue was purified by column chromatography over silica gel (80/20/3 dichloromethane/methanol/ammonium hydroxide) to afford the title compound, 977 mg.

m/z: 513 (MH+). Rf: 0.45 (80/20/3 dichloromethane/methanol/ammonium hydroxide). $[\alpha]_D$+6.2° (c 0.1, methanol). Found: C, 65.37; H, 6.49; N, 16.61. $C_{29}H_{32}N_6O_3 \cdot 2/3H2O \cdot 1/3NH3$ requires C, 65.68; H, 6.53, N, 16.72%.

EXAMPLES 20 TO 24

The following compounds of the general formula:

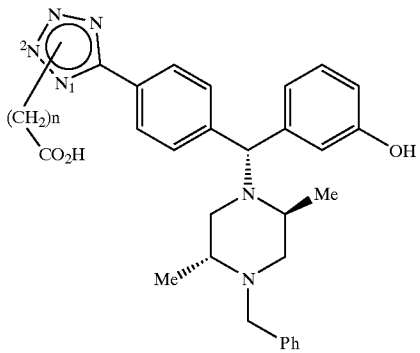

or salts thereof, were prepared by hydrolysis of the corresponding esters (see Examples 14 to 18) by similar methods to that used in Example 19.

EXAMPLE 25

(+)-(5-{4-[(R)-α-(2(S),5(R)-4-Benzyl-2,5-dimethyl-1-piperazinyl)-3-hydroxybenzyl]phenyl}-2-tetrazolyl)ethoxyacetic Acid

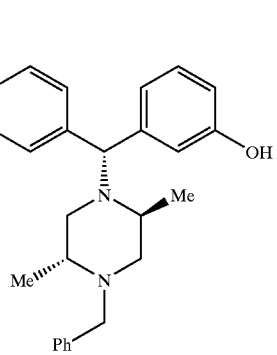

| Ex | Isomer | n | m/z | $R_f$ 80/20/3 | $[\alpha]_D$ | Micro Analysis |
|---|---|---|---|---|---|---|
| 20 | N-1 | 1 | 573 | 0.48 | −16° | Found: C, 65.91; H, 6.41; N, 16.38. $C_{29}H_{32}N_6O_3 \cdot 3/4$ $H_2O$ requires C, 66.21; H, 6.42; N, 15.97% |
| 21 | N-1 | 3 | 541 | 0.33 | −9° | Found: C, 67.37; H, 6.73; N, 15.31. $C_{31}H_{36}N_6O_3 \cdot 1/2$ $H_2O$ requires C, 67.74; H, 6.78; N, 15.29% |
| 22 | N-2 | 3 | 541 | 0.32 | −13° | Found: C, 67.42; H, 6.79; N, 15.45. $C_{31}H_{36}N_6O_3 \cdot 1/2$ $H_2O$ requires C, 67.74; H, 6.78; N, 15.29% |
| 23 | N-1 | 4 | 555 | 0.12 EtOAc | −23° | Found: C, 67.08; H, 6.99; N, 15.15. $C_{32}H_{38}N_6O_3 \cdot 2/3$ $H_2O$ requires C, 67.15; H, 7.10; N, 15.49% |
| 24 | N-2 | 4 | 555 | 0.21 EtOAc | 0.8° | Found: C, 68.27; H, 6.96; N, 15.09. $C_{32}H_{38}N_6O_3 \cdot 1/2$ $H_2O$ requires C. 68.18; H, 6.97; N, 14.91% |

Example 20 (−)-(5-{4-[(R)-α-(2(S),5(R)-4-benzyl-2,5-dimethyl-1-piperazinyl)-3-hydroxybenzyl]phenyl}-1-tetrazolyl)acetic acid.

Example 21 (−)-4-(5-{4-[(R)-α-(2(S),5(R)-4-benzyl-2,5-dimethyl-1-piperazinyl)-3-hydroxybenzyl]phenyl}-1-tetrazolyl)acetic acid.

Example 22 (−)-4-(5-{4-[(R)-α-(2(S),5(R)-4-benzyl-2,5-dimethyl-1-piperazinyl)-3-hydroxybenzyl]phenyl}-2-tetrazolyl)butyric acid.

Example 23 (−)-5-(5-{4-[(R)-α-(2(S),5(R)-4-benzyl-2,5-dimethyl-1-piperazinyl)-3-hydroxybenzyl]phenyl}-1-tetrazolyl)valeric acid.

Example 24 (−)-5-(5-{4-[(R)-α-(2(S),5(R)-4-benzyl-2,5-dimethyl-1-piperazinyl)-3-hydroxybenzyl]phenyl}-2-tetrazolyl)valeric acid.

A solution of the first compound of Preparation 29 (1.40 g) in ethanol (125 ml) was cooled to 0° C. and saturated with hydrogen chloride gas. After 30 minutes the solvent was evaporated to dryness in vacuo to afford a colourless oil. The intermediate imino ether was dissolved in water (50 ml), cooled to 0° C. and treated with water (50 ml). The solution was allowed to warm up to room temperature overnight, after which time aqueous sodium hydroxide solution (5N, 7.5 ml) was added and the resulting solution was allowed to stir at room temperature for 1 hour. The reaction mixture was cooled to 0° C., acidified to pH2 and immediately re-basified to pH 9 with 880 ammonium hydroxide. The solvents were evaporated to dryness in vacuo, and the residue purified by column chromatography over silica gel (80/20/3 dichloromethane/methanol/ammonia) to give the title compound as a gum. The gum was triturated with diethyl ether and filtered to afford the product as a white solid, 1.06 g.

m/z: 557 (MH+). Rf. 0.36 (80/20/3 dichloromethane/methanol/ammonia). Found: C, 64.73; H, 6.69; N, 15.63. $C_{31}H_{36}N_6O_4 \cdot 2/3H_2O \cdot 1/3NH_3$ requires C, 64.83; H, 6.73; N, 15.44%. $[\alpha]_D$+2.5° (c 0.12, methanol).

EXAMPLE 26

(5-{4-[(R)-α-(2(S),5(R)-4-Benzyl-2,5-dimethyl-1-piperazinyl)-3-hydroxybenzyl]phenyl}-1-tetrazolyl) ethoxyacetic Acid

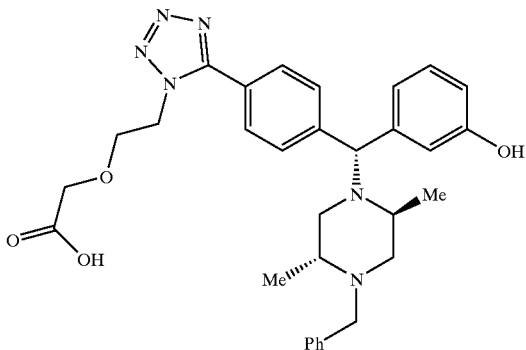

A solution of the second compound of Preparation 29 (137 mg) in ethanol (10 ml) was saturated with hydrogen chloride gas and stirred at ambient temperature for 1 hour. The solvent was evaporated in vacuo to afford a colourless foam which was dissolved in aqueous ethanol (50%, 10 ml) and stirred at ambient temperature for 1 hour after which time sodium hydroxide (51 mg) was added and stirring continued for 18 hours. The solution was acidified to pH 3.5 with concentrated hydrochloric acid and then basified with ammonium hydroxide solution. The solution was evaporated to dryness in vacuo. The residue which was purified by column chromatography over silica gel (dichloromethane/methanol/ammonium hydroxide; 80/20/3) to afford the title compound as a colourless foam, 68 mg.

$\delta_H$ (400 MHz, $d_6$-DMSO): 7.80 (2H, d), 7.58 (2H, d), 7.28 (4H, m), 7.20 (1H, m), 7.12 (1H, t), 6.72 (1H, m), 6.65 (2H, m), 5.08 (1H, bs s), 4.60 (2H, m), 3.90 (2H, m, 3.80 (1H, m), 3.64 (2H, s), 3.22 (1H, m), 2.70–2.50 (4H, m), 2.00 (1H, m), 1.90 (1H, m), 1.04 (6H, m). Found: C, 64.36; H, 6.63; N, 15.77. $C_{31}H_{36}N_6O_4 \cdot 1/2Na \cdot 1/2NH_3$ requires C, 64.39; H, 6.49; N, 15.75%.

EXAMPLE 27

3-(5-{4-[(R)-α-(2(S),5(R)-4-Allyl-2,5-dimethyl-1-piperazinyl)-3-hydroxybenzyl]phenyl}-2-tetrazolyl) propionic Acid

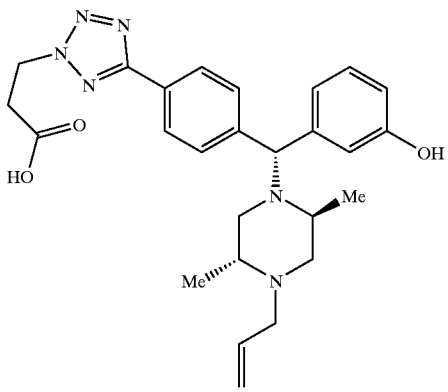

Sodium metal (28.5 mg) was added to ethanol (6 ml) and allowed to dissolve before the compound from Preparation 31 (643 mg) was added and the reaction mixture brought to reflux. After 5 minutes methyl 3-bromopropionate (0.135 ml) was added and the reaction mixture was heated with stirring for 18 hours. The solvent was removed by evaporation in vacuo and the residue purified by column chromatography over silica gel using gradient elution (99/1/0.25 to 80/20/3; dichloromethane/methanol/ammonium hydroxide) to afford the intermediate, 165 mg. The intermediate (165 mg) was dissolved in acetonitrile (10 ml) and tetraethylammonium fluoride (39.5 mg) added. The reaction mixture was stirred for 10 minutes at room temperature and then diluted with water and extracted with ethyl acetate (3×). The combined organic extracts were washed with saturated brine, dried (MgSO4) and evaporated to dryness in vacuo. The residue was purified by column chromatography over silica (97.5/2.5/0.5; dichloromethane/methanol/ammonium hydroxide) to afford an intermediate compound as a 1:1 mixture of methyl and ethyl esters, 72 mg.

To a solution of the above intermediate (72 mg) in methanol (1.8 ml) was added methanolic potassium hydroxide solution (3M, 58 μl) and water (0.9 ml). The reaction mixture was stirred at room temperature for 18 hours and then quenched with dilute hydochloric acid to pH 5.5. The mixture was evaporated to dryness in vacuo and the residue purified by column chromatography, firstly, over silica gel (85/15/3; dichloromethane/methanol/ammonium hydroxide) and secondly over reverse phase resin using gradient elution (100/0 to 45/55; water/acetonitrile) to afford the title compound after freeze-drying, 40 mg.

m/z: 477 (M+). Found: C, 62.75; H, 6.93; N, 16.89. $C_{26}H_{32}N_6O3.6/5H_2O$ requires C, 62.78; H, 6.96; N, 16.87%.

Example 27 $\delta_H$ (400 Mhz, $d_6$-DMSO): 9.30 (1H, br s), 7.90 (2H, d), 7.50 (2H, d), 7.06 (1H, t), 6.64 (3H, m), 5.75 (1H, m), 5.10 (1H, d), 5.06 (1H, d), 4.96 (1H s), 4.80 (2H, t), 3.10 (2H, m), 2.94 (2H, t), 2.80 (1H, dd), 2.68 (1H, d), 2.50 (3H, m), 2.06 (1H, m), 1.82 (1H, t), 1.06 (3H, d), 0.90 (3H, d).

EXAMPLES 28 AND 29

Ethyl 5-(5-{3-[(R)-α-(2(S),5(R)-4-Allyl-2,5-dimethyl-1-piperazinyl)-3-hydroxybenzyl]phenyl}-2-tetrazolyl)valerate and Ethyl 5-(5-{3-[(R)-α-(2(S),5(R)-4-Allyl-2,5-dimethyl-1-piperazinyl)-3-hydroxybenzyl]phenyl}-2-tetrazolyl)valerate

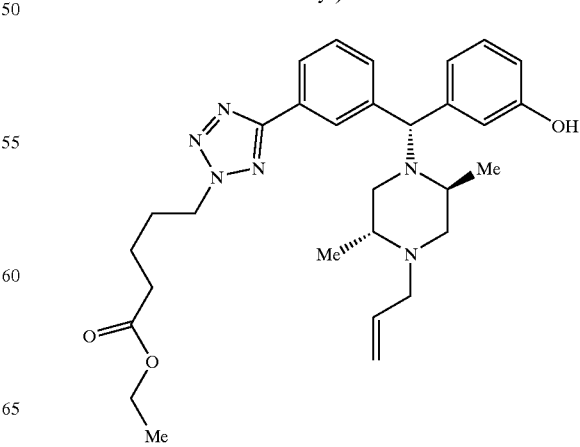

-continued

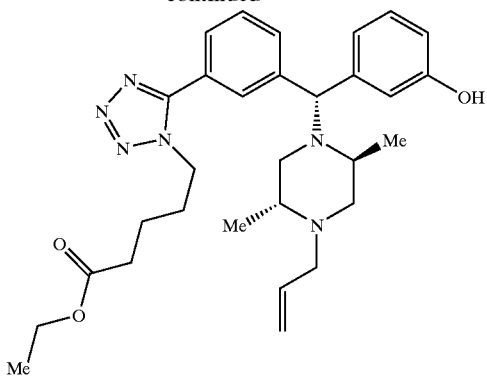

A mixture of the compound of Preparation 33 (2.3 g), potassium carbonate (1.8 g) and ethyl 5-bromovalerate (928 mg) in acetonitrile (60 ml) was heated under a gentle reflux for 18 hours. The cooled reaction mixture was poured into water, extracted into ethyl acetate, dried (sodium sulphate) and evaporated to dryness in vacuo. The crude intermediate was dissolved in acetonitrile (15 ml) and tetraethylammonium fluoride (328 mg) added. After 20 minutes stirring at room temperature the reaction mixture was poured into water and extracted with ethyl acetate. The combined extracts were washed with water and brine and dried (sodium sulphate), and evaporated to dryness in vacuo. The residue was purified by column chromatography over silica gel (99/1/0.5; diethyl ether/ethanol/ammonium hydroxide) to afford the N-2 isomer, 1550 mg m/z: 533 (MH$^+$). Rf: 0.53 (97/3/1; diethyl ether/ethanol/ammonium hydroxide) and the N-1 isomer, 225 mg.

m/z: 533 (MH$^+$). R$_f$: 0.39 (97/3/1; diethyl ether/ethanol/ammonium hydroxide).

Example 28 $\delta_H$ (400 Mhz, CDCl$_3$): 8.16 (1H, s), 7.93 (1H, d), 7.53 (1H, d), 7.36 (1H, t), 7.12 (1H, t), 6.73 (1H, d), 6.63 (2H, m), 5.83 (1H, m), 5.72 (1H, br s), 5.20–5.06 (3H, m), 4.63 (2H, t), 4.10 (2H, q), 3.33 (1H, dd), 2.85 (1H, dd), 2.80 (1H, dd), 2.68 (1H, m), 2.60 (1H, d), 2.56 (1H, m), 2.33 (2H, t), 2.16 (1H, dd), 2.06 (2H, m), 1.96 (1H, m), 1.70 (2H, m), 1.20 (3H, t), 1.15 (3H, d), 0.98 (3H, d).

Example 29 $\delta_H$ (400 Mhz, CDCl$_3$): 7.76 (1H, d), 7.58 (2H, m), 7.50 (1H, t), 7.18 (1H, t), 6.73 (2H, m), 6.63 (1H, s), 6.38 (1H, br s), 5.86 (1H, m), 5.30–5.13 (3H, m), 4.33 (2H, t), 4.13 (2H, q), 3.36 (1H, dd), 2.86 (2H, m), 2.70 (1H, m), 2.60 (1H, m), 2.50 (1H, m), 2.28 (2H, t), 2.16 (1H, dd), 1.98 (1H, dd), 1.90 (2H, m), 1.58 (2H, m), 1.26 (3H, t), 1.18 (3H, d), 1.00 (3H, d).

EXAMPLE 30

(+)-5-(5-{3-[(R)-α-(2(S),5(R)-4-Allyl-2,5-dimethyl-1-piperazinyl)-3-hydroxybenzyl]phenyl}-2-tetrazolyl)valeric Acid

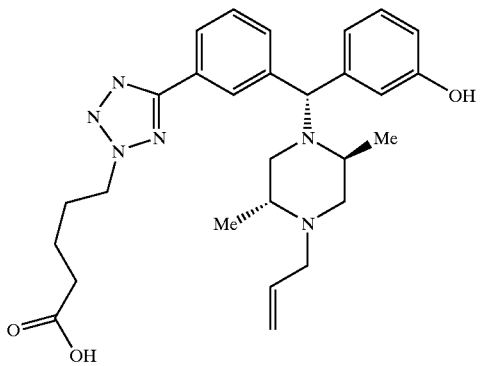

Aqueous sodium hydroxide (2N, 2 ml) was added to a solution of the compound of Example 28 (1.15 g) in dioxane (4 ml) and methanol (2 ml) and the mixture stirred at room temperature for 90 minutes. The reaction was quenched with 2N hydrochloric acid (3 ml) and then evaporated to dryness in vacuo. The residue was purified by column chromatography over polystyrene resin using gradient elution (water/acetonitrile; 100/0 to 40/60) to afford the title compound after freeze-drying, 690 mg.

R$_f$: 0.20 (80/20/3; dichloromethane/methanol/ammonium hydroxide). m/z: 505 (MH$^+$). [α]$_D$+13.6 (c=0.11, methanol). Found: C, 64.83; H, 7.10; N, 16.21. C$_{28}$H$_{36}$N$_6$O$_3$.7/10H$_2$O requires C, 65.02; H, 7.29; N, 16.25%.

EXAMPLE 31

(+)-5-(5-{3-[(R)-α-(2(S),5(R)-4-Allyl-2,5-dimethyl-1-piperazinyl)-3-hydroxybenzyl]phenyl}-1-tetrazolyl)valeric Acid

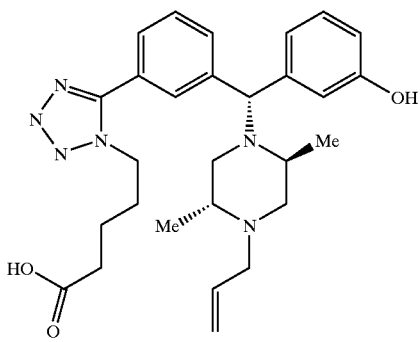

Aqueous sodium hydroxide (2N, 1 ml) was added to a solution of the compound of Example 29 (225 mg) in dioxane (2 ml) and methanol (1 ml) and the mixture stirred at room temperature for 18 hours. The reaction was quenched with 2N hydrochloric acid (3 ml) and then evaporated to dryness in vacuo. The residue was purified by column chromatography over polystyrene resin using gradient elution (water/acetonitrile; 100/0 to 0/100) to afford the title compound after freeze-drying, 169 mg.

$R_f$: 0.21 (80/20/3; dichloromethane/methanol/ammonium hydroxide). m/z: 505 (MH+). $[\alpha]_D$+13.54 (c=0.11, methanol).

Example 31 $\delta_H$ (400 Mhz, $d_6$-DMSO): 11.2 (1H, br s), 7.76–7.48 (4H, m), 7.06 (1H, t), 6.70 (2H, m), 6.60 (1H, d), 5.76 (1H, m), 5.20–5.00 (3H, m), 4.40 (2H, m), 3.30 (1H, br s), 3.16 (1H, m), 2.90–2.40 (5H, m), 2.16–1.98 (3H, m), 1.90–1.68 (3H, m), 1.38 (2, mn), 1.06 (3H, d), 0.92 (3H, d).

EXAMPLES 32 AND 33

Ethyl (5-{3-[(R)-α-(2(S),5(R)-4-Allyl-2,5-dimethyl-1-piperazinyl)-3-hydroxybenzyl]phenyl}-2-tetrazolyl)acetate and Ethyl (5-{3-[(R)-α-(2(S),5(R)-4-Allyl-2,5-dimethyl-1-piperazinyl)-3-hydroxybenzyl]phenyl}-2-tetrazolyl)acetate

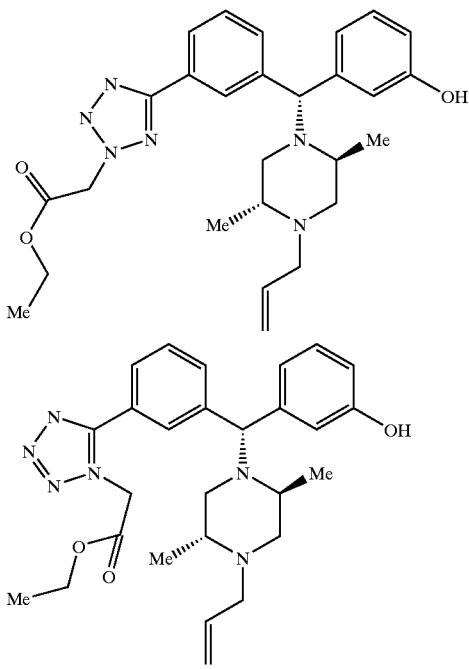

A mixture of the compound of Preparation 33 (2.3 g), potassium carbonate (1.8 g) and ethyl bromoacetate (702 mg) in acetonitrile (60 ml) was heated under a gentle reflux for 3 hours. The cooled reaction mixture was poured into water, extracted into ethyl acetate, dried (sodium sulphate) and evaporated to dryness in vacuo. The residue was purified by column chromatography over silica gel (90/10/0.75; hexane/isopropanol/ammonium hydroxide) to afford two products with the order of elution N-2 isomer, 1200 mg.

m/z: 491 (MH+). $R_f$: 0.21 (95/5; dichloromethane/methanol) and the N-1 isomer, 140 mg. m/z: 491 (MH+). $R_f$: 0.23 (95/5; dichloromethane/methanol).

Example 32 $\delta_H$ (300 Mhz, $d_6$-DMSO): 9.30 (1H, s), 8.10 (1H, s), 7.86 (1H, d), 7.58 (1H, d), 7.50 (1H, t), 7.14 (1H, t), 6.74–6.64 (3H, m), 5.86 (2H, s), 5.76 (1H, m), 5.20–5.00 (3H, m), 4.20 (2H, q), 3.16 (1H, m), 2.85 (1H, dd), 2.73 (1H, d), 2.56 (3H, m), 2.10 (1H, dd), 1.90 (1H, dd), 1.20 (3H, t), 1.06 (3H, d), 0.96 (3H, d).

Example 33 $\delta_H$ (300 Mhz, CDCl$_3$): 7.70 (2H, m), 7.56 (1H, d), 7.48 (1H, t), 7.18 (1H, t), 6.74 (2H, d), 6.60 (1H, s), 5.86 (1H, m), 5.70 (1H, br s), 5.30–5.10 (5H, m), 4.18 (2H, q), 3.38 (1H, dd), 2.86 (2H, m), 2.66 (1H, m), 2.54 (2H, m), 2.16 (1H, t), 1.94 (1H, t), 1.18 (6H, m), 1.00 (3H, d).

EXAMPLES 34 AND 35

(+)-(5-{3-[(R)-α-(2(S),5(R)-4-Allyl-2,5-dimethyl-1-piperazinyl)-3-hydroxybenzyl]phenyl}-2-tetrazolyl) acetic Acid and (5-{3-[(R)-α-(2(S),5(R)-4-Allyl-2,5-dimethyl-1-piperazinyl)-3-hydroxybenzyl]phenyl}-1-tetrazolyl) acetic Acid The following compounds of the formula:

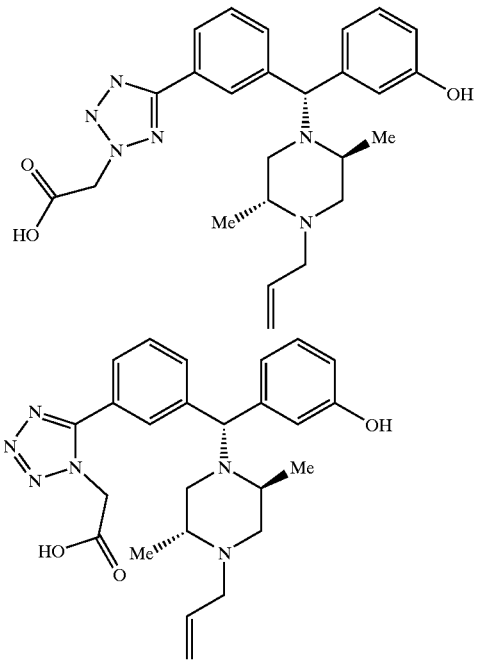

were prepared from the corresponding esters (see Examples 32 and 33) by similar methods to Example 31.

N-2 isomer: (Example 34). m/z: 463 (MH+). $R_f$: 0.22 (80/20/3; dichloromethane/methanol/ammonium hydroxide). Found: C, 62.71; H, 6.65; N, 17.66. $C_{25}H_{30}N_6O_3 \cdot 9/10H_2O$ requires C, 62.72; H, 6.69; N, 17.55%. $[\alpha]_D$+19.8° (c=0.113, methanol).

N-1 isomer: (Example 35). m/z: 463 (MH+). $R_f$: 0.27 (80/20/3, dichloromethane/methanol/ammonium hydroxide). Found: C, 60.86; H, 6.60; N, 17.02. $C_{25}H_{30}N_6O_3 \cdot 8/5H_2O$ requires C, 61.11; H, 6.81; N, 17.10%.

EXAMPLE 36

(+)-5-(5-{4-[(R)-α-(2(S),5(R)-4-Allyl-2,5-dimethyl-1-piperazinyl)-3-hydroxybenzyl]phenyl}-1-tetrazolyl)acetic Acid

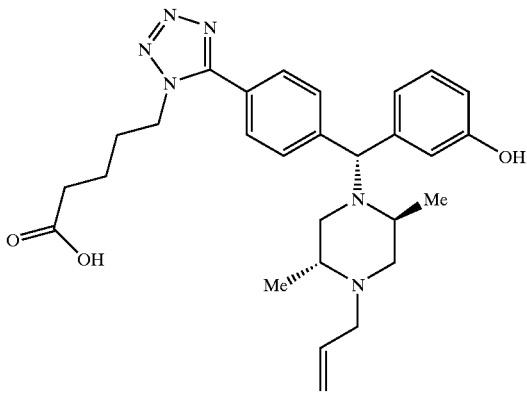

To a solution of the compound of Example 53 (2.42 g) in dichloromethane (50 ml) was added boron tribromide (18 ml of 1M solution in dichloromethane), and the resulting solution was stirred at room temperature for 3 hours. The mixture was evaporated to dryness in vacuo and the residue was basified with ethanolic ammonia and re-evaporated to dryness. A solution of the residue in ethanol (120 ml) and dioxane (20 ml) was added aqueous sodium hydroxide solution (2 N, 26 ml) was stirred at room temperature for 18 hours. The solution was acidified to pH 3 with hydrochloric acid, and then immediately re-basified to pH 9 with 880 ammonia solution, and evaporate to dryness in vacuo. The residue was purified by column chromatography over silica gel (80/20/3, dichloromethane/methanol/ammonia) to afford the title compound which was further purified by chromatography over polystyrene resin (gradient elution; 100% water to 40% acetonitrile/water). The aqueous solution of the product was freeze dried to afford the title compound as a floculent white solid, 0.545 g.

m/z: 505 (MH+). Rf: 0.22 (80/20/3; dichloromethane/methanol/ammonia). Found: C, 64.48; H, 7.25; N, 16.14. $C_{28}H_{36}N_6O_3 \cdot H_2O$ requires C, 64.35; H, 7.33; N, 16.08%. $[\alpha]_D +21.8°$

EXAMPLE 37

5-(5-{4-[(R)-α-(2(S),5(R)-4-Allyl-2,5-dimethyl-1-piperazinyl)-3-methoxybenzyl]phenyl}-1-tetrazolyl) valeric Acid

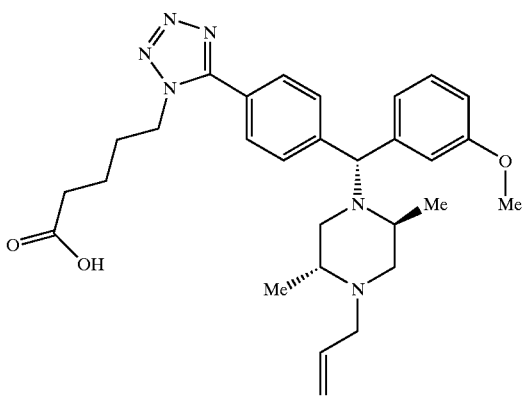

To a solution of the compound of Example 53 (350 mg) in dioxane (20 ml) and methanol (6 ml) was added 1N aqueous sodium hydroxide solution (3.2 ml). The reaction mixture was stirred at ambient temperature for 3 hours, acidified to pH 2 with hydrochloric acid and immediately basified to pH 9 with 880 ammonia. Rotary evaporation followed by purification of the residue by column chromatography over reverse phase polystyrene resin using gradient elution (100% water to 100% acetonitrile) afforded the title compound as a colourless solid, 272 mg.

m/z: 519(MH+). Rf: 0.33 (80/20/3 dichloromethane/methanol/ammonia).

Example 37 $\delta_H$ (300 Mhz, CDCl₃): 7.59 (4H, m), 7.22 (1H, m), 6.90 (2H, m), 6.69 (1H, m), 5.87 (2H, m), 5.22 (3H, m), 4.48 (2H, t), 3.78 (3H, s), 3.40 (1H, m), 2.89 (1H, m), 2.70 (3H, m), 2.20 (4H, m), 1.83 (2H, m), 1.58 (2H, m), 1.08 (6H, m).

EXAMPLE 38

Methyl (5-{4-[(R)-α-(2(S),5(R)-4-Allyl-2,5-dimethyl-1-piperazinyl)-3-hydroxybenzyl]phenyl}-1-tetrazolyl)acetate

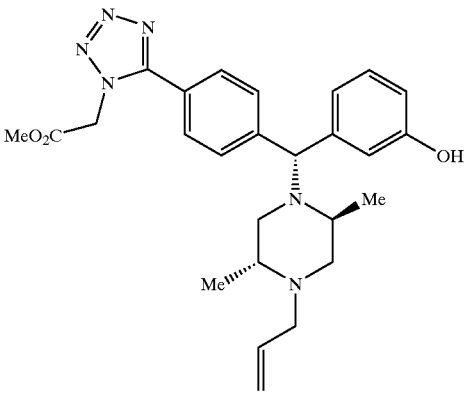

Diethyl acidodicarboxylate (1.46 g) was added to an ice-cold solution of the compound of Preparation 40 (3.96 g), triphenylphosphine (2.26 g) and trimethylsilyl azide (1.16 g) in dry toluene (15 ml). The reaction was stirred at 0° C. for 1 hour, room temperature for 18 hours, and 50° C. for 5 days. The solvent was evaporated in vacuo and the residue purified by column chromatography over silica gel using gradient elution (dichloromethane to 95/5 dichloromethane/methanol) to afford the title compound, 520 mg.

m/z: 477(MH+). Rf: 0.25 (95/5/0.5 dichloromethane/methanol/ammonia).

Example 38 $\delta_H$ (300 Mhz, d₆-DMSO): 9.30 (1H, br s), 7.72 (2H, d), 7.57 (2H, d), 7.17 (1H, t), 6.72 (2H, m), 6.63 (1H, m), 5.90 (1H, m), 5.38–5.18 (5H, m), 3.82 (3H, s), 3.60 (1H, br s), 3.43 (1H, m), 2.90 (2H, m), 2.68 (1H, m), 2.57 (2H, m), 2.18 (1H, m), 1.98 (1H, m), 1.20 (3H, d), 1.03 (3H, d).

EXAMPLE 39

(+)-(5-{4-[(R)-α-(2(S),5(R)-4-Allyl-2,5-dimethyl-1-piperazinyl-3-hydroxybenzyl]phenyl}-1-tetrazolyl) acetic Acid

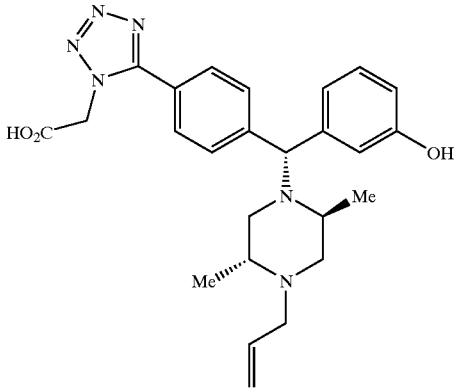

To a solution of the compound of Example 38 (515 mg) in dioxane (8 ml) and methanol (20 ml) was added 5N aqueous sodium hydroxide solution (2.16 ml). The reaction mixture was stirred at ambient temperature for 18 hours, acidified to pH 2 with hydrochloric acid and immediately basified to pH 10 with 880 ammonia. Rotary evaporation followed by purification of the residue by column chromatography over silica gel (80/20/3 dichloromethane/methanol/ammonia) and over reverse phase polystyrene resin using gradient elution (100% water/0% acetonitrile to 100% acetonitrile/0% water) afforded the title compound as a solid, 373 mg.

m/z: 463 (MH+). Rf 0.23 (80/20/3 dichloromethane/methanol/ammonia). $[\alpha]_D$+17.6° (c 0.125, methanol). Found: C, 62.94; H, 6.67; N, 17.90. $C_{25}H_{30}N_6O_3.4/5H_2O$ requires C, 62.96; H, 6.68; N, 17.62%.

EXAMPLES 40 AND 41

(+)-5-Ethyl(5-{4-[(R)-α-(2(S),5(R)-4-Allyl-2,5-dimethyl-1-piperazinyl)-3-hydroxybenzyl]phenyl}-2-tetrazolyl)valerate and Ethyl 5-(5-{4-[(R)-α-(2(S),5(R)-4-Allyl-2,5-dimethyl-1-piperazinyl)-3-hydroxybenzyl]phenyl}-1-tetrazolyl)valerate

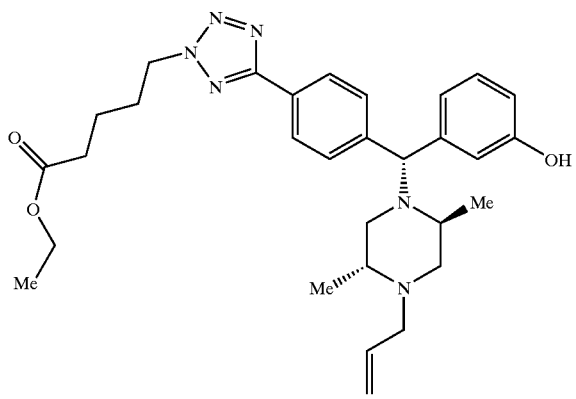

and

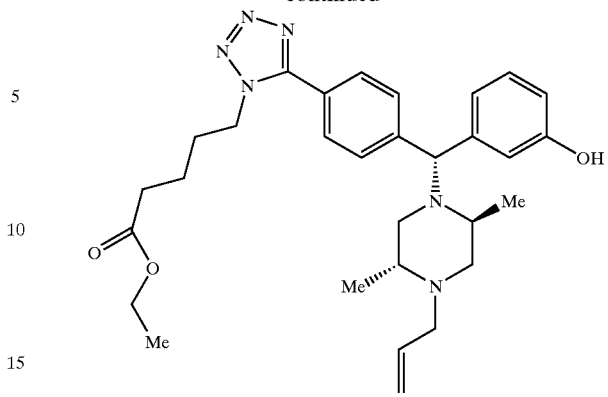

A mixture of the compound of Preparation 31 (2 g), potassium carbonate (1.60 g) and ethyl 5-bromovalerate (807 mg) in acetonitrile (20 ml) was heated under a gentle reflux for 18 hours. The cooled reaction mixture was poured into water, extracted into ethyl acetate, dried (sodium sulphate) and evaporated to dryness in vacuo. The crude intermediate was dissolved in acetonitrile (20 ml) and tetraethylammonium fluoride (865 mg) added. After 20 minutes stirring at room temperature the reaction mixture was poured into water and extracted with ethyl acetate. The combined extracts were washed with water and brine and dried (sodium sulphate), and evaporated to dryness in vacuo. The residue was purified by column chromatography over silica gel (90/10/0.75; hexane/isopropanol/ammonium hydroxide) to afford the N-2 isomer, 1.60 g m/z: 533 (MH+). Rf: 0.30 (85/15/1; hexane/isopropanol/ammonium hydroxide) and the N-1 isomer, 150 mg.

m/z: 533 (MH+). Rf: 0.48 (93/7/1; dichloromethane/methanol/ammonium hydroxide).

Example 40 $[\alpha]_D$=+18.7° (c0.11, methanol). Found: C, 67.34; H, 7.71; N, 15.39. $C_{30}H_{40}N_6O_3$ requires C, 67.64; 7.57; N, 15.78%.

Example 41 $\delta_H$ (300 Mhz, CDCl$_3$): 7.64 (2H, d), 7.58 (2H, d), 7.18 (1H, t), 6.70 (2H, m), 6.62 (1H, s), 5.88 (1H, m), 5.30 (1H, s), 5.22 (1H, d), 4.96 (1H, d), 4.42 (2H, t), 4.10 (2H, q), 3.38 (1H, dd), 2.90 (2H, m), 2.72 (1H, m), 2.56 (2H, m), 2.30 (2H, t), 2.18 (1H, t), 1.98 (3H, m), 1.62 (2H, m), 1.22 (6H, m), 1.02 (3H, d).

EXAMPLE 42

(+)-5-(5-{4-[(R)-α-(2(S),5(R)-4-Allyl-2,5-dimethyl-1-piperazinyl)-3-hydroxybenzyl]phenyl}-2-tetrazolyl)valeric Acid

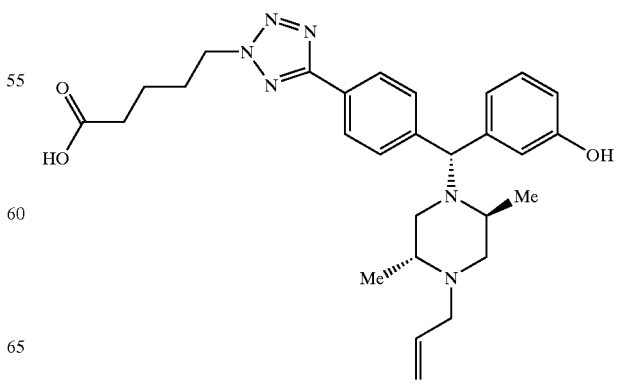

A solution of the compound of Preparation 1 (40 g), benzotriazole (30.9 g) and the compound of Preparation 43 (78.4 g) in toluene (780 ml) was heated under reflux with azeotropic removal of water for 24 hours. The solution was cooled to −20° C. for the dropwise addition of the 3-trimethylsilyloxyphenylmagnesium bromide [704 ml of a solution prepared from 158.7 g of the compound of Preparation 44 and magnesium turnings (17.3 g) in tetrahydrofuiran (800 ml] at such a rate as to maintain the internal temperature in the range −20 to −15° C. The resulting solution was stirred at −20° C. for 5 minutes and then warmed to room temperature overnight. The reaction was quenched with 10% aqueous ammonium chloride solution (2000 ml). The organic phase was washed with water (1000 ml), dried (MgSO$_4$) and evaporated to dryness in vacuo to afford the ethyl ester of the title compound, 101 g as a red oil which was identical to the compound of Example 40.

m/z: 533 (MH$^+$). R$_f$: 0.30 (85/15/1; hexane/isopropanol/ammonium hydroxide).

To a solution of the intermediate ester (14 g) in tetrahydrofuiran (90 ml) was added sodium hydroxide solution (86 ml of a 2N solution) and the mixture stirred at room temperature for 18 hours. The layers were separated and the aqueous solution cooled in an ice-bath for the addition of 2N hydrochloric acid (86 ml) over 20 minutes. The aqueous solution was extracted with ethyl acetate (2×75 m). The combined organic extracts were dried (Na2SO4) and evaporated to dryness in vacuo, and the residue purified by column chromatography over silica gel (80/20/3 dichloromethane/methanol/ammonia) to afford the title compound, 5.2 g.

m/z: 505 (MH+). R$_f$: 0.28 (80/20/3 dichloromethane/methanol/ammonia). [α]$_D$+18.5° (c 0.124, methanol). Found: C, 64.85, H, 7.16; N, 16.28. C$_{28}$H$_{36}$N$_6$O$_3$.4/5H$_2$O requires C, 64.79; H, 7.30; N, 16.19%.

Example 42 δ$_H$ (400 Mhz, d$_6$-DMSO): 9.20 (1H, br s), 7.96 (2H, d), 7.53 (2H, d), 7.12 (1H, t), 6.66 (3H, m), 5.77 (1H, m), 5.18 (1H, m), 5.13 (1H, d), 5.07 (1H, s), 4.69 (2H, t), 3.36 (1H, br s), 3.15 (1H, dd), 2.84 (1H, dd), 2.73 (1H, dd), 2.65–2.47 (3H, m), 2.15 (2H, t), 2.07 (1H, dd), 1.95 (2H, m), 1.86 (1H, m), 1.46 (2H, m), 1.07 (3H, d), 0.94 (3H, d).

EXAMPLE 43

(+)-(5-{4-[(R)-α-(2(S),5(R)-4-Allyl-2,5-dimethyl-1-piperazinyl)-3-hydroxybenzyl]phenyl}-2-tetrazolyl) ethoxyacetic Acid

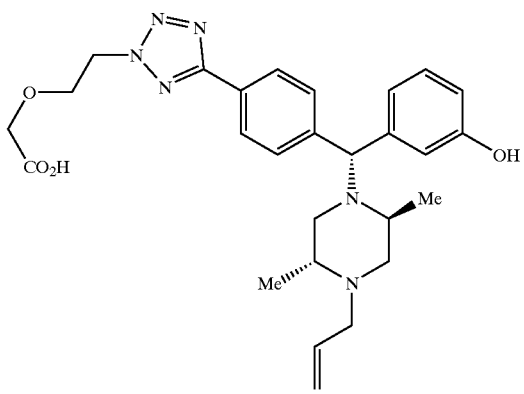

A solution of the compound of Preparation 41 (3.46 g) in ethanol (200 ml) was cooled to 0° C. and saturated with hydrogen chloride gas. After 30 minutes the solvent was evaporated to dryness in vacuo to afford a colourless oil. The intermediate imino ether was dissolved in water (50 ml), cooled to 0° C. and treated with water (50 ml). The solution was allowed to warm up to room temperature overnight, after which time aqueous sodium hydroxide solution (5N, 7.5 ml) was added and the resulting solution was allowed to stir at room temperature for 1 hour. The reaction mixture was cooled to 0° C., acidified to pH2 and immediately re-basified to pH 9 with 880 ammonium hydroxide. The solvents were evaporated to dryness in vacuo, and the residue purified by column chromatography over silica gel (80/20/3 dichloromethane/methanol/ammonia) to give the title compound as a gum. The gum was dissolved in water and freeze-dried to afford the desired product as a white solid, 3.30 g.

m/z: 506 (MH+). M.pt.: 137–140°. Rf: 0.18 (80/20/3 dichloromethane/methanol/ammonia). Found: C, 62.15; H, 6.83; N, 16.23. C$_{27}$H$_{34}$N$_6$O$_4$.4/5H$_2$O requires C, 62.24; H, 6.89; N, 16.13%. [α]$_D$+17.3° (c 0.11, methanol).

EXAMPLE 44

(5-{4-[(R)-α-(2(S),5(R)-2,5-Dimethyl-1-piperazinyl)-3-hydroxybenzyl]phenyl}-2-tetrazolyl) ethoxyacetic Acid

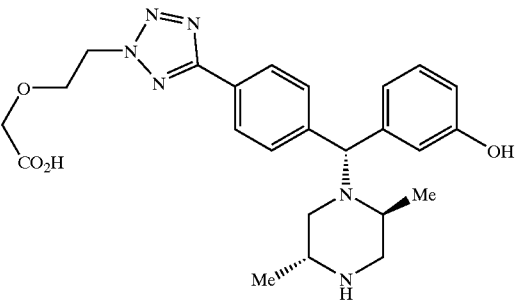

Tris(triphenylphosphine)rhodium(I) chloride (100 mg) was added to a solution of the compound of Example 43 (620 mg) in acetoritrile (20 ml) and water (5 ml). The reaction mixture was heated under a gentle reflux and the solvent allowed to distil off slowly. Additional acetonitrile/water (100 ml; 4:1 v/v) was added a such a rate as to maintain a steady distillation. After the addition of solvent was complete the distillation was continued until the volume was reduced to approximately 50 ml. The cooled solution was poured into ethyl acetate and washed with saturated aqueous sodium bicarbonate solution and brine, dried (MgSO$_4$) and evaporated in vacuo. The residue was purified by column chromatography over silica gel (80/20/3 dichloromethane/methanol/ammonium hydroxide;) to afford the title compound, 123 mg together with unreacted starting material, 460 mg.

m/z: 467 (MH+). Rf: 0.06 (80/20/3 dichloromethane/methanol/ammonia).

Example 44 δ$_H$ (400 Mhz, d$_6$-DMSO): 8.00 (2H d), 7.52 (2H, d), 7.18 (1H, t), 6.80–6.60 (3H, m), 4.86 (2H, m), 4.02 (2H, m), 3.80 (2H, s), 3.50–3.00 (6H, br m), 2.66 (2H, m), 1.85 (2H, m), 1.17 (3H, d), 1.02 (3H, d).

EXAMPLE 45 AND 46

Ethyl (5-{4-[(R)-α-(2(S),5(R)-4-Allyl-2,5-dimethyl-1-piperazinyl)-3-methoxybenzyl]phenyl}-2-tetrazolyl)acetate and Ethyl (5-{4-[(R)-α-(2(S),5(R)-4-Allyl-2,5-dimethyl-1-piperazinyl)-3-methoxybenzyl]phenyl}-1-tetrazolyl)acetate

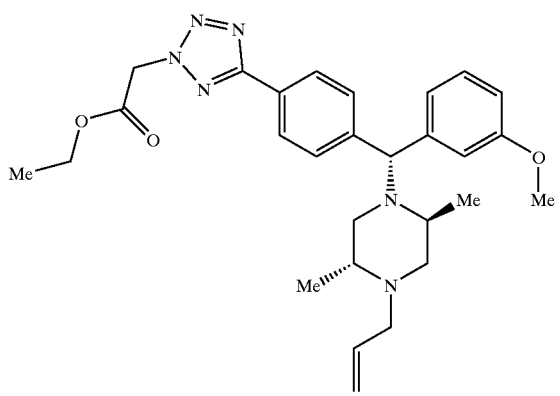

and

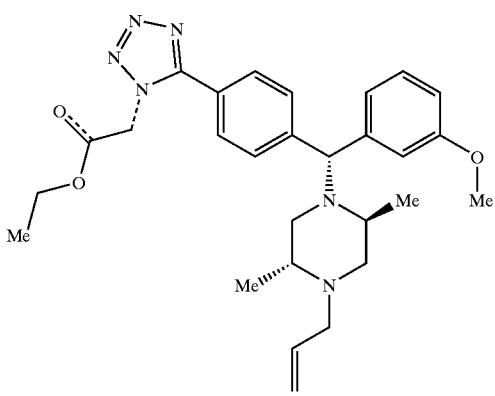

A mixture of the compound of Example 52 (1.0 g), potassium carbonate (990 mg) and ethyl bromoacetate (265 μl) in dry dichloromethane (30 ml) was heated under a gentle reflux for 18 hours. The cooled reaction mixture was poured into water, extracted with dichloromethane, dried (sodium sulphate) and evaporated to dryness in vacuo. The residue was purified by column chromatography over silica gel (90/10/0.75; hexane/isopropanol/ammonium hydroxide) to afford the N-2 isomer (Example 45), 620 mg followed by the N-1 isomer (Example 46), 518 mg.

Example 45: m/z: 505 (MH+). Rf: 0.29 (90/10/0.75; hexane/isopropanol/ammonium hydroxide).

Example 46: m/z: 505 (MH+). Rf: 0.14 (90/10/0.75; hexane/isopropanol/ammonium hydroxide).

Example 45 $\delta_H$ (300 Mhz, CDCl$_3$): 8.07 (2H, d), 7.58 (2H, d), 7.23 (1H, m), 6.8 (3H, m), 5.86 (1H, m), 5.43 (2H, s), 5.19 (3H, m), 4.30 (2H, q), 3.79 (3H, s), 3.38 (1H, dd), 2.84 (2H, m), 2.63 (2H, m), 2.51 (1H, m), 2.14 (1H, m), 1.93 (1H, m), 1.30 (3H, t), 1.20 (3H, d), 1.00 (3H, d).

Example 46 $\delta_H$ (300 Mhz, CDCl$_3$): 7.65 (4H, q), 7.27 (1H, m), 6.3 (3H, m), 5.86 (1H, m), 5.30–5.10 (5H, m), 4.28 (2H, q), 3.80 (3H, s), 3.37 (1H, dd), 2.90–2.40 (5H, m), 2.15 (1H, m), 1.93 (1H, m), 1.27 (3H, t), 1.20 (3H, d), 1.00 (3H, d).

EXAMPLE 47

Ethyl (5-{4-[(R)-α-(2(S),5(R)-4-Allyl-2,5-dimethyl-1-piperazinyl)-3-hydroxybenzyl]phenyl}-2-tetrazolyl)acetate

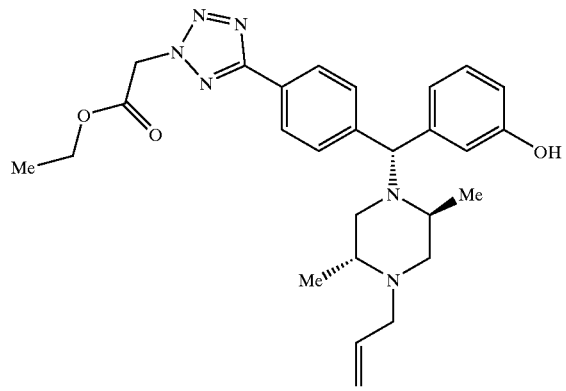

Boron tribromide (1M in dichloromethane, 2.46 ml) was added to a solution of the compound of Example 45 (620 mg) and stirred at room temperature for 6 hours. The reaction mixture was evaporated to dryness in vacuo. The residue was purified by column chromatography over silica gel using gradient elution (95/5/0.5 to 80/20/3 dichloromethane/methanol/ammonium hydroxide) to afford the title compound, 212 mg.

m/z: 491 (MH+). Rf: 0.50 (93/7/1 dichloromethane/methanol/ammonium hydroxide).

Example 47 $\delta_H$ (300 Mhz, CDCl$_3$): 8.07 (2H, d), 7.57 (2H, d), 7.17 (1H, t), 6.73 (3H, m), 5.88 (1H, m), 5.40 (2H, m), 5.20–5.10 (3H, m), 4.28 (2H, q), 3.36 (1H, dd), 2.88 (1H, dd), 2.82 (1H, m), 2.78–2.44 (3H, m), 2.17 (1H, dd), 1.98 (1H, dd), 1.50 (1H, br s), 1.30 (3H, t), 1.17 (3H, d), 1.00 (3H, d).

EXAMPLE 48

(+)-(5-{4-[(R)-α-(2(S),5(R)-4-Allyl-2,5-dimethyl-1-piperazinyl)-3-hydroxybenzyl]phenyl}-2-tetrazolyl) acetic Acid

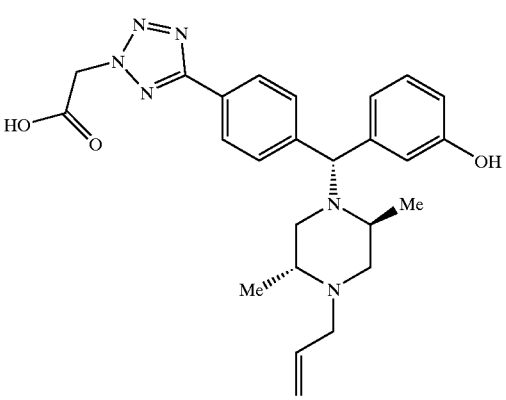

To a solution of the compound of Example 47 (168 mg) in dioxane (4 ml) and methanol (6 ml) was added 2N aqueous sodium hydroxide solution (0.86 ml). The reaction mixture was stirred at ambient temperature for 18 hours, acidified to pH 2 with 2N hydrochloric acid and immediately basified to pH 10 with 880 ammonia. Rotary evaporation followed by purification of the residue by column chromatography over silica gel (80/20/3 dichloromethane/methanol/ammonia) and over reverse phase polystyrene resin using gradient elution (100% water/0% acetonitrile to 100% acetonitrile/0% water) afforded the title compound as a solid after freeze-drying, 130 mg.

m/z: 462 (MH+). Rf: 0.21 (80/20/3 dichloromethane/methanol/ammonia). $[\alpha]_D$+20° (c 0.12, methanol). Found: C, 62.17; H, 6.60; N, 17.25. $C_{25}H_{30}N_6O_3 \cdot H_2O$ requires C, 62.48; H, 6.71; N, 17.49%.

EXAMPLES 49 AND 50

(±)-Ethyl 2-(5-{4-[(R,S)-α-(4-Benzyl-1-piperazinyl)-3-hydroxybenzyl]-phenyl}-2-tetrazolyl) acetate and (±)-Ethyl 2-(5-{4-[(R,S)-α-(4-Benzyl-1-piperazinyl)-3-hydroxybenzyl]-phenyl}-1-tetrazolyl) acetate

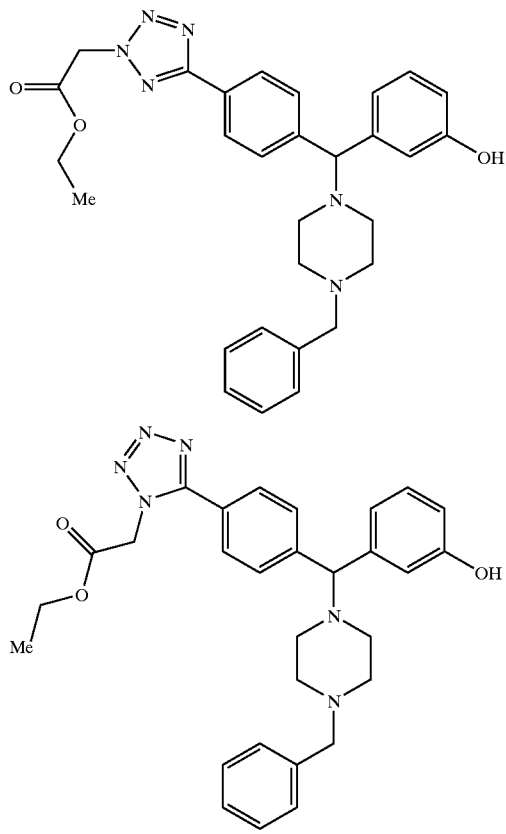

A solution of the compound of Preparation 4(b) (0.54 g), ethyl bromoacetate (167 mg) and cesium carbonate (0.49 g) in dimethylformamide (20 ml) was stirred at room temperature for 18 hours. The reaction mixture was partitioned between saturated sodium chloride solution and ethyl acetate. The aqueous layer was separated and extracted with further ethyl acetate. The combined organic extracts were washed with water, saturated brine solution, dried (sodium sulphate) and evaporated to dryness in vacuo. The residue was dissolved in tetrahydrofuran (20 ml) and tetraethylammonium fluoride (400 g) in water (2 ml) added. The mixture was stirred at room temperature for 12 hours then partitioned between ethyl acetate and water. The layers were separated and the organic phase was washed with water and saturated brine solution, dried (magnesium sulphate) and evaporated to dryness in vacuo. The residue was purified by column chromatography over silica gel using gradient elution (25–50% ethyl acetate/hexane) to afford in order of elution the N-2 isomer, 310 mg, followed by the N-1 isomer, 75 mg,.

N-2 Isomer: (Example 49): m/z: 513 (MH+). $\delta_H$ (300 MHz, $d_6$-DMSO): 9.28 (1H, s), 7.94 (2H, d), 7.56 (2H, d), 7.32–7.14 (5H, m), 7.06 (1H, t), 6.80 (2H, m), 6.56 (1H, d), 5.82 (2H, s), 4.26 (1H, s), 4.20 (2H, q), 3.46 (2H, s), 2.50–2.20 (8H, m), 1.20 (3H, t).

N-1 Isomer: (Example 50): m/z: 513 (MH+). $\delta_H$ (400 MHz, $d_6$-DMSO): 9.30 (1H, s), 7.68 (2H, d), 7.60 (2H, d), 7.40–7.20 (5H, m), 7.08 (1H, t), 6.84 (2H, m), 6.58 (1H, d), 5.60 (2H, s), 4.30 (1H, s), 4.06 (2H, q), 3.48 (2H, s), 2.50–2.20 (8H, m), 1.04 (3H, t).

EXAMPLE 51

(±)-2-(5-{4-[(R,S)-α-(4-benzyl-1-piperazinyl)-3-hydroxybenzyl]-phenyl}-1-tetrazolyl)acetic Acid

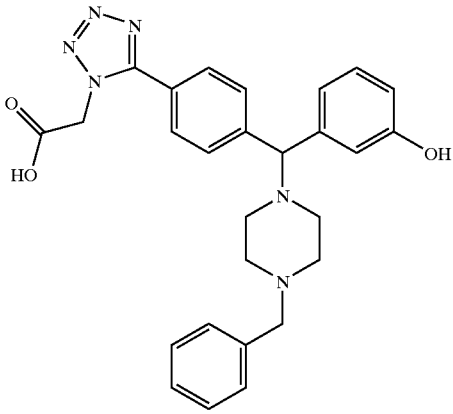

Aqueous sodium hydroxide (2N, 0.5 ml) was added to a solution of the compound of Example 50 (70 mg) in methanol (10 ml) and the mixture stirred at room temperature for 18 hours. The reaction was quenched with 2N hydrochloric acid (3 ml) and then evaporated to dryness in vacuo. The residue was purified by column chromatography over silica gel (80/20/3 dichloromethane/methanol/ammonium hydroxide) to afford the title compound, 69 mg.

m/z.: 485 (MH+). $\delta_H$ (400 MHz, $d_6$-DMSO): 7.74 (2H, d), 7.60 (2H, d), 7.40–7.00 (6H, m), 6.84 (2H, m), 6.60 (1H, m), 5.14 (2H, s), 4.32 (1H, s), 3.70 (2H, s), 3.18 (1H, s), 2.70–2.30 (8H, m). Found: C, 60.38; H, 5.80; N, 16.51. $C_{27}H_{28}N_6O_3 \cdot Na \cdot 3/2H2O \cdot 1/4NH_3$ requires C, 60.33; H, 5.73; N, 16.29%.

EXAMPLE 52

4-[(R)-α-(2(S),5(R)-4-Allyl-2,5-dimethyl-1-piperazinyl)-3-methoxybenzyl]phenyltetrazole

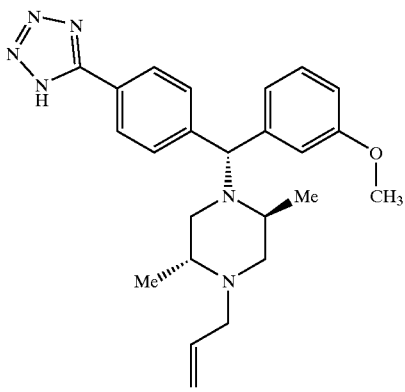

A solution of the compound of Preparation 3 (3.26 g), dibutyltin oxide (780 mg) and trimethylsilyl azide (2.54 g) in dry toluene was stirred at 70° C. under nitrogen for 48 hours, after which time the reaction was quenched by the addition of 2N hydrochloric acid. The pH of the solution was adjusted to pH 10 by the addition of 0. 880 ammonia solution and pre-absorption silica gel added and the solvents evaporated in vacuo. The residue was purified by column chromatography over silica gel using gradient elution (85/15/2 to 80/20/3 dichloromethane/methanol/ammonia) to afford the title compound as a brown gum, 3.28 g.

m/z: 420 (MH+). Rf: 0.31 (80/20/3 dichloromethane/methanol/ammonia). $\delta_H$ (300 mhz, CDCl$_3$): 8.04 (2H, d), 7.43 (2H, d), 7.15 (1H, t), 6.93 (1H, bs), 6.74 (3H, m), 5.93 (1H, m), 5.32 (2H, n), 5.04 (1H, s), 3.68 (3H, s), 3.58 (1H, m), 3.28 (1H, m), 3.09 (1H, m), 2.97 (2H, m), 2.80 (1H, m), 2.55 (1H, m), 2.30 (1H, m), 1.18 (6H, 2×d).

EXAMPLE 53

Ethyl 5-(5-{4-[(R)-α-(2(S),5(R)-4-Allyl-2,5-dimethyl-1-piperazinyl)-3-methoxybenzyl]phenyl}-1-tetrazolyl)valerate

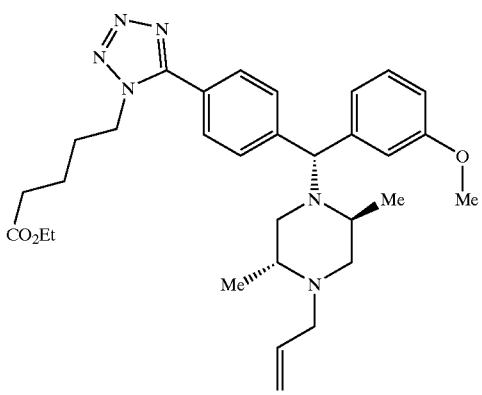

Phosphorus pentachloride (1.53 g) was added to a solution of the compound of Preparation 36 (2.95 g) in dry toluene (75 ml), and the resulting mixture was stirred at 75° C. for 2 hours. The solution was cooled to ambient temperature and trimethylsilyl azide (1.17 g) added. The reaction mixture was maintained at ambient temperature, with stirring, for 18 hours. The solution was diluted with ethyl acetate (150 ml) and washed with saturated sodium hydrogen carbonate, and the organic extracts were evaporated to dryness in vacuo. The brown residue was purified by column chromatography over silica gel (98/2; dichloromethane/methanol) to afford the title compound, 2.43 g.

m/z: 547 (MH+). Rf. 0.39 (95/5; dichloromethane/methanol). $\delta_H$ (300 MHz, CDCl$_3$): 7.65 (2H, d), 7.58 (2H, d), 7.25 (1H, t), 6.80 (3H, q), 5.87 (1H, m), 5.18 (3H, m), 4.42 (2H, t), 4.12 (2H, q), 3.78 (3H, s), 3.35 (1H, dd), 2.85 (2H, m), 2.60 (3H, m), 2.31 (2H, t), 2.15 (1H, m), 2.00 (3H, m), 1.68 (2H, m), 1.20 (6H, m), 1.00 (3H, d).

EXAMPLE 54

4-5-{[(R)-α-(2(S),5(R)-4-Allyl-2,5 dimethyl-1-piperazinyl)-3-methanesulphonylbenzyl]phenyl}-1H-tetrazole

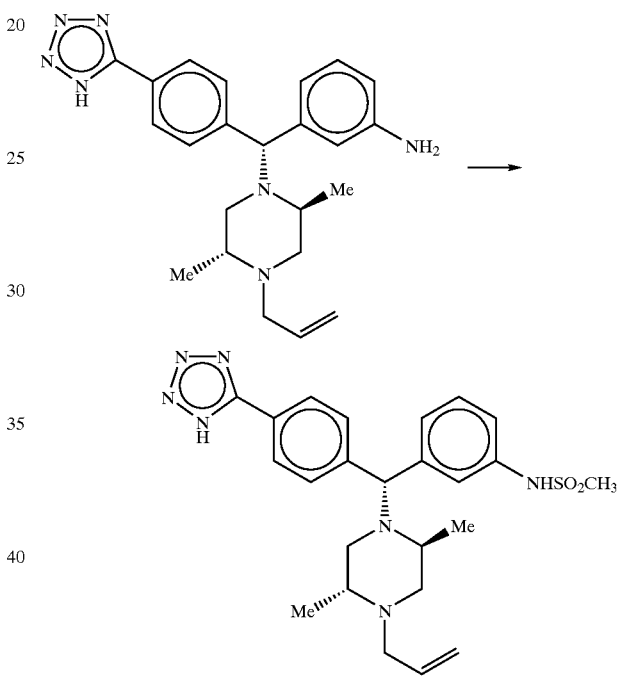

To a suspension of the anilinotetrazole of Preparation 48; (600 mg; 0 0015 mole) in tetrahydrofuran was added triethylamine (161 mg; 0.0016 mole) to give a bright yellow solution. Trimethylsilyl chloride (178 mg; 0.0016 mole) was added and stirring continued for 1.5 hours. Triethylamine hydrochloride precipitated. Pyridine (468 ml; 0.0060 mole) was added followed by methanesulfonyl chloride (344 mg; 0.0030 mole) and the reaction stirred at room temperature for 18 hours. Water (10 ml) was added and the reaction acidified to pH2 with concentrated hydrochloric acid; then basified with ammonium hydroxide solution (s.g=0.880). The mixture was rotary evaporated to dryness and the residue re-absorbed onto silica. This was then flash chromatographed on silica; eluant 90/10/1.5→80/20/1 CH$_2$Cl$_2$/MeOH/NH$_4$OH to give 220 mg of the desired product.

m/z: 483 (MH$^+$). $\delta_H$ (400 MHz, d$_6$-DMSO): 7.94 (2H, d), 7.46 (2H, d), 7.32 (1H, t), 7.20 (1H, s), 7.10 (1H, d), 7.02 (1H, d), 5.80 (1H, m), 5.26 (1H, d), 5.20 (1H, d), 5.12 (1H, s), 3.36 (1H, dd), 3.18 (1H, s), 3.04 (1H, dd), 2.94 (3H, s), 2.88 (1H, d), 2.74 (1H, m), 2.68–2.56 (2H, m), 2.32 (1H, dd), 1.88 (1H, dd), 1.12 (3H, d), 1.00 (3H, d).

EXAMPLE 55

(±)-[(R,S)-α-(4-Allyl-1-piperazinyl)-3-(hydroxybenzyl)phenyltetrazole

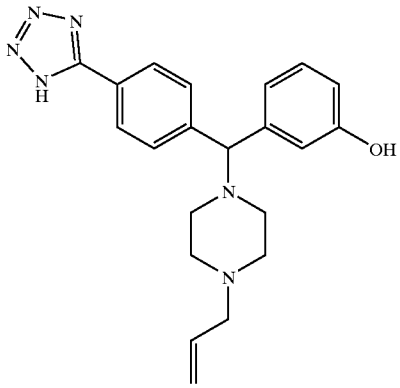

Tetraethylammonium fluoride (228 mg) was added to a solution of the compound from Preparation 50 (500 mg) in acetonitrile (10 ml) and the reaction stirred at room temperature for 30 minutes. The reaction mixture was then evaporated to dryness in vacuo. The residue was purified by column chromatography over silica gel (80/20/3 dichloromethane/methanol/ammonium hydroxide). This material was further purified over a polystyrene reverse phase resin, using gradient elution (90/10–50/50 water/acetonitrile). The acetonitrile was evaporated in vacuo and the remaining aqueous solution was frozen and lyophilised to afford the title compound as a white solid, 131 mg.

m/z: 377 (MH$^+$). R$_f$: 0.24 (70/30/3 ethyl acetate/methanol/diethylamine). δ$_H$ (400 MHz, DMSO-d$_6$): 7.82 (2H, d), 7.49 (2H, d), 7.08 (1H, dd), 6.86 (2H, m), 6.58 (1H, d), 5.60 (1H, m), 5.20 (2H, m), 4.26 (1H, s), 3.10 (2H, d), 2.58 (4H, m), 2.38 (4H, m).

EXAMPLES 56 AND 57

(±)-Ethyl-(5-{4-[(R,S)-α-(4-Allyl-1-piperazinyl)-3-hydroxybenzyl]phenyl}-1-tetrazolyl)acetate and (±)-Ethyl-(5-{4-[(R,S)-α-(4-Allyl-1-piperazinyl)-3-hydroxybenzyl]phenyl}-2-tetrazolyl})acetate

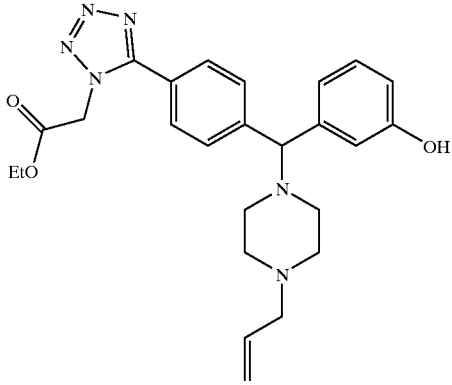

-continued

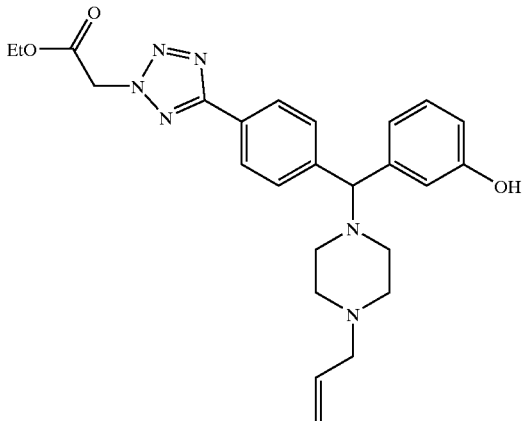

Potassium carbonate (1.27 g) and ethyl bromoacetate (344 μl) were added to a solution of the compound from Preparation 50 (1.5 g) in acetonitrile (60 ml), and the reaction stirred under reflux for 20 hours. On cooling, water was added and the reaction mixture was extracted with ethyl acetate (3×50 ml), the combined organic extracts dried (Na$_2$SO$_4$) and evaporated to dryness in vacuo. This material was redissolved in acetonitrile (10 ml), tetraethylammonium fluoride (694 mg) added and the reaction stirred at room temperature for an hour. Water was added and the mixture extracted with ethyl acetate (2×20 ml), the combined organic extracts dried (Na$_2$SO$_4$) and evaporated to dryness in vacuo to give an orange foam. The residue was purified by column chromatography over silica gel using gradient elution (70/30–100/0 ethyl acetate/hexane) to afford the N2 isomer, 270 mg. m/z: 463 (MH$^+$). R$_f$: 0.25 (ethyl acetate). δ$_H$ (300 MHz, DMSO-d$_6$): 9.30 (1H, s), 7.98 (2H, d), 7.58 (2H d), 7.06 (1H, dd), 6.85 (2H, m), 6.56 (1H, d), 5.84 (2H, s), 5.76 (1H, m), 5.10 (2H m), 4.25 (1H, s), 4.19 (2H, q), 2.92 (2H, d), 2.34 (8H, m), 1.18 (3H, t). and the N1 isomer, 35 mg. R$_f$: 0.13 (ethyl acetate).

EXAMPLE 58

(±)-Ethyl 4-(5-{4-[(R,S)-α-(4-Allyl-1-piperazinyl)-3-hydroxybenzyl]phenyl}-1-tetrazolyl)butyrate

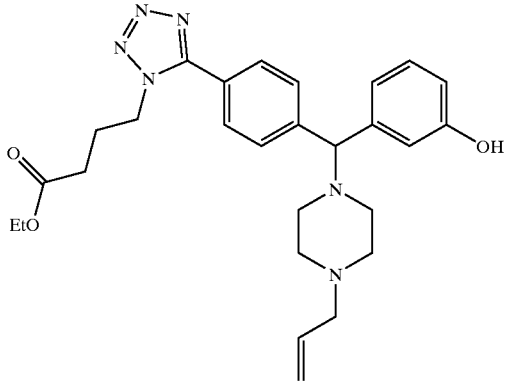

Tetraethylammonium fluoride (67 mg) was added to a solution of the first compound in the drawings of Preparation 51 (200 mg) in acetonitrile (4 ml) and the reaction stirred at room temperature for 30 minutes. Water was added and the mixture extracted with ethyl acetate (3×10 ml). The combined organic extracts were dried (Na$_2$SO$_4$), and evaporated to dryness in vacuo. The residue was purified by column chromatography over silica gel using gradient elution (85/15/1.5–80/20/1.5 hexane/isopropanol/ammonium hydroxide) to afford the title compound, 130 mg.

m/z: 491 (MH$^+$). R$_f$: 0.24 (80/20/1.5 hexane/isopropanol/ammonium hydroxide). δ$_H$ (300 Mhz, CDCl$_3$): 7.60 (4H, s), 7.14 (1H, dd), 6.96 (1H, d), 6.88 (1H, s), 6.67 (1H, d), 5.86 (1H, m), 5.16 (2H, m), 4,48 (2H, t), 4.26 (1H, s), 4.02 (2H, q), 3.02 (2H, d), 2.49 (8H, m), 2.38 (2H, t), 2.24 (2H, m), 1.20 (3H, t).

EXAMPLE 59

(±)-Ethyl 4-(5-{4-[(R,S)-α-(4-Allyl-1-piperazinyl)-3-hydroxybenzyl]phenyl}-2-tetrazolyl)butyrate

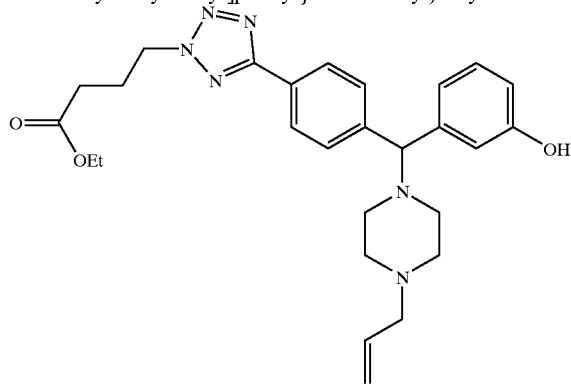

The title compound was prepared using the second compound in the drawings of Preparation 51, following a similar procedure to that described in Example 58, and was obtained in 69% yield.

m/z: 491 (MH$^+$). R$_f$: 0.38 (80/20/1.5 hexane/isopropanol/ammonium hydroxide). δ$_H$ (300 MHz, DMSO-d$_6$): 9.29 (1H, s), 7.96 (2H, d), 7.55 (2H, d), 7.05 (1H, dd), 6.82 (2H, m), 6.54 (1H, d), 5.78 (1H, m), 5.10 (2H, m), 4.74 (2H, t), 4.22 (1H, s), 4.00 (2H, q), 2.90 (2H, d), 2.35 (10H, m), 2.18 (2H, m), 1.14 (3H, t).

EXAMPLE 60

(±)-(5-{4-(R,S)-α-(4-Allyl-1-piperazinyl)-3-hydroxybenzyl]phenyl}-2-tetrazolyl)acetic Acid

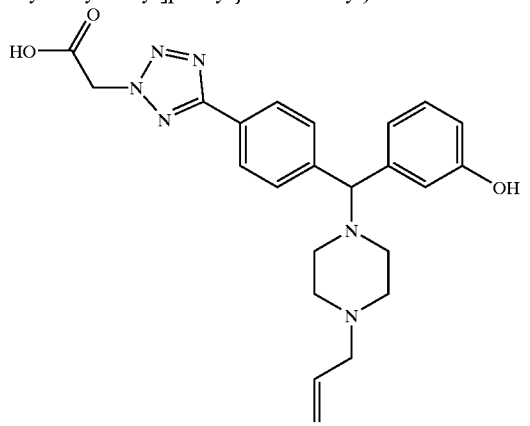

2N aqueous sodium hydroxide solution (1 ml) was added to a solution of the compound of Example 57 (250 mg) in methanol (2 ml) and dioxan (4 ml), and the reaction stirred at room temperature for an hour. The pH of the reaction was adjusted to 5 using 2N aqueous hydrochloric acid and the mixture evaporated to dryness in vacuo. The residue was purified by column chromatography over silica gel (70/30/3 ethyl acetate/methanol/ammonium hydroxide), and this material was further purified over a polystyrene reverse phase resin using gradient elution (80/20–50/50 water/acetonitrile). The acetonitrile was evaporated in vacuo and the remaining aqueous solution was frozen and lyophilised to afford the title compound as a white solid, 190 mg.

m/z: 435 (MH$^+$). R$_f$: 0.2 (80/20/3 dichloromethane/methanol/ammonium hydroxide). δ$_H$ (300 MHz, DMSO-d$_6$): 9.40 (1H, br.s), 7.99 (2H, d), 7.57 (2H, d), 7.08 (1H, dd), 6.84 (2H, m), 6.58 (1H, d), 5.83 (1H, m), 5.47 (2H, s), 5.26 (2H, m), 4.30 (1H, s), 3.28 (2H, d), 2.74 (4H, m), 2.40 (4H, m).

EXAMPLES 61 TO 63

The following compounds of the general formula:

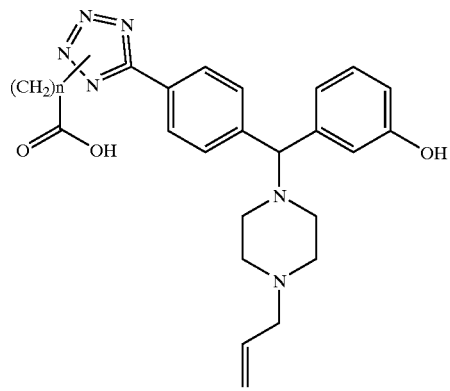

were prepared by hydrolysis of the corresponding esters, Examples 56, 58 and 59, by similar methods to that used in Example 60.

| Ex | Isomer | n | m/z | R$_f$(a) | $^1$Hnmr/Analytical data |
|---|---|---|---|---|---|
| 61 | 1 | 1 | 435 | 0.26 | δ$_H$(300 MHz, DMSO-d$_6$): 9.40(1H, br.s), 7.74 (2H, d), 7.59(2H, d), 7.08(1H, dd), 6.84(2H, m), 6.59(1H, d) 5.80(1H, m), 5.24(2H, m), 5.08(2H, s), 4.30(1H, s), 3.22(2H, d), 2.68 (4H, m), 2.36(4H, m). |

| Ex | Isomer | n | m/z | $R_f$(a) | $^1$Hnmr/Analytical data |
|---|---|---|---|---|---|
| 62 | 1 | 3 | 463 | 0.18 | $\delta_H$(300 MHz, DMSO-$d_6$): 7.72(2H, d), 7.60 (2H, d), 7.07(1H, dd), 6.84(2H, m), 6.57 (1H, d), 5.76(1H, m), 5.10(2H, m), 4.45(2H, t), 4.29(1H, s), 3.28(1H, br.s), 2.92(2H, d), 2.36(8H, m), 2.25(2H, t), 2.01(2H, m). Found: C, 61.26; H, 6.31; N, 16.64. $C_{25}H_{30}N_6O_3$.16/10 $H_2O$ requires C, 61.11; H, 681; N, 17.10% |
| 63 | 2 | 3 | 463 | 0.24 | $\delta_H$(400 MHz, DMSO-$d_6$): 9.32(1H, br.s), 7.98 (2H, d), 7.58(2H, d), 7.07(1H, dd), 6.84(2H, m), 6.58(1H, d), 5.78(1H, m), 5.12(2H, m), 5.74(2H, t), 4.24(1H, s), 2.92(2H, d), 2.34 (10H, m), 2.14(2H, m). Found: C, 62.83; H, 6.40; N, 17.63. $C_{25}H_{30}N_6O_3$.3/4 $H_2O$ requires C, 63.07; H, 6.67; N, 17.65% |

(a): 80/20/3 dichloromethane/methanol/ammonium hydroxide

Example 61. (±)-(5-{4-[(R,S)-α-(4-allyl-1-piperazinyl)-3-hydroxybenzyl]phenyl}-1-tetrazolyl)acetic acid.
Example 62. (±)-4-(5-{4-[(R,S)-α-(4-allyl-1-piperazinyl)-3-hydroxybenzyl]phenyl}-1-tetrazolyl)butyric acid.
Example 63. (±)-4-(5-{4-[(R,S)-α-(4-allyl-1-piperazinyl)-3-hydroxybenzyl]phenyl}-2-tetrazolyl)butyric acid.

EXAMPLE 64

(±)-Ethyl 5-(5-{4-[(R,S)-α-(4-Allyl-1-piperazinyl)-3-methoxybenzyl]phenyl}-1-tetrazolyl)valerate Hydrochloride

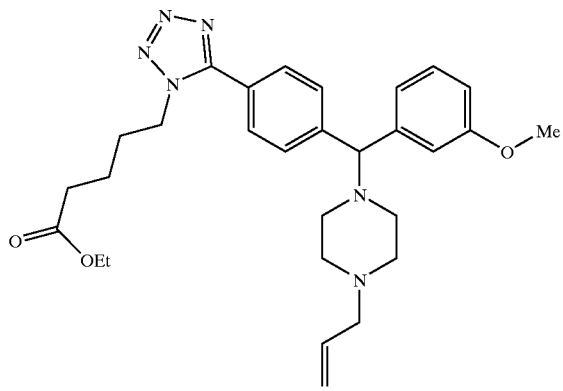

A solution of the compound from Preparation 57 (582 mg) and phosphorus pentachloride (368 mg) in dry toluene (30 ml), was stirred at 70° C. for 90 minutes. On cooling, trimethylsilyl azide (785 μl) was added and the reaction stirred at room temperature for 72 hours. Saturated aqueous sodium hydrogen carbonate solution was added and the mixture extracted with ethyl acetate (3×30 ml). The combined organic extracts were washed with water and brine, then dried ($Na_2SO_4$), and evaporated to dryness in vacuo, to give a brown gum. The residue was purified by column chromatography over silica gel (80/20/1.5 hexane/isopropanol/ammonium hydroxide), to afford the title compound, 218 mg.

m/z: 519(MH$^+$). $\delta_H$(300 MHz, $CDCl_3$): 8.17 (2H, d), 7.78 (2H, d), 7.59 (1H, s), 7.37 (2H, m), 6.92 (1H, d), 6.12 (1H, m), 5.60 (2H, m), 5.08 (1H, s), 4.40 (2H, t), 4.22 (2H, m), 4.08 (2H, q), 3.94 (2H, m), 3.86 (3H, s), 3.68 (2H, d), 3.52 (4H, m), 2.30 (2H, t), 1.99 (2H, m), 1.64 (2H, m), 1.22 (3H, t).

EXAMPLE 65

(±)-5-(5-{4-[(R,S)-α-(4-Allyl-1-piperazinyl)-3-hydroxybenzyl]phenyl}-1-tetrazolyl)valeric Acid

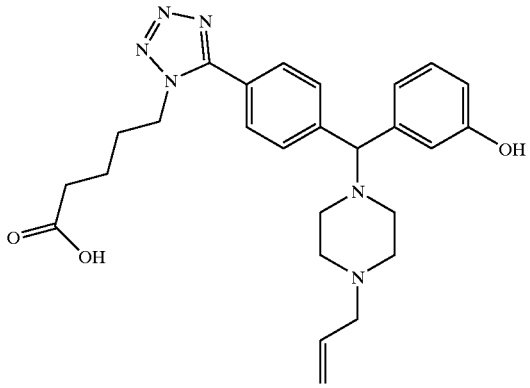

A solution of boron tribromide in dichloromethane (10.5 ml, 1M) was added dropwise to a solution of the compound of Example 64 (2.73 g), in dichloromethane (25 ml) and the reaction stirred under a nitrogen atmosphere at room temperature for 6 hours. Aqueous saturated sodium hydrogen carbonate solution was added and the mixture extracted with dichloromethane (3×50 ml). The combined organic extracts were washed with water and brine, dried ($Na_2SO_4$) and evaporated to dryness in vacua, to give a brown foam. A solution of this material in dioxan (10 ml), methanol (5 ml) and 2N aqueous sodium hydroxide solution (3 ml) was stirred at room temperature for 20 hours. The mixture was acidified using 2N hydrochloric acid, then basified using ammonium hydroxide solution, and the mixture evaporated to dryness in vacuo. The residue was purified by column chromatography over silica gel (80/20/3 dichloromethane/methanol/ammonium hydroxide) and was further purified over a polystyrene reverse phase resin using gradient elution (100/0–0/100 water/acetonitrile). The acetonitrile was evaporated in vacuo and the remaining aqueous solution was frozen and lyophilised to afford the title compound as a white solid, 238 mg.

m/z: 477 (MH$^+$). $\delta_H$ (300 MHz, DMSO-d$_6$): 10.50 (1H, br.s), 7.70 (2H, d), 7.61 (2H, d), 7.08 (1H, dd), 6.84 (2H, m), 6.57 (1H, d), 5.79 (1H, m), 5.12 (2H, m), 4.44 (2H, t), 4.33 (1H, s), 3.20 (1H, br.s), 2.94 (2H, d), 2.40 (4H, m), 2.34 (4H, m), 2.15 (2H, t), 1.82 (2H, m), 1.44 (2H, m). Found: C, 63.60; H, 6.83; N, 17.05. $C_{26}H_{32}N_6O_3 \cdot 4/5H_2O$ requires C, 63.60; H, 6.90; N, 17.12%.

EXAMPLE 66

(±)-Ethyl 2-(5-{4-[(R,S)-α-(4-Allyl-1-piperazinyl)-3-(hydroxybenzyl)phenyl]-2-tetrazolyl})ethoxyacetate

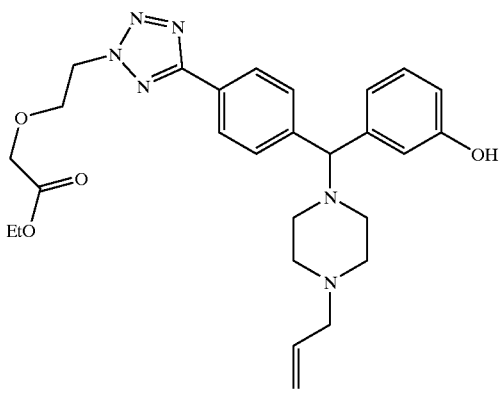

An ice-cooled solution of the compound of Preparation 59 (1.6 g) in ethanol (50 ml) was saturated with hydrogen chloride gas and stirred for 45 minutes. The reaction mixture was evaporated to dryness in vacuo, to give a white solid. A solution of this material in ethanol (5 ml), was cooled to 0° C., and water (5 ml) added. The resulting solution was stirred at 0° C. for 90 minutes, ammonium hydroxide solution added and the mixture extracted with dichloromethane (2×25 ml). The combined organic extracts were dried (Na$_2$SO$_4$) and evaporated to dryness in vacuo, to give a white foam. The residue was purified by column chromatography over silica gel (95/5/0.5 dichlorometahne/methanol/ammonium hydroxide) to afford the title compound, 1.24 g.

m/z: 507 (MH$^+$). R$_f$: 0.59 (90/10/1 diethyl ether/ethanol/ammonium hydroxide). $\delta_H$ (400 MHz, CDCl$_3$): 8.07 (2H, d), 7.54 (2H, d), 7.15 (1H, dd), 6.98 (1H, d), 6.90 (1H, s), 6.66 (1H, d), 6.14 (1H, br.s), 5.88 (1H, m), 5.18 (2H, m), 4.87 (2H, t), 4.19 (5H, m), 4.08 (2H, s), 3.04 (2H, d), 2.52 (8H, m), 1.26 (3H, t). Found: C, 63.38; H, 6.69; N, 16.46. $C_{27}H_{34}N_6O_4 \cdot 1/5H_2O$ requires C, 63.56; H, 6.80; N, 16.47%.

EXAMPLE 67

(±)-2-(5-{4-[(R,S)-α-(4-Allyl-1-piperazinyl)-3-hydroxybenzyl]phenyl}-2-tetrazolyl)ethoxyacetic Acid

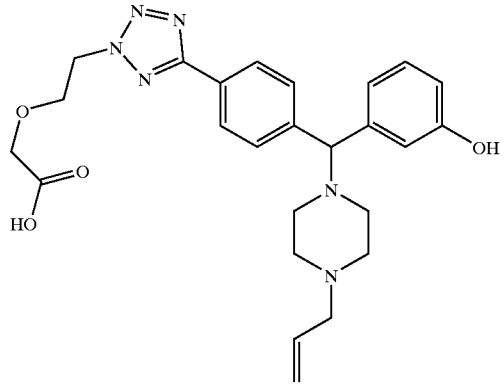

The title compound was prepared using the compound of Example 66, following a similar method to that described in Example 60, and was obtained as a white solid, in 63% yield.

m/z: 479 (MH$^+$). R$_f$: 0.2 (80/20/3 dichloromethane/methanol/ammonium hydroxide). $\delta_H$ (400 MHz, CDCl$_3$): 9.29 (1H, br.s), 7.94 (2H, d), 7.54 (2H, d), 7.06 (1H, dd), 6.81 (2H, m), 6.54 (1H, d), 5.75 (1H, m), 5.09 (2H, m), 4.86 (2H, t), 4.22 (1H, s), 4.00 (2H, t), 3.95 (2H, s), 3.54 (1H, s), 2.90 (2H, d), 2.34 (8H, m). Found: C, 59.42; H, 6.14; N, 16.31. $C_{25}H_{30}N_6O_4 \cdot 3/2H_2O$ requires C, 59.39; H, 6.58; N, 16.62%.

EXAMPLES 68 AND 69

(±)-Ethyl-4-(5-{4-[(R,S)-α-(4-Benzyl-1-piperazinyl)-3-hydroxybenzyl]phenyl}-1-tetrazolyl)butyrate and (±)-Ethyl 4-(5-{4-[(R,S)-α-(4-Benzyl-1-piperazinyl)-3-hydroxybenzyl]phenyl}-2-tetrazolyl)butyrate

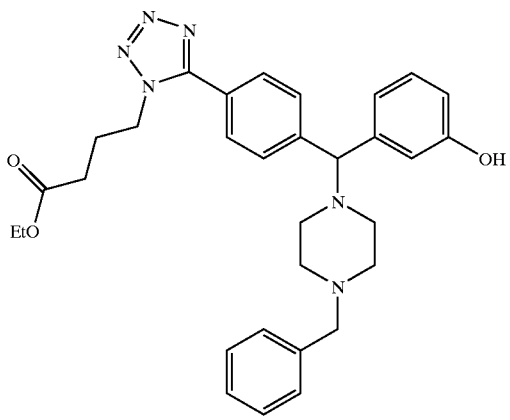

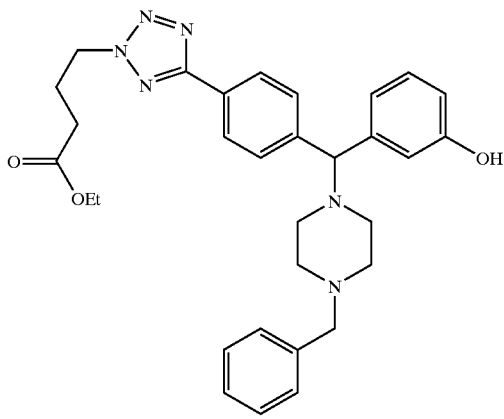

A suspension of the compound of Preparation 4b (1.62 g), potassium carbonate (1.25 g) and ethyl 4-bromobutyrate (430 μl) in acetonitrile (25 ml) was stirred under reflux for 18 hours. On cooling, the reaction mixture was concentrated in vacuo and the residue partitioned between ethyl acetate and water. The phases were separated, the aqueous layer extracted with further ethyl acetate, and the combined organic extracts dried (MgSO$_4$) and evaporated to dryness in vacuo, to give a yellow gum. Tetraethylammonium fluoride (0.8 g) was added to a solution of this material in tetrahydrofuran (20 ml) and the solution stirred at room temperature for 4 hours. The reaction mixture was concentrated in vacuo, and the residue partitioned between ethyl acetate and aqueous ammonium chloride solution. The phases were separated, the aqueous layer extracted with further ethyl acetate, and the combined organic extracts dried (MgSO$_4$), and evaporated to dryness in vacuo. The residue was purified by column chromatography over silica gel (50/50 ethyl acetate/hexane), to afford the N2 isomer, 1.02 g.

m/z: 542 (M2H$^+$). δ$_H$(400 MHz, DMSO-d$_6$): 9.29 (1H, s), 7.97 (2H, d), 7.55 (2H, d), 7.26 (5H, m), 7.06 (1H, dd), 6.68 (2H, m), 6.57 (1H, d), 4.74 (2H, t), 4.28 (1H, s), 4.02 (2H, q), 3.46 (2H, s), 2.30–2.48 (8H, m), 2.19 (2H, m), 1.14 (3H, t). followed by the N1 isomer, 0.14 g.

m/z: 542 (M2H$^+$). δ$_H$(400 MHz, DMSO-d$_6$): 9.30 (1H, s), 7.72 (2H, d), 7.62 (2H, d), 7.26 (5H, m), 7.07 (1H, dd), 6.84 (2H, m), 6.58 (1H, d), 4.48 (2H, t), 4.32 (1H, s), 3.92 (2H, q), 3.47 (2H, s), 2.22–2.44 (8H, m), 2.05 (2H, m), 1.08 (3H, t).

EXAMPLES 70 AND 71

(±)-Ethyl-5-(5-{4-[(R,S)-α-(4-Benzyl-1-piperazinyl)-3-hydroxybenzyl]phenyl}-1-tetrazolyl) valerate and (±)-Ethyl 5-(5-{4-[(R,S)-α-(4-Benzyl-1-piperazinyl)-3-hydroxybenzyl]-phenyl}-2-tetrazolyl) valerate

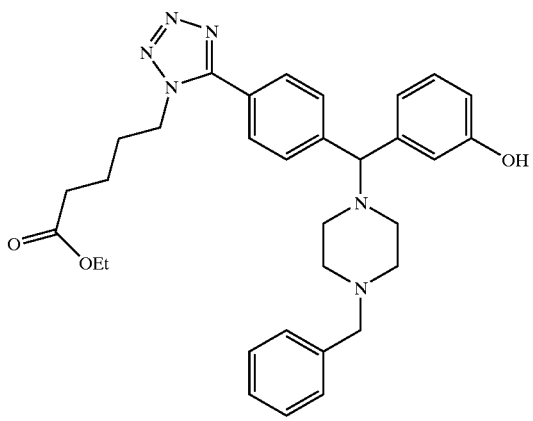

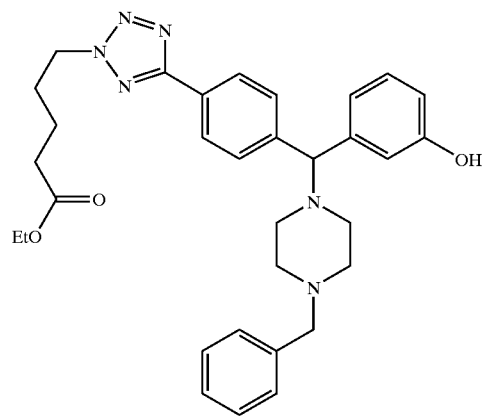

The title compounds were prepared following the procedure described in Example 68 and 69, using the compound of Preparation 4b, ethyl 5-bromovalerate, and were obtained in 10% and 56% yield respectively.

N1 isomer, m/z: 555 (MH$^+$). δ$_H$ (400 MHz, DMSO-d$_6$): 9.32 (1H, s), 7.72 (2H, d), 7.61 (2H, d), 7.28 (5H, m), 7.08 (1H, dd), 6.84 (2H, m), 6.58 (1H, d), 4.45 (2H, t), 4.30 (1H, s), 3.97 (2H, q), 3.47 (2H, s), 2.31–2.46 (8H, m), 2.23 (2H, t), 1.81 (2H, m), 1.46 (2H, m), 1.12 (3H, t).

and the N2 isomer. m/z: 555 (MH$^+$). δ$_H$ (400 MHz, DMSO-d$_6$): 9.29 (1H, s), 7.97 (2H, d), 7.56 (2H, d), 7.27 (5H, m), 7.06 (1H, dd), 6.83 (2H, m), 6.57 (1H, d), 4.70 (2H, t), 4.27 (1H, s), 4.03 (2H, q), 3.48 (2H, s), 2.26–2.48 (8H, m), 1.98 (2H, m), 1.52 (2H, m), 1.16 (3H, t).

EXAMPLE 72

(±)-(5-{4-[(R,S)-α-(4-Benzyl-1-piperazinyl)-3-hydroxybenzyl]phenyl}-2-tetrazolyl)acetic Acid

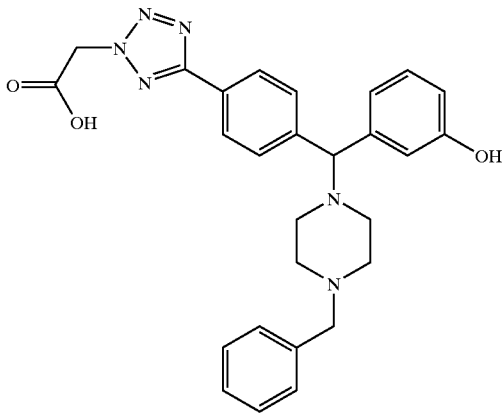

2N aqueous sodium hydroxide solution (1.05 ml) was added to a solution of the compound from Example 49 (540 mg) in methanol (15 ml), and the reaction stirred at room temperature for 2 hours. The reaction mixture was acidified to pH 6 using 2N hydrochloric acid and then evaporated to dryness in vacuo. The residue was purified by column chromatography over silica gel (80/20/3 dichloromethane/methanol/ammonium hydroxide) to afford the title compound as a colourless foam, 340 mg, m/z: 485 (MH$^+$). δ$_H$(300 MHz, DMSO-d$_6$): 7.97 (2H, d), 7.55 (2H, d), 7.30 (5H, m), 7.04 (1H, dd), 6.82 (2H, m), 6.56 (1H, d), 5.36 (2H, s), 4.28 (1H, s), 3.62 (2H, s), 2.30–2.62 (8H, m).

EXAMPLES 73 TO 76

The following compounds of the general formula:

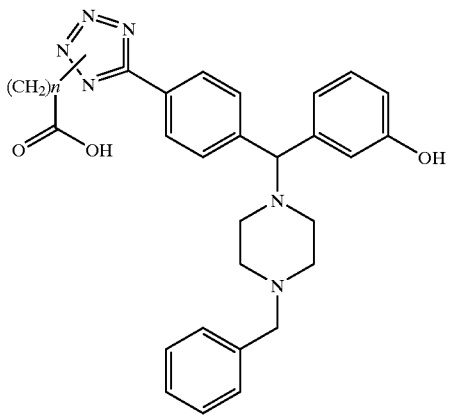

were prepared by hydrolysis of the corresponding esters, by similar methods to that used in Example 72

| Ex | Isomer | n | m/z | $^1$H-nmr |
|---|---|---|---|---|
| 73 | 1 | 3 | 513 | δ$_H$(400 MHz, DMSO-d$_6$): 7.74(2H, d), 7.62 (2H, d), 7.26(5H, m), 7.08(1H, dd), 6.85(2H, m), 6.58(1H, d), 4.48(2H, t), 4.30(1H, s), 3.48 (2H, s), 2.50(4H, m), 2.38(6H, m), 2.00(2H, m). |
| 74 | 2 | 3 | 513 | δ$_H$(400 MHz, DMSO-d$_6$): 7.98(2H, d), 7.55(2H, d), 7.27(5H, m), 7.07(1H, dd), 6.84(2H, m), 6.58(1H, d), 4.73(2H, t), 4.26(1H, s), 3.45(2H, s), 2.37(8H, m), 2.16(4H, m). |
| 75 | 1 | 4 | 527 | δ$_H$(300 MHz, DMSO-d$_6$): 7.70(2H, d), 7.60 (2H, d), 7.26(5H, m), 7.08(1H, dd), 6.83(2H, m), 6.57(1H, d), 4.43(2H, t), 4.30(1H, s), 3.45 (2H, s), 2.38(8H, m), 2.18(2H, t), 1.81(2H, m), 1.44(2H, m). |
| 76 | 2 | 4 | 527 | δ$_H$(300 MHz, DMSO-d$_6$): 7.84(2H, d), 7.52 (2H, d), 7.23(5H, m), 7.04(1H, dd), 6.90(2H, m), 6.54(1H, d), 4.68(2H, t), 4.24(1H, s), 3.43 (2H, s), 2.36(8H, m), 2.17(2H, t), 1.92(2H, m), 1.46(2H, m). |

Example 73. (±)-4-(5-{4-[(R,S)-α-(4-benzyl-1-piperazinyl)-3-hydroxybenzyl]phenyl}-1-tetrazolyl)butyric acid Example 74. (±)-4-(5-{4-[(R,S)-α-(4-benzyl-1-piperazinyl)-3-hydroxybenzyl]phenyl}-2-tetrazolyl)butyric acid Example 75. (±)-5-(5-{4-[(R,S)-α-(4-benzyl-1-piperazinyl)-3-hydroxybenzyl]phenyl}-1-tetrazolyl)valeric acid Example 76. (±)-5-(5-{4-[(RS)-α-(4-benzyl-1-piperazinyl)-3-hydroxybenzyl]phenyl}-2-tetrazolyl)valeric acid

EXAMPLE 77

(±)-2-(5-{4-[(R,S)-α-(4-Benzyl-1-piperazinyl)-3-hydroxybenzyl]phenyl}-1-tetrazolyl)ethoxyacetic Acid

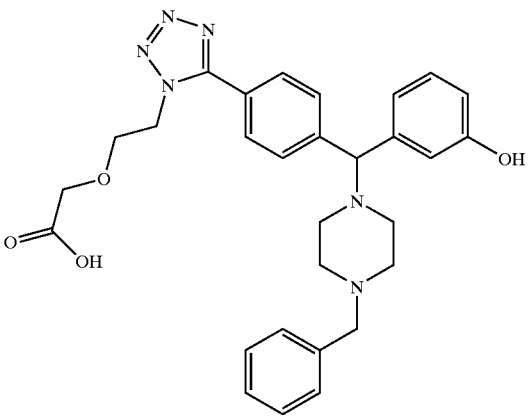

Hydrogen chloride gas was passed through a solution of the first compound in the drawings of Preparation 60 (180 mg) in ethanol (10 ml) and the reaction stirred at room temperature for an hour. The reaction mixture was then evaporated to dryness in vacuo, to give a colourless foam. This material was dissolved in aqueous ethanol (15 ml), sodium hydroxide (40 mg) added, and the reaction stirred at room temperature for 72 hours. The reaction mixture was acidified to pH 3.5 using 2N hydrochloric acid solution, rebasified with ammonium hydroxide solution, and the mixture evaporated to dryness in vacuo. The residue was purified by column chromatography over silica gel (80/20/3 dichloromethane/methanol/ammonium hydroxide) to afford the title compound as a colourless foam, 150 mg.

R$_f$: 0.37 (80/20/3 dichloromethane/methanol/ammonium hydroxide). δ$_H$ (400 MHz DMSO-d$_6$): 7.80 (2H, d), 7.58

(2H, d), 7.26 (5H, m), 7.05 (1H, dd), 6.82 (2H, m), 6.56 (1H, d), 4.56 (2H, t), 4.28 (1H, s), 3.86 (2H, t), 3.74 (2H, s), 3.46 (2H, s), 2.20–2.45 (8H, m).

EXAMPLE 78
(±)-2-(5-{4-[(R,S)-α-(4-Benzyl-1-piperazinyl)-3-hydroxybenzyl]phenyl}-2-tetrazolyl)ethoxyacetic Acid

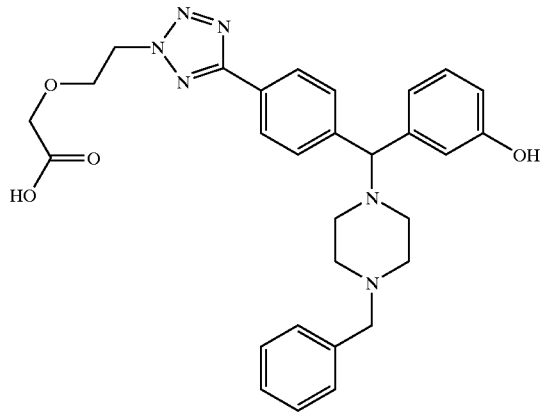

The title compound was prepared using the second compound in the drawings of Preparation 60, following the method described for Example 77, and was obtained as a colourless foam, (65%).

$R_F$: 0.34 (80/20/3 dichloromethane/methanol/ammonium hydroxide). $\delta_H$ (400 MHz, DMSO-$d_6$): 7.97 (2H, d), 7.55 (2H, d), 7.26 (5H, m), 7.05 (1H, dd), 6.82 (2H, m), 6.55 (1H, d), 4.85 (2H, t), 4.24 (1H, s), 4.00 (2H, t), 3.80 (2H, s), 3.45 (2H, s), 2.20–2.45 (8H, m).

EXAMPLES 79 TO 82

The following compounds of the general formula:

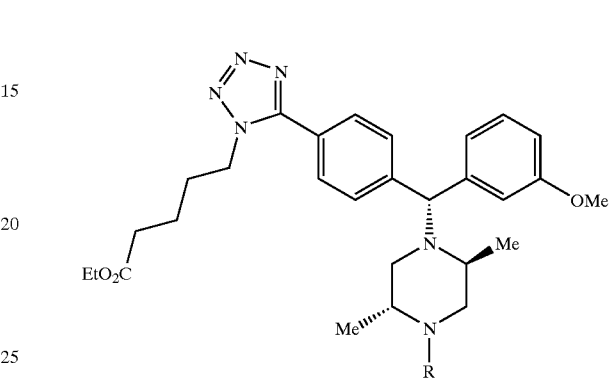

were prepared from the corresponding amides (Preparations 62 to 65) by similar methods to that described for Example 53.

| Ex | R | m/z (MH+) | nmr |
|---|---|---|---|
| 79 | *—CH₂CH₂—Me (propyl) | 549 | $\delta_H$(400 MHz, CDCl₃): 7.68 (2H, d), 7.60 (2H, d), 7.26 (1H, m), 6.90-6.72 (3H, m), 5.24 (1H, s), 4.42 (2H, m), 4.12 (2H, m), 3.80 (3H, s), 2.88 (1H, d), 2.76-2.46 (4H, m), 2.34 (2H, t), 2.20 (2H, m), 2.02 (2H, m), 1.94 (1H, m), 1.76-1.40 (4H, m), 1.30-1.20 (6H, m), 1.00 (3H, d), 0.90 (3H, t). |
| 80 | *—CH₂CH₂CH₂—Me (butyl) | 563 | $\delta_H$(400 MHz, CDCl₃): 7.66 (2H, d), 7.60 (2H, d), 7.24 (1H, m), 6.88-6.72 (3H, m), 5.24 (1H, s), 4.42 (2H, m), 4.12 (2H, m), 3.80 (3H, s), 2.86 (1H, d), 2.72-2.42 (4H, m), 2.38-1.88 (7H, m), 1.68 (2H, m), 1.42 (2H, m), 1.38-1.08 (8H, m), 1.00 (3H, d), 0.92 (3H, t). |
| 81 | *—CH₂—cyclopropyl | 561 | $\delta_H$(400 MHz, DMSO-$d_6$): 7.72 (2H, d), 7.60 (2H, d), 7.28 (1H, m), 6.86 (3H, m), 5.18 (1H, br s), 4.46 (2H, t), 4.00 (2H, q), 3.74 (3H, s), 2.90 (1H, d), 2.60 (3H, m), 2.40-2.10 (4H, m), 1.80 (3H, m), 1.40 (2H, m), 1.20-1.10 (6H, m), 0.90 (3H, d), 0.76 (1H, m), 0.40 (2H, m), 0.02 (2H, m). |
| 82 | *—CH₂CH(Me)—Me (isobutyl) | 563 | $\delta_H$(400 MHz, DMSO-$d_6$): 7.72 (2H, d), 7.62 (2H, d), 7.24 (1H, t), 6.98-6.80 (3H, m), 5.02 (1H, br s), 4.44 (2H, t), 3.98 (2H, q), 3.72 (3H, s), 2.80 (1H, d), 2.70-2.50 (4H, m), 2.38-1.40 (11H, m), 1.20-1.06 (5H, m), 0.96 (3H, d), 0.82 (3H, d), 0.78 (3H, d). |

Example 79: Ethyl 5-(5-{4-[(R)-α-(2(S),5(R)-4-propyl-2,5-dimethyl-1-piperazinyl)-3-methoxybenzyl]phenyl}-1-tetrazolyl)valerate.

Example 80: Ethyl 5-(5-{4-[(R)-α-(2(S),5(R)-4-butyl-2,5-dimethyl-1-piperazinyl)-3-methoxybenzyl]phenyl}-1-tetrazolyl)valerate.

Example 81: Ethyl 5-(5-{4-[(R)-α-(2(S),5(R)-4-cyclopropylmethyl-2,5-dimethyl-1-piperazinyl)-3-methoxybenzyl]phenyl}-1-tetrazolyl)valerate.

Example 82: Ethyl 5-(5-{4-[(R)-α-(2(S),5(R)-4-iso-butyl-2,5-dimethyl-1-piperazinyl)-3-methoxybenzyl]phenyl}-1-tetrazolyl)valerate.

EXAMPLES 83 TO 86

The following compounds of the general formula:

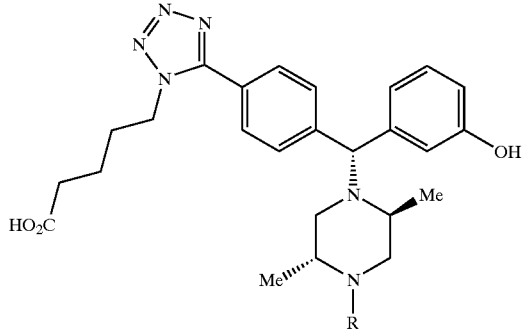

were prepared from the corresponding esters (Examples 79 to 82) by similar methods to that described for Example 36.

| Ex | R | m/z (MH⁺) | Data |
|----|---|-----------|------|
| 83 | *–CH₂–CH₂–Me | 507 | $\delta_H$ (400 MHz, DMSO-$d_6$): 7.72 (2H, d), 7.60 (2H, d), 7.12 (1H, m), 6.80-6.60 (3H, m), 5.04 (1H, br s), 4.44 (2H, t), 3.36 (2H, br s), 2.80 (1H, d), 2.70-2.40 (6H, m), 2.20-2.06 (3H, m), 1.84 (2H, m), 1.46 (2H, m), 1.38 (2H, m), 1.10 (3H, d), 0.94 (3H,d), 0.80 (3H, t). m/z: 507 (MH⁺) Found: C, 64.10; H, 7.34; N, 16.06. $C_{28}H_{38}N_6O_3 \cdot H_2O$ requires C, 64.10; H, 7.68; N, 16.02% $[\alpha]_D + 18.9°$ (c = 0.13, methanol) |
| 84 | *–CH₂–CH₂–CH₂–Me | 521 | $\delta_H$ (400 MHz, DMSO-$d_6$): 7.72 (2H, d), 7.60 (2H, d), 7.14 (1H, t), 6.80-6.60 (3H, m), 5.02 (1H, s), 4.48 (2H, t), 3.30 (2H, br s), 2.80 (1H, d), 2.70-2.40 (4H, m), 2.24-2.02 (4H, m), 1.86 (3H, m), 1.46 (2H, m), 1.36 (2H, m), 1.24 (2H, m), 1.08 (3H, d), 0.96 (3H, t), 0.84 (3H, t). m/z: 521 (MH⁺) Found: C, 65.70; H, 7.90; N, 16.00. $C_{29}H_{40}N_6O_3 \cdot 0.5H_2O$ requires C, 65.76; H, 7.80; N, 15.87% $[\alpha]_D + 14.5°$ (c = 0.12, methanol) |
| 85 | *–CH₂–cyclopropyl | 519 | $\delta_H$ (400 MHz, DMSO-$d_6$): 7.72 (2H, d), 7.60 (2H, d), 7.14 (1H, m), 6.76-6.60 (3H, m), 5.10 (1H, br s), 4.44 (2H, t), 3.30 (2H, br s), 2.92 (1H, d), 2.70-2.00 (8H, m), 1.80 (3H, m), 1.42 (2H, m), 1.12 (3H, d), 0.90 (3H, d), 0.76 (1H, m), 0.40 (2H, m), 0.02 (2H, m). m/z: 519 (MH⁺) Found: C, 64.34; H, 7.10; N, 15.42. $C_{29}H_{38}N_6O_3 \cdot 1.25H_2O$ requires C, 64.36; H, 7.54; N, 15.53% |
| 86 | *–CH₂–CH(Me)–Me | 521 | $\delta_H$ (400 MHz, DMSO-$d_6$): 7.70 (2H, d), 7.60 (2H, d), 7.10 (1H, t), 6.80-6.60 (3H, m), 4.96 (1H, br s), 4.44 (2H, t), 3.30 (2H, br s), 2.80 (1H, d), 2.66 (1H, m), 2.58 (1H, m), 2.30-2.10 (3H, m), 2.02 (1H, m), 1.94-1.76 (4H, m), 1.64 (1H, m), 1.42 (3H, m), 1.10 (3H, d), 0.96 (3H, d), 0.94 (3H, d), 0.82 (3H, d), 0.78 (3H, d). m/z: 521 (MH⁺) Found: C, 64.70; H, 7.46; N, 15.43. $C_{29}H_{40}N_6O_3 \cdot 1.0H_2O$ requires C, 64.66; H, 7.86; N, 15.60% |

Example 83: (+)-5-(5-{4-[(R)-α-(2(S),5(R)-4-propyl-2,5-dimethyl-1-piperazinyl)-3-hydroxybenzyl]phenyl}-1-tetrazolyl)valeric acid.

Example 84: (+)-5-(5-{4-[(R)-α-(2(S),5(R)-4-butyl-2,5-dimethyl-1-piperazinyl)-3-hydroxybenzyl]phenyl}-1-tetrazolyl)valeric acid.

Example 85: 5-(5-{4-[(R)-α-(2(S),5(R)-4-cyclopropylmethyl-2,5-dimethyl-1-piperazinyl)-3-hydroxybenzyl]phenyl }-1-tetrazolyl)valeric acid.

Example 86: 5-(5-{4-[(R)-α-(2(S),5(R)-4-iso-butyl-2,5-dimethyl-1-piperazinyl)-3-hydroxybenzyl]phenyl}-1-tetrazolyl)valeric acid.

EXAMPLE 87

5-(5-{4-[(R)-α-(2(S),5(R)-2,5-Dimethyl-1-piperazinyl)-3-hydroxybenzyl]phenyl}-2-tetrazolyl)valeric Acid

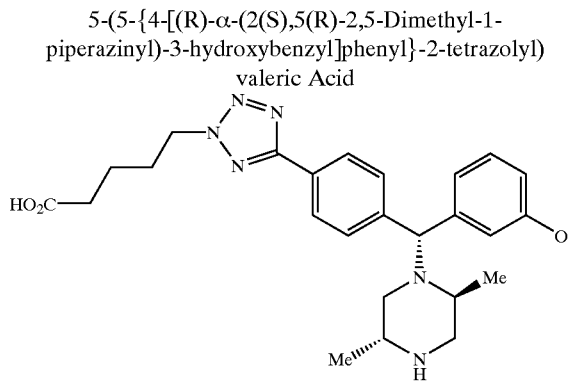

Tris(triphenylphosphine)rhodium(I) chloride (200 mg) was added to a solution of the compound of Example 42 (500 mg) in acetonitrile (160 ml) and water (40 ml). The reaction mixture was heated under a gentle reflux and the solvent allowed to distil off slowly. Additional acetonitrile/water (200 ml; 4:1 v/v) was added at such a rate as to maintain a steady distillation. After the addition of solvent was complete the distillation was continued until the volume was reduced to approximately 60 ml. The cooled solution was poured into ethyl acetate and washed with saturated aqueous sodium bicarbonate solution and saturated brine. The solution was dried (magnesium sulphate), evaporated to dryness in vacuo and the residue was purified by column chromatography over silica gel (70/30/4 dichloromethane/methanol/ammonium hydroxide) to afford the title compound, 360 mg.

m/z: 465 (MH$^+$). R$_f$: 0.09 (80/20/3 dichloromethane/methanol/ammonium hydroxide). δ$_H$ (400 MHz, DMSO-d$_6$): 7.98 (2H d), 7.50 (2H, d), 7.16 (1H, t), 6.74–6.50 (3H, m), 5.26 (1H, s), 4.70 (2H, t), 3.30 (2H, br), 2.84 (1H, d), 2.60–2.18 (4H, m), 1.96 (1H, m), 1.66–1.40 (3H, m), 1.10 (3H, d), 0.86 (3H, d). m/z: 465 (MH$^+$) Found: C, 62.71; H, 7.14; N, 16.95. C$_{25}$H$_{32}$N$_6$O$_3$·1.0H$_2$O requires C, 62.22; H, 7.10; N, 17.41%.

EXAMPLE 88

(+)-5-(5-{4-[(R)-α-(2(S),5(R)-4-Propyl-2,5-dimethyl-piperazinyl)-3-hydroxybenzyl]phenyl}-2-tetrazolyl)valeric Acid

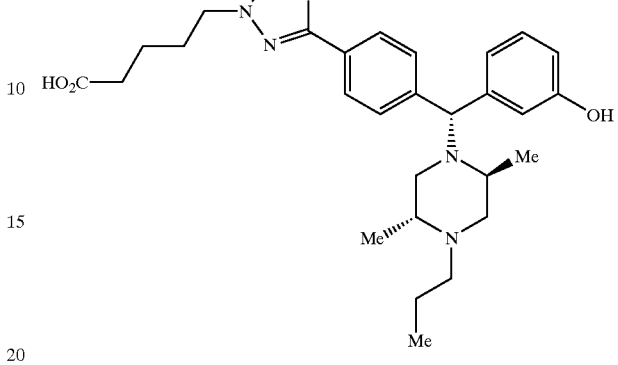

To a solution of the compound of Example 87 (350 mg), propionaldehyde (102 μl) and glacial acetic acid (53 μl) in dry dimethylformamide (20 ml) was added, with stirring, sodium triacetoxyborohydride (486 mg). The resulting mixture was stirred at room temperature for 18 hours after which time it was evaporated to dryness in vacuo. The residue was purified by column chromatography over silica gel (80/20/3 dichloromethane/methanol) to afford the title compound as beige solid. The compound was further purified over reverse phase polystyrene resin (100% water to 100% acetonitrile in 10% increments) to afford, after freeze-drying, the title compound as a flocculant white powder, 273 mg.

m/z: 507 (MH$^+$). R$_f$: 0.18 (80/20/3 dichloromethane/methanol/ammonium hydroxide). δ$_H$ (400 MHz, DMSO-d$_6$): 7.97 (2H, d), 7.56 (2H, d), 7.12 (1H, t), 6.74–6.50 (3H, m), 4.95 (1H, s), 4.70 (2H, t), 2.77 (1H, d), 2.68–2.37 (4H, m), 2.21 (2H, t), 2.08 (2H, m), 1.90 (3H, m), 1.49 (2H, m), 1.35 (2H, m), 1.08 (3H, d), 0.90 (3H, d), 0.80 (3H, d). Found: C, 64.17; H, 7.63; N, 16.07. C$_{28}$H$_{38}$N$_6$O$_3$·1.0H$_2$O requires C, 64.10; H, 7.68; N, 16.02%. [α]$_D$+1 7.6° (c=0.106, methanol).

EXAMPLES 89 AND 90

Methyl (5-{4-[(R)-α-(2(S),5(R)-4-Allyl-2,5-dimethyl-1-piperazinyl)-3-hydroxybenzyl]phenyl}-2-tetrazolyl)-4-methylbenzoate and Methyl (5-{4-[(R)-α-(2(S),5(R)-4-Allyl-2,5-dimethyl-1-piperazinyl)-3-hydroxybenzyl]phenyl}-1-tetrazolyl)-4-methylbenzoate

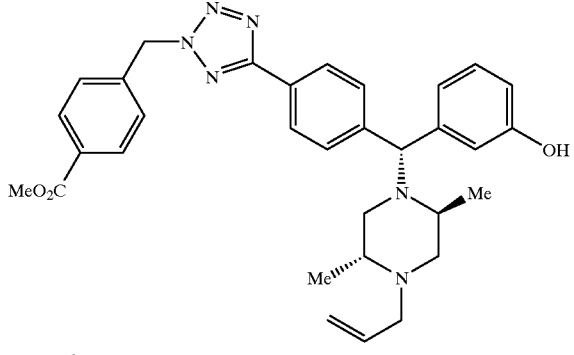

and

-continued

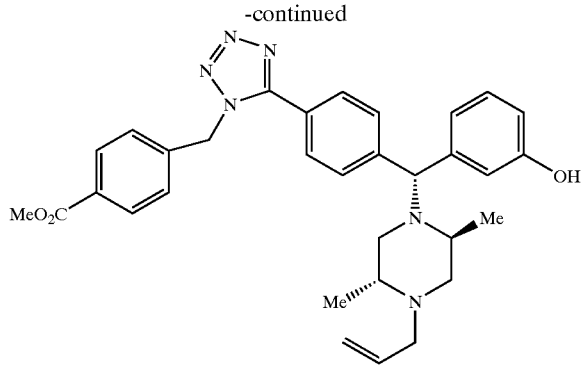

A solution of the compound of Preparation 31 (1.07 g), potassium carbonate (855 mg) and methyl 4-(bromomethyl) benzoate (544 mg) in dry acetonitrile (15 ml) was heated under reflux for 18 hours. To the cooled mixture was added tetraethylammonium fluoride (462 mg) and the resulting mixture stirred for 30 minutes and the concentrated to a volume of 3 ml in vacuo. The residue was partitioned between ethyl acetate and 2% aqueous sodium hydrogen carbonate solution, and the layers separated. The aqueous phase was extracted with further ethyl acetate and the combined organics dried (magnesium sulphate) and evaporated to dryness in vacuo. The residue was purified by column chromatography over silica gel using gradient elution (85/15/1 to 80/20/1.5 pentane/isopropanol/armnonium hydroxide) to afford the N-2 isomer, 605 mg.

$R_f$: 0.21(85/15/1 pentane/isopropanol/ammonium hydroxide). $\delta_H$ (300 MHz, CDCl$_3$): 8.00 (2H, d), 7.57 (2H, d), 7.43 (1H, m), 6.80–6.60 (3H, m), 5.98–5.80 (1H, m), 5.25–5.05 (3H, m), 4.95 (1H, s), 3.90 (3H, s), 3.43–3.33 (1H, m), 3.00–2.43 (5H, m), 2.23–2.03 (1H, m), 2.02–1.93 (1H, m), 1.17 (3H, d), 1.00 (3H, d).

followed by the N-1 isomer, 160 mg. $R_f$: 0.10 (85/15/1 pentane/isopropanol/ammonium hydroxide). $\delta_H$ (300 MHz, CDCl$_3$): 7.98 (2H, d), 7.53 (2H, d), 7.43 (1H, m), 7.23–7.10 (3H, m), 6.73 (2H, m), 6.57 (1H, s), 5.93–5.77 (1H, m), 5.25–5.05 (3H, m), 4.95 (1H, s), 3.90 (3H, s), 3.43–3.33 (1H, m), 3.00–2.43 (5H, m), 2.23–2.03 (1H, m), 2.02–1.93 (1H, m), 1.17 (3H, d), 1.00 (3H, d).

EXAMPLE 91

Methyl (5-{4-[(R)-α-(2(S),5(R)-2,5-Dimethyl-1-piperazinyl)-3-hydroxybenzyl]phenyl}-2-tetrazolyl)-4-methylbenzoate The compound of the following formula:

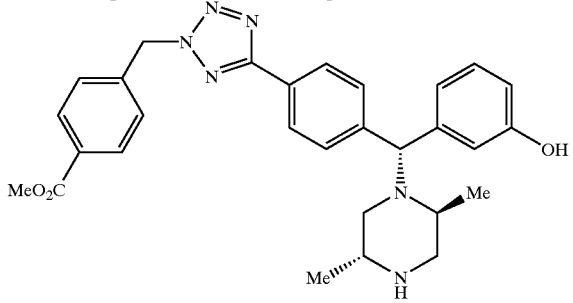

was prepared by a similar method to that described for Preparation 61 using the compound of Example 89.

Rf: 0.08 (9/1; dichloromethane/methanol). $\delta_H$ (400 MHz, CDCl$_3$): 8.00 (4H, m), 7.63 (1H, m), 7.55–7.35 (4H, m), 7.15 (1H, m), 6.67–6.63 (2H, m), 6.60 (1H, s), 5.80 (2H, m), 5.25 (1H, m), 3.88 (3H, s), 2.90 (2H, m), 2.63 (2H, m), 2.43 (1H, br s), 2.00 (1H, m), 1.65 (1H, m), 1.10 (3H, d), 0.90 (3H, d).

EXAMPLE 92

Methyl (5-{4-[(R)-α-(2(S),5(R)-2,5-Dimethyl-1-piperazinyl)-3-hydroxybenzyl]phenyl}-1-tetrazolyl)-4-methylbenzoate The compound of the following formula:

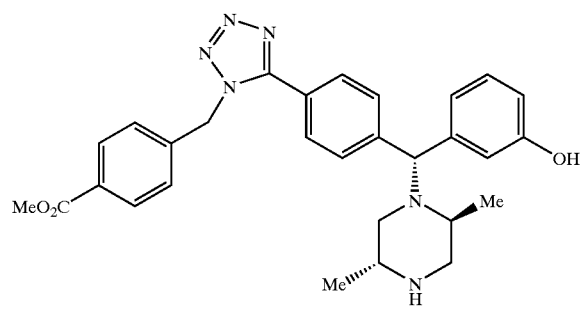

was prepared by a similar method to that described for Preparation 61 using the compound of Example 90.

Rf: 0.05 (9/1; dichloromethane/methanol). $\delta_H$ (400 MHz, CDCl$_3$): 7.97 (2H, m), 7.67 (2H, m), 7.57–7.38 (4H, m), 7.15 (1H, m), 6.78 (1H, m), 6.65 (1H, m), 6.52 (1H, br s), 5.65 (2H, s), 5.28 (1H, m), 3.90 (3H, s), 2.90 (2H, m), 2.67 (1H, m), 2.53 (1H, m), 2.38 (1H, br s), 1.97 (1H, m), 1.62 (1H, m), 1.13 (3H, d), 0.93 (3H, d).

EXAMPLE 93

Methyl (5-{4-[(R)-α-(2(S),5(R)-4-Benzyl-2,5-dimethyl-1-piperazinyl-3-hydroxybenzyl]phenyl}-2-tetrazolyl)-4-methylbenzoate The compound of the following formula:

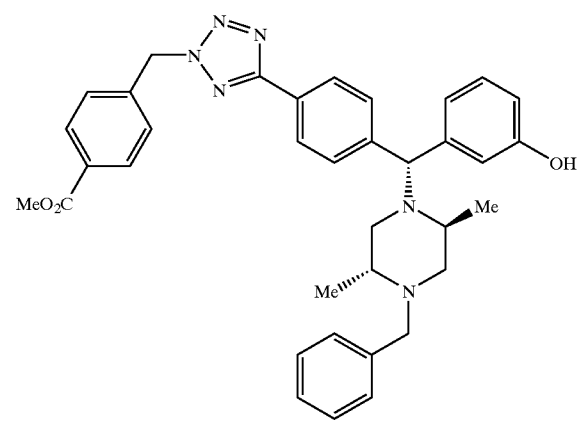

was prepared by reductive alkylation of the compound of Example 91 with benzaldehyde using a method similar to that described for Preparation 8.

Rf: 0.27 (96/4; dichloromethane/methanol). $\delta_H$ (400 MHz, CDCl$_3$): 8.07 (4H, mn), 7.53 (2H, m), 7.43 (2H, m), 7.35–7.10 (6H, m), 6.83–6.65 (3H, m), 5.83 (2H, s), 5.10 (1H, m), 4.83 (1H, br s), 3.90 (3H, s), 3.87 (1H, br d), 3.23 (1H, br d), 2.77–2.50 (4H, m), 2.08–1.93 (2H, m), 1.10 (6H, m).

EXAMPLE 94

(5-{4-[(R)-α-(2(S),5(R)-4-Benzyl-2,5-dimethyl-1-piperazinyl)-3-hydroxybenzyl]phenyl}-2-tetrazolyl)-4-methylbenzcic Acid The compound of the following formula:

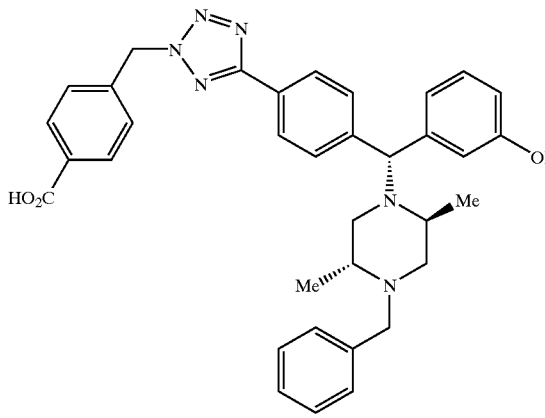

was prepared by hydrolysis of the compound of Example 93 using a method similar to that described for Example 19.

Rf: 0.40 (76/20/4; dichloromethane/methanol/ammonium hydroxide). m/z: 589 (MH$^+$). $\delta_H$ (400 MHz, DMSO-d$_6$): 8.00–7.85 (4H, m), 7.50 (2H, m), 7.38 (2H, m), 7.30–7.03 (6H, m), 6.77–6.60 (3H, m), 6.02 (2H, s), 4.95 (1H, m), 3.75 (1H, br d), 3.27 (1H, br d), 2.73–2.27 (4H, m), 2.03–1.87 (2H, m), 1.00 (6H, m). Found: C, 66.86; H, 6.06; N, 13.12. C$_{35}$H$_{36}$N$_6$O$_3$.2.25H$_2$O requires C, 66.80; H, 6.49; N, 13.35%.

EXAMPLE 95

Methyl (5-{4-[(R)-α-(2(S),5(R)-4-Benzyl-2,5-dimethyl-1-piperazinyl)-3-hydroxybenzyl]phenyl}-1-tetrazolyl)-4-methylbenzoate The compound of the following formula:

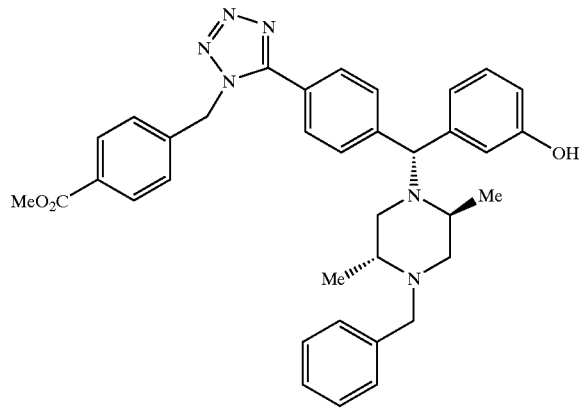

was prepared by reductive alkylation of the compound of Example 92 with benzaldehyde using a method similar to that described for Preparation 8.

Rf: 0.15 (4/5; ethyl acetate/pentane).

EXAMPLE 96

(5-{4-[(R)-α-(2(S),5(R)-4-Benzyl-2,5-dimethyl-1-piperazinyl)-3-hydroxybenzyl]phenyl}-1-tetrazolyl)-4-methylbenzoic Acid The compound of the following formula:

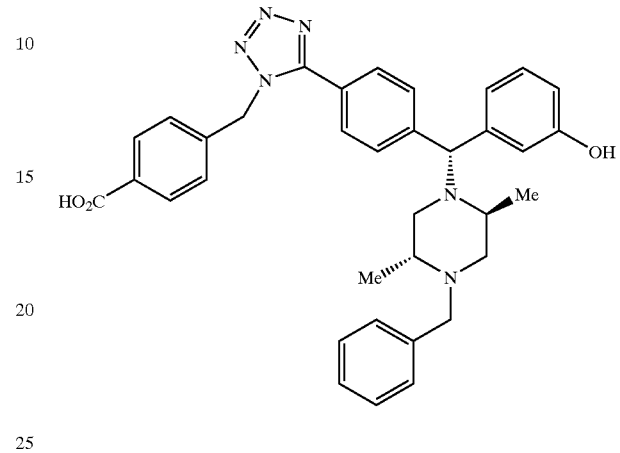

was prepared by hydrolysis of the compound of Example 95 using a method similar to that described for Example 19.

m/z: 589 (MH$^+$). $\delta_H$ (300 MHz, DMSO-d$_6$): 9.33 (1H, s), 7.93 (2H m), 7.70–7.03 (12H, m), 6.65 (3H, m), 5.85 (2H, s), 5.00 (1H, br m), 3.80 (1H, m), 3.20 (1H, ), 2.17–1.80 (6H, m), 1.08 (6H, m). Found: C, 67.73; H, 6.23; N, 12.94. C$_{35}$H$_{36}$N$_6$O$_3$.2.0H$_2$O requires C, 67.28; H, 6.45; N, 13.45%.

EXAMPLE 97

Ethyl 5-(5-{4-[(R)-α-(2(S)-4-Benzyl-2-methyl-1-piperazinyl)-3-hydroxybenzyl]phenyl}-2-tetrazolyl) valerate The compound of the following formula:

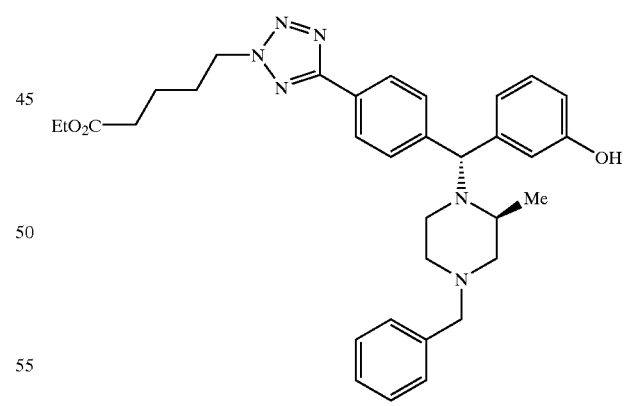

was prepared using a method similar to that described for Example 42 using the compounds of Preparations 43, 44 and 66.

R$_f$: 0.4 (1/1; ethyl acetate/pentane). $\delta_H$ (400 MHz, CDCl$_3$): 8.02 (2H, d), 7.55 (2H, d), 7.30–7.20 (5H, m), 7.12 (1H, m), 6.88 (1H, m), 6.78 (1H, s), 6.63 (1H, m), 4.85 (1H, br s), 4.64 (2H, t), 4.12 (2H, q), 3.47 (2H, q), 2.87 (1H, br s), 2.65–2.30 (8H, m), 2.06 (2H, m), 1.69 (2H, m), 1.24 (3H, t), 1.11 (3H, d).

EXAMPLE 98

(+)-5-(5-{4-[(R)-α-(2(S)-4-Benzyl-2-methyl-1-piperazinyl)-3-hydroxybenzyl]phenyl}-2-tetrazolyl) valeric Acid The compound of the following formula:

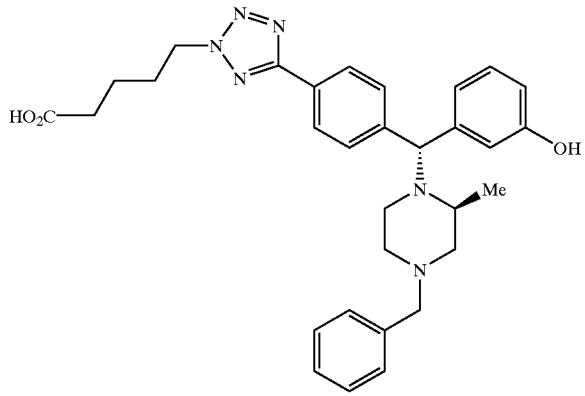

was prepared by hydrolysis of the compound of Example 97 using a method similar to that described for Example 19.

R$_f$: 0.25 (80/20/4; dichloromethane/methanol/ammonium hydroxide). m/z: 542 (MH$^+$). δ$_H$ (400 MHz, DMSO-d$_6$): 7.94 (2H, d), 7.56 (2H, d), 7.35–7.15 (5H, m), 7.05 (1H, dd), 6.80 (2H, m), 6.57 (1H, m), 4.64 (3H, m), 3.40 (2H, m), 2.84 (1H, m), 2.60–2.20 (6H, m), 1.91 (4H, m), 1.40 (2H, t), 1.02 (3H, d). Found: C, 63.09; H, 6.58; N, 14.14. C$_{31}$H$_{36}$N$_6$O$_3$.2.75H$_2$O requires C, 63.03; H, 7.09; N, 14.24%. [α]$_D$+31° (c=0.1, methanol).

EXAMPLE 99

(+)-3-{5-[(R)-α-(2(S),5(R)-4-Allyl-2,5-dimethyl-1-piperazinyl)-3-hydroxybenzyl]tetrazolyl}benzene The compound of the following formula:

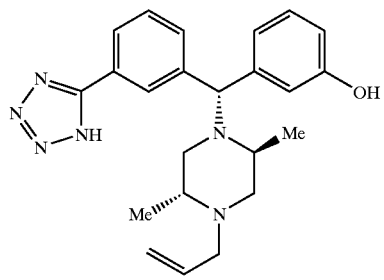

was prepared by desilylation of the compound of Preparation 33 using a method similar to that described for Example 55.

R$_f$: 0.23 (80/20/3; dichloromethane/methanol/ammonium hydroxide). m/z: 405 (MH$^+$). δ$_H$ (400 MHz, DMSO-d$_6$): 9.35 (1H, br s), 8.16 (1H, s), 7.82 (1H, m), 7.42 (1H, m), 7.13 (1H, t), 6.73 (2H, m), 6.66 (1H, m), 5.82 (1H, m), 5.25 (2H, m), 5.02 (1H, br s), 3.38–3.13 (4H, m), 2.93 (1H, m), 2.82 (1H, m), 2.68 (2H, m), 2.39 (1H, m), 2.0 (1H, m), 1.10 (3H, d), 1.04 (3H, d). [α]$_D$+25.1° (c=0.11, methanol).

EXAMPLE 100

Preparation of the Benzathine Salt of Compound of Example 42

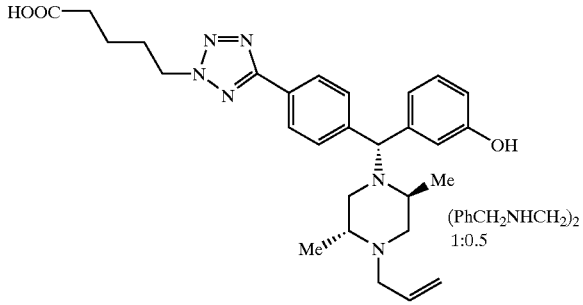

N,N-Dibenzylethylenediamine (1.19 g, 4.96 mmol), the compound of Example 42 (5 g, 9.91 mmol) and 5% v/v water in methyl ethyl ketone (12 ml) were heated at reflux. The clear mixture was allowed to cool to room temperature, and stirred for 48 hours. The white crystalline suspension was filtered off and washed with cold solvent (3.1 ml), and dried under vacuum at room temperature for 18 hours. Yield 3.46 g (55%) of the salt as a white solid with a sharp melting point of 139° C.

HPLC analysis shows there to be 19.7% N,N dibenzyl-ethylenediamine and 80% compound of Example 42 to be present by total area analysis. Water is present at 0.3%. This gives a stoichiometric ratio of compound to base of 1:0.5.

Molecular Formula C$_{36.3}$H$_{46.6}$N$_{7.0}$O$_{3.1}$. C,H, N Theoretical % C, 69.14; % H, 7.45; % N, 15.55. Actual % C,68.90; % H, 7.92; % N, 15.56.

EXAMPLES 101–103

The following compounds of the general formula:

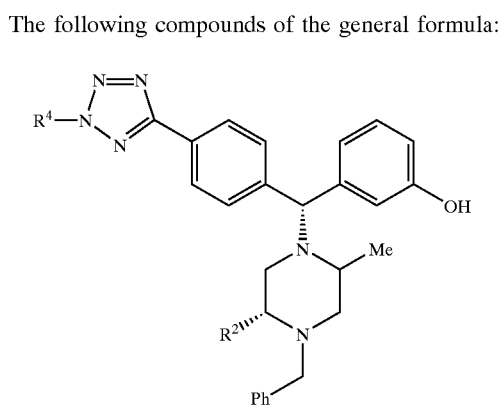

were prepared by a similar method to that described for Preparation 5 using the corresponding aldehydes (Preparations 67, 69, and 70) and the corresponding piperazine derivatives (either Preparation 26 or Preparation 66).

| Ex | R² | R⁴ | Data |
|---|---|---|---|
| 101 | Me | 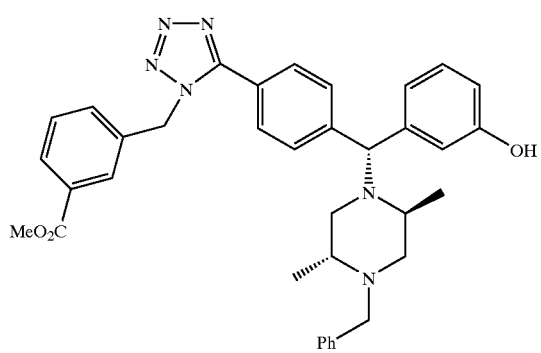 benzyl with 3-CO₂Me | R_f: 0.42 (dichloromethane/methanol; 95:5) m/z: 603 (MH⁺) δ_H (300 MHz, CDCl₃): 8.12 (1H, s), 8.03 (3H, m), 7.57 (3H, m), 7.48 (1H, t), 7.22 (6H, m), 6.78 (1H, d), 6.68 (2H, m), 5.82 (2H, s), 5.08 (2H, br s), 3.90 (4H, m), 3.20 (1H, d), 2.73 (1H, m), 2.60 (3H, m), 2.02 (2H, m), 1.08 (6H, m). |
| 102 | H | *—CH₂CH₂—CO₂Et | R_f: 0.12 (ethyl acetate/pentane; 1:2) δ_H (300 MHz, CDCl₃): 8.02 (1H, s), 7.57 (2H, d), 7.25 (5H, m), 7.15 (1H, t), 6.88 (1H, d), 6.80 (1H, s), 6.63 (1H, m), 4.93 (2H, t), 4.85 (1H, s), 3.47 (2H, m), 3.10 (2H, t), 2.88 (1H, m), 2.65-2.30 (6H, m), 1.22 (3H, t), 1.12 (3H, d). |
| 103 | H | *—CH₂CH₂CH₂—CO₂Me | R_f: 0.28 (ethyl acetate/pentane; 1:2) δ_H (300 MHz, CDCl₃): 8.02 (1H, s), 7.58 (2H, d), 7.32-7.10 (6H, m), 6.90 (1H, d), 6.81 (1H, m), 6.63 (1H, m), 4.85 (1H, s), 4.72 (2H, t), 3.68 (3H, s), 3.56-3.40 (2H, m), 2.88 (1H, m), 2.65-2.30 (6H, m), 1.12 (3H, d). |

Example 101: Methyl (5-{4-[(R)-α-(2(S),5(R)-4-benzyl-2,5-dimethyl-1-piperazinyl)-3-hydroxybenzyl]phenyl}-2-tetrazolyl)-3-methylbenzoate.

Example 102: Ethyl 3-(5-{4-[(R)-α-(2(S)-4-benzyl-2-methyl-1-piperazinyl)-3-hydroxybenzyl]phenyl}-2-tetrazolyl)propionate.

Example 103: Methyl 4-(5-{4-[(R)-α-(2(S)-4-benzyl-2-methyl-1-piperazinyl)-3-hydroxybenzyl]phenyl}-2-tetrazolyl)butanoate.

EXAMPLE 104

Methyl (5-{4-[(R)-α-(2(S),5(R)-4-Benzyl-2,5-dimethyl-1-piperazinyl)-3-hydroxybenzyl]phenyl}-1-tetrazolyl)-3-methylbenzoate The compound of the following formula:

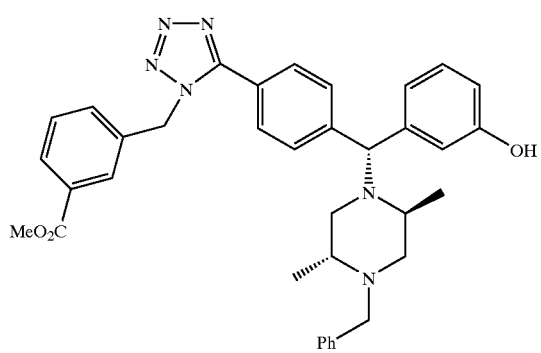

was prepared using a similar method to that described for Preparation 5 using the compounds of Preparations 26, 44 and 68.

R_f: 0.31 (dichloromethane/methanol/ammonium hydroxide; 95/5/0.5). m/z: 603 (MH⁺).

EXAMPLES 105–107

The following compounds of the general formula:

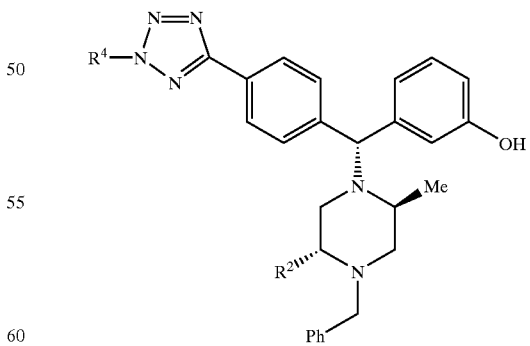

were prepared by hydrolysis of the corresponding esters using a method similar to that described for Example 19.

| Ex | R² | R⁴ | Data |
|---|---|---|---|
| 105 | Me | 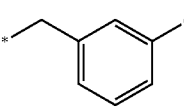 | $R_f$: 0.22 (dichloromethane/methanol/ammonium hydroxide; 80/20/3)<br>m/z: 589 (MH⁺)<br>$\delta_H$ (300 MHz, $d_6$-DMSO): 8.00-7.84 (4H, m), 7.59-7.40 (4H, m), 7.30-7.08 (6H, m), 6.70 (3H, m), 6.03 (3H, m), 4.97 (1H, s), 3.75 (1h, d), 3.25 (1H, d), 2.60 (4H, m), 1.97 (2H, m), 1.02 (6H, m).<br>Found: C, 67.88; H, 5.89; N, 13.57. $C_{35}H_{36}N_6O_3 \cdot 3/2H_2O$ requires C, 68.27; H, 6.38; N, 13.65% |
| 106 | H | 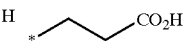 | $R_f$: 0.05 (ethyl acetate/methanol/triethylamine; 78.5/20/15)<br>m/z: 513 (MH⁺)<br>$\delta_H$ (300 MHz, $d_6$-DMSO): 9.29 (1H, s), 7.95 (2H, d), 7.58 (2H, d), 7.32-7.19 (5H, m), 7.07 (1H, t), 6.88-6.79 (2H, m), 6.59 (1H, d), 4.88 (2H, t), 4.75 (1H, s), 3.55-3.21 (2H, m), 305 (2H, t), 2.88 (2H, t), 2.60-2.20 (6H, m), 1.03 (3H, t). |
| 107 | H | 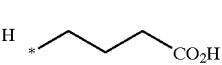 | $R_f$: 0.25 (dichloromethane/methanol/ammonium hydroxide; 80/20/4)<br>m/z: 527 (MH⁺)<br>$\delta_H$ (300 MHz, $d_6$-DMSO): 7.97 (2H, d), 7.58 (2H, d), 7.25-7.18 (5H, m), 7.05 (1H, m), 6.83-6.78 (2H, m), 6.58 (1H, d), 4.76-4.63 (2H, m), 3.52-3.20 (2H, m), 2.87 (1H, m), 2.60-1.98 (8H, m), 1.03 (3H, d).<br>Found: C, 64.15; H, 6.45; N, 14.92. $C_{30}H_{34}N_6O_3 \cdot 2H_2O$ requires C, 64.02; H, 6.81; N, 14.94% |

Example 105: (5-{4-[(R)-α-(2(S),5(R)4-benzyl-2,5-dimethyl-1-piperazinyl)-3-hydroxybenzyl]phenyl}-2-tetrazolyl)-4-methylbenzoic acid.

Example 106: 3-(5-{4-[(R)-α-(2(S)-4-benzyl-2-methyl-1-piperazinyl)-3-hydroxybenzyl]phenyl}-2-tetrazolyl) propionic acid.

Example 107: 4-(5-{4-[(R)-α-(2(S)-4-benzyl-2-methyl-1-piperazinyl)-3-hydroxybenzyl]phenyl}-2-tetrazolyl)butanoic acid.

EXAMPLE 108

(5-{4-[(R)-α-(2(S),5(R)-4-Benzyl-2.5-dimethyl-1-piperazinyl)-3-hydroxybenzyl]phenyl}-1-tetrazolyl)-3-methylbenzoic Acid The compound of the following formula:

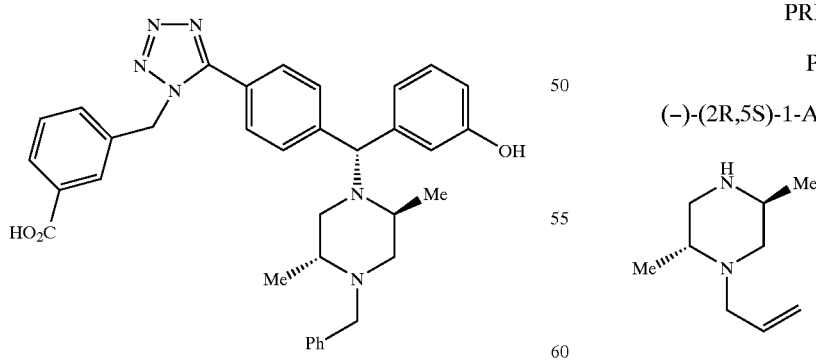

was prepared using a similar method to that described for Example 19 using the compound of Example 104.

$R_f$: 0.23 (dichloromethane/methanol/ammonium hydroxide; 95/5/0.5). m/z: 589 (MH⁺). $\delta_H$ (300 MHz, $d_6$-DMSO): 7.83 (1H d), 7.68 (3H, d), 7.55 (2H, d), 7.41 (1H, t), 7.35–7.09 (1H, m), 6.68 (3H, m), 5.88 (2H, s), 5.00 (1H, s), 3.77 (1H, d), 3.25 (1H, d), 2.60 (4H, m), 2.00 (1H, m), 1.88 (1H, m), 1.03 (6H, m). Found: C, 69.21; H, 6.04; N, 13.84. $C_{35}H_{36}N_6O_3 \cdot H_2O$ requires C, 69.29; H, 6.31; N, 13.85%.

EXAMPLE 109

The delta opioid agonist activity of a number of compounds were determined in mouse vas deferens (as described above) with the following results:

| Example | $pIC_{50}$ |
|---|---|
| 1 | 9.7 |
| 4 | 10.9 |
| 42 | 9.5 |

PREPARATIONS

Preparation 1

(−)-(2R,5S)-1-Allyl-2,5-dimethylpiperazine

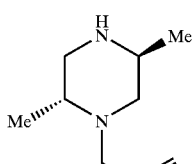

Trans-2,5-dimethylpiperazine (600 g), slurried in toluene (1200 ml), was heated to 85° C. with stirring, at which temperature, the solid dissolved completely. The solution was allowed to cool to room temperature gradually, with stirring, allowing slow precipitation of the solid, then cooled to 10° C. using an ice bath. The solid was filtered, washed with fresh, cold toluene (250 mls), and dried under vacuum (50° C.) overnight to yield a yellow crystalline solid (518.5 g).

Recrystallised trans-2,5-dimethylpiperazine (259.5 g) was slurried in cyclohexane (2.59 l) at room temperature. Sodium hydroxide solution (5 M; 500 ml) was added in one go with tetrabutylammonium chloride (4.3 g) and the reaction mixture was stirred whilst the allyl bromide solution (302.4 g) in cyclohexane (300 ml) was added in a stream, over approximately 30 mins. The temperature of the reaction mixture rose slowly to 33° C. over 30 mins, and was stirred for a further 1 hr. T.l.c analysis showed that the organic phase contained mostly mono-allylated product, with traces of bis-allylated impurity and starting material. The aqueous contained mostly starting material and some monoallylated product. The two phases were separated and the aqueous was stirred with fresh cyclohexane (2.5 L). Allyl bromide (82.5 g) in cyclohexane (100 ml), and sodium hydroxide solution (5 M, 136 ml) were added, and the mixture was stirred at room temperature for 1 hr. The phases were separated and the two cyclohexane phases were combined. The cyclohexane phase was backwashed with NaOH (1M, 200 ml) to remove traces of starting material and this wash was added to the aqueous layer and kept on one side. The organic extracts (containing only mono- and bis- allylated material) were stirred with $H_2O$ (1.5 L), and the pH of the mixture adjusted to precisely 8.0 using c.HCl. TLC showed the aqueous contained mono with a faint trace of bis. Organic contained bis with a faint trace of mono. The layers were separated, and the pH of the aqueous adjusted to 13.5 using NaOH (10 M), and extracted with $CH_2Cl_2$ (4×1 L). The previously held-back aqueous washings were extracted with $CH_2Cl_2$ (4×1 L). The combined organic extracts were dried over $MgSO_4$ and stripped (50° C.) to yield racemic 1-allyl-2,5-dimethylpiperazine as a yellow, mobile oil (278.9 g, 80%). [$R_f$=0.4, ($CH_2Cl_2$/MeOH/$NH_3$; 80:20:1)].

A solution of racemic 1-allyl-2,5-dimethylpiperazine (537.7 g) in acetone (1075 ml) was added in one portion to a stirred solution of (1R,3 S)-(+)-camphoric acid in acetone (5.2 L) at 40° C. Stirring was continued at 40° C. and a white precipitate began to form after approximately five minutes, which soon became very thick. The reaction mixture was stirred at gentle reflux for a further 1 hr before being cooled to 10° C. in an ice bath, and filtered. The precipitate was slurry-washed with fresh acetone (2 L), then washed on the filter pad with more acetone (1 L). The camphoric acid salt of (+)-(2S,5R)-1-allyl-2,5-dimethylpiperazine was dried under vacuum (60° C.) overnight to yield a white solid (577 g).

The crude enriched (−)-(2R,5S)-1-allyl-2,5-dimethylpiperazine (185.5 g) was redissolved in acetone (370 ml) and added to a solution of di-p-tolyl-D-tartaric acid monohydrate (486.5 g) in acetone (6.8 L) at 40° C. The reaction mixture was gently refluxed for 1 hr. The reaction mixture was cooled to 10° C. in an ice bath, filtered, washed with fresh acetone (3×500 mls), and dried under vacuum (60° C.) overnight to afford the tartrate salt as a white solid (466.4 g, mpt 191.7° C.). The di-p-tolyl-D-tartrate salt (466.4 g) was fully dissolved in methanol (10 L) at gentle reflux. The resulting pale yellow solution was distilled at atmospheric pressure to approximately half its original volume. The resulting clear solution was allowed to cool to room temperature and stirred for 72 hrs, during which time a thick white precipitate formed. The precipitate was filtered, washed with fresh methanol (2×500 mls) and dried under vacuum (50° C.) overnight to yield a white solid (382.1 g, mpt 194.3° C.).

A solution of sodium hydroxide (2M, 3l) and dichloromethane (3l) were stirred together at room temperature. The di-p-tolyl-D-tartrate salt from above (371.4 g) was added in one go, and the mixture stirred for 1 hr. The phases were separated and the aqueous washed with fresh $CH_2Cl_2$ (3×1 L). The organic extracts were combined and evaporate in vacuo to afford the title compound (−)-(2R,5S)-1-allyl-2, 5-dimethylpiperazine as a mobile yellow oil (104.3 g,).

$R_f$: 0.30 (93/7/1; dichloromethane/methanol/ammonium hydroxide). [α]$_D$−54.8° (c=1.19, Ethanol).

Preparation 2

2-4-[(R)-1-[(2S,5R)-4Allyl-2.5-dimethyl-1-piperazinyl]-1-(3-methoxyphenyl)methyl]phenyl-4, 4-dimethyl-4,5 dihydro-1,3-oxazole

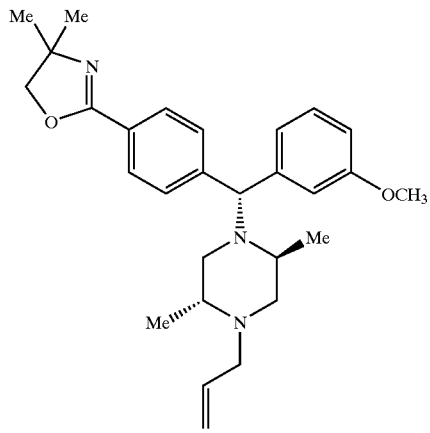

A solution of the Compound of Preparation 1 (1.5 g), benzotriazole (1.16 g) and 4-[(4,4-dimethyl)-1,3-oxazolin-2]benzaldehyde (1.98 g) (Preparation 45) in toluene (25 ml) was heated under reflux with azeotropic removal of water for 3.5 hours. The solution was cooled to ambient temperature and added to a cold solution (−10° C.) of 3-methoxyphenylmagnesium bromide (prepared from 3.64 g of the corresponding bromide and 0.47 g of magnesium turnings) in tetrahydrofuran (40 ml) at such a rate as to maintain the internal temperature in the range −10 to 0° C. The resulting solution was stirred at 0° C. for 15 minutes, ambient temperature for 30 minutes and then quenched with 2 N hydrochloric acid solution. The layers were separated and the aqueous solution extracted with diethyl ether (2×). The combined organic extracts were discarded. The aqueous solution was basified to pH 9 and extracted with diethyl ether (3×). The combined extracts were washed successively with water, 2 N sodium hydroxide, water and brine. The organic extracts were dried ($Na_2SO_4$) and evaporated to dryness in vacuo. The residue was purified by column chromatography over silica gel using gradient elution (30% $Et_2O$/$CH_2Cl_2$+1% MeOH) to afford the title compound. The αS-diastereomer was also isolated.

m/z: 476 (MH$^+$).

Preparation 3

4-[(R)1-[(2S,5R)-4-Allyl-2.5-dimethyl-1-piperazinyl]-1-(3-methoxyphenyl)methyl]benzonitrile

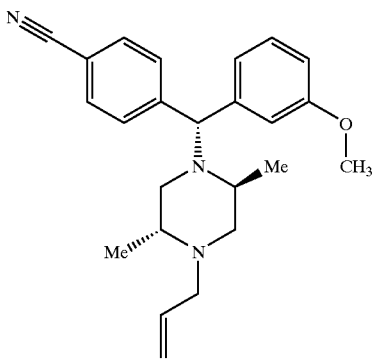

Phosphorus oxychloride (4.04 ml) was added dropwise to a stirred solution of the compound of Preparation 2 (4.93 g) in dry pyridine (30 ml). The dark brown solution was stirred at 85–95° C. for 18 hours, cooled in an ice-bath and quenched with excess 2N sodium hydroxide solution. Extraction with dichloromethane followed by drying (sodium sulphate) and evaporation in vacuo gave a brown semi-solid. The residue was purified by flash chromatography over silica gel (20% diethyl ether in dichloromethane) to afford the title compound, 3.21 g.

m/z: 376 (MH+). Rf: 0.42 (70/30/0.1 dichloromethane/diethyl ether/methanol).

Preparation 4

(±)-4-Cyano-[(R,S)-α-(4-benzyl-1-piperazinyl)-3-tert-butyldimethylsilyloxybenzyl]benzene

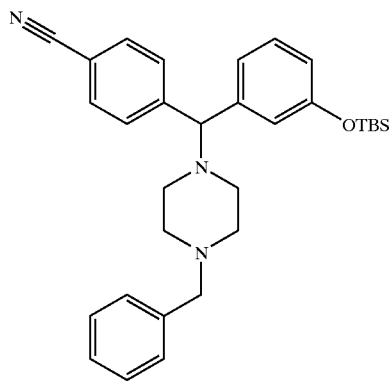

[TBS = t-butyldimethylsilyl]

A solution of (±)1-benzylpiperazine (8.8 g), benzotriazole (5.95 g) and 4-cyanobenzaldehyde (6.55 g) in toluene (150 ml) was heated under reflux with azeotropic removal of water for 30 minutes. The solution was cooled to ambient temperature and added to a cold solution (−25° C.) of 3-tert-butyldimethylsilyloxyphenylmagnesium bromide (prepared from 28.7 g of the corresponding bromide and 2.43 g of magnesium turnings) in tetrahydrofuran (100 ml) at such a rate as to maintain the internal temperature in the range −20° C. The resulting solution was stirred at 0° C. for 15 minutes, ambient temperature for 30 minutes and then quenched with saturated aqueous ammonium chloride solution. The layers were separated and the aqueous solution extracted with diethyl ether (2×200 ml). The combined organic extracts were dried (Na$_2$SO$_4$) and evaporated to dryness in vacuo. The residue was purified by column chromatography over silica gel using gradient elution (5–20% ethyl acetate/hexane) to afford the title compound, 17.0 g.

m/z: 498 (MH+). δ$_H$ (400 MHz, CDCl$_3$): 7.72 (2H, d), 7.56 (2H, d), 7.32–7.10 (6H, m), 6.95 (1H, d), 6.86 (1H, s), 6.66 (1H, d), 4.40 (1H, s), 3.44 (2H, s), 2.46–2.20 (8H, m), 0.90 (9H, s), 0.14 (6H, s).

(b) (±)-[(R,S)-α-(4-Benzyl-1-piperazinyl)-3-(tert-butyldimethylsilyl)oxybenzyl]phenyltetrazole

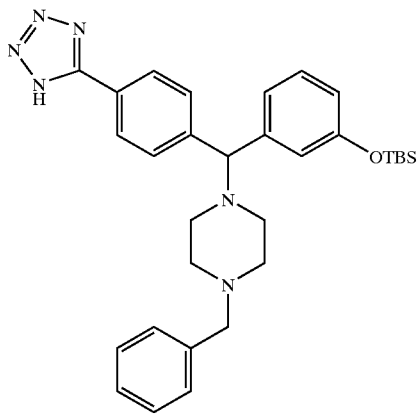

A solution of the first compound of part (a) (8.5 g), dibutyltin oxide (1.05 mg) and trimethylsilyl azide (4.3 g) in dry toluene (50 ml) were heated together under a gentle reflux for 5 hours. The reaction mixture was evaporated to dryness in vacuo and the residue purified by column chromatography over silica gel (80/20/3 dichloromethane/methanol/ammonium hydroxide) to afford the title compound, 8.06 g.

m/z: 541 (MH+). δ$_H$ (400 MHz, CDCl$_3$): 7.90 (2H, d), 7.48 (2H, d), 7.34–7.20 (5H, m), 7.14 (1H, t), 7.00 (1H, d), 6.94 (1H, s), 6.68 (1H, d), 4.32 (1H, s), 3.56 (2H, s), 2.50–2.28 (8H, m), 0.90 (9H, s), 0.16 (6H, s).

Preparation 5

(+)-4-Cyano-[(R)-α-(2(S),5(R)-4-allyl-2.5-dimethyl-1-piperazinyl)-3-tert-butyldimethylsilyoxybenzyl]benzene

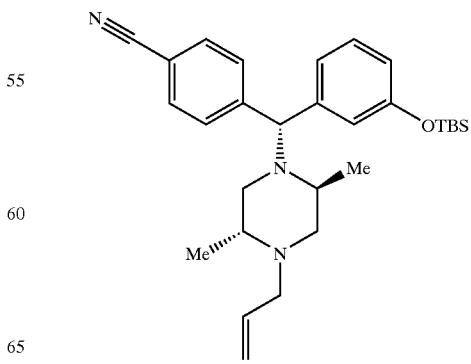

A solution of (−)-(2R,5S)-1-allyl-2,5-dimethylpiperazine (21.6 g), benzotriazole (16.68 g) and 4-cyanobenzaldehyde (18.35 g) in toluene (800 ml) was heated under reflux with azeotropic removal of water for 3 hours. The solution was cooled to ambient temperature and added to a cold solution (−10° C.) of 3-tert-butyldimethylsilyloxyphenylmagnesium bromide (prepared from 79 g of the corresponding bromide and 6.8 g of magnesium turnings) in tetrahydrofuran (500 ml) at such a rate as to maintain the internal temperature in the range −10 to 0° C. The resulting solution was stirred at 0° C. for 15 minutes, ambient temperature for 30 minutes and then quenched with saturated aqueous ammonium chloride solution. The layers were separated and the aqueous solution extracted with diethyl ether (2×200 ml). The combined organic extracts were dried ($Na_2SO_4$) and evaporated to dryness in vacuo. The residue was purified by column chromatography over silica gel using gradient elution (5–20% ethyl acetate/dichloromethane) to afford the title compound, 4-[(R)-α-(2(S), 5(R)-4-allyl-2,5-dimethyl-1-piperazinyl)-3-tert-butyldimethylsilyloxybenzyl]cyanobenzene, 32.9 g.

m/z: 476 (MH+). $R_f$: 0.35 (90/10/2; hexane/ethyl acetate/diethylamine). Found: C, 72.26; H, 8.78; N, 8.09. $C_{29}H_{41}N_3OSi.3/10EtOAc$ requires C, 72.23; H, 8.71, N, 8.37%. $[\alpha]_d$+22.9° (c=0.112, methanol).

Preparation 6

4-[(R)-1-[(2S,5R)-4-Allyl-2,5-dimethyl-1-piperazinyl]-1-(3-hydroxyphenyl)methyl]benzonitrile

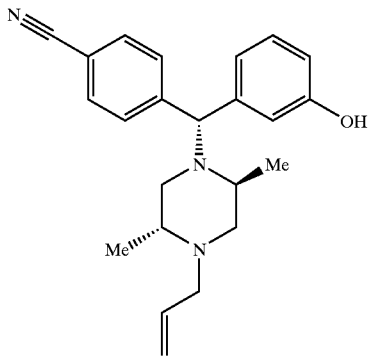

A solution of the compound of Preparation 5 (4.75 g) and tetraethylammonium fluoride (3.70 g) in tetrahydrofuran (100 ml) was stirred at room temperature for 4 hours. The mixture was partitioned between ethyl acetate and water, the layers separated, and the aqueous layer was extracted with ethyl acetate. The combined organic extracts were dried (MgSO4) and evaporated to dryness in vacuo. The residue was purified by column chromatography over silica gel using gradient elution (hexane to ethyl acetate) to afford the title compound, 3.46 g.

m/z: 362 (MH+). $R_f$: 0.21 (1/1 hexane/ethyl acetate).

Preparation 7

4-[(R)-1-[(2S,5R)-2,5-Dimethyl-1-piperazinyl]-1-(3-hydroxyphenyl)methyl]benzonitrile

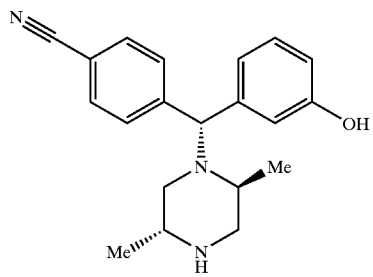

Tris(triphenylphosphine)rhodium(I) chloride (1.0 g) was added to a solution of the compound of Preparation 6 (3.37 g) in acetonitrile (80 ml) and water (20 ml). The reaction mixture was heated under a gentle reflux and the solvent allowed to distil off slowly. Additional acetonitrile/water (100 ml; 4:1 v/v) was added a such a rate as to maintain a steady distillation. After the addition of solvent was complete the distillation was continued until the volume was reduced to approximately 50 ml. The cooled solution evaporated to dryness in vacuo and the residue was purified by column chromatography over silica gel (80/20/3 dichloromethane/methanol/ammonium hydroxide;) to afford the title compound, 2.48 g.

m/z: 322 (MH+). $R_f$: 0.20 (93/7/1 dichloromethane/methanol/ammonia).

Preparation 8

4-[(R)-1-[(2.5S, 5R)-4-Ethyl-2,5-dimethyl-1-piperazinyl]-1-(3-hydroxyphenyl)methyl]benzonitrile

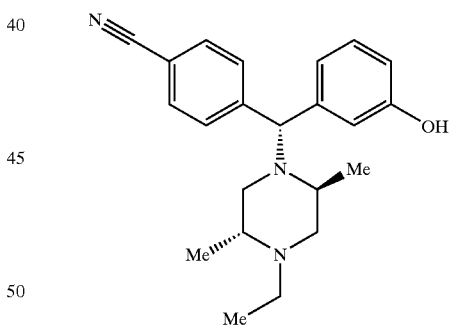

To a solution of the compound of Preparation 7 (482 mg) and acetaldehyde (132 mg) in tetrahydrofuran (10 ml) containing glacial acetic acid (100 mg) was added sodium triacetoxyborohydride (636 mg). The mixture was stirred at room temperature for 1 hour and then poured into ethyl acetate and washed with saturated sodium hydrogen carbonate solution and saturated brine. The organic phase was dried (MgSO4) and evaporated to dryness in vacuo. The residue was purified by column chromatography over silica gel using gradient elution (100% dichloromethane to 6% methanol/dichloromethane) to afford the title compound as a white foam, 295 mg.

m/z: 350 (MH+). Rf: 0.32 (93/7/1 dichloromethane/methanol/ammonia).

Preparations 9 to 13

The following compounds of the general formula:

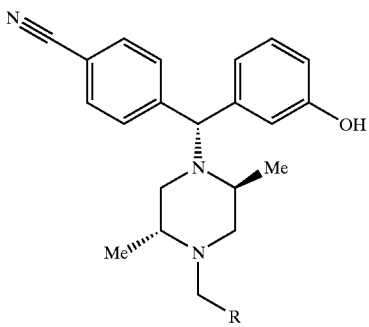

or salts thereof, were prepared from the compound of Preparation 7 by reductive alkylation with the appropriate aldehyde by similar methods to that used in Preparation 8.

| Prep | R | Yield | m/z | Rf Solvent |
|---|---|---|---|---|
| 9 | Et | 460 mg | 364 | 0.35(93/7/1) |
| 10 | Ph | 541 mg | 412 | 0.57(93/7/1) |
| 11 | Thiazol-2-yl | 546 mg | 419 | 0.44(93/7/1) |
| 12 | H | 407 mg | 336 | 0.30(93/7/1) |
| 13 | CO$_2$H | 467 mg | 380 | 0.77(77/20/3) | solvent system dichloromethane/methanol/ammonia
Preparation 9 [(R)-1-[(2S,5R)4-propyl-2,5-dimethyl-1-piperazinyl]-1-(3-hydroxyphenyl)methyl]benzonitrile
Preparation 10 [(R)-1-[(2S,5R)-4-benzyl-2,5-dimethyl-1-piperazinyl]-1-(3-hydroxyphenyl)methyl]benzonitrile
Preparation 11 [(R)-1-[(2S,5R)-2,5-dimethyl-4-(1,3-thiazol-2-ylmethyl)-1-piperazinyl]-1-(3-hydroxyphenyl)methyl]benzonitrile
Preparation 12 [(R)-1-[(2S,5R)-2,4,5-trimethyl-1-piperazinyl]-1-(3-hydroxyphenyl)methyl]benzonitrile
Preparation 13 (2R,5S)-4-[(R)-(4-cyanophenyl)-1-(3-hydroxyphenyl)methyl]-2,5-dimethyl-1-piperazinylacetic acid

Preparation 14

4-[(R)-1-[(2S,5R)-2,5-Dimethyl-1-piperazinyl]-1-(3-(tert-butyldimethylsilyloxy)phenyl)methyl]benzonitrile

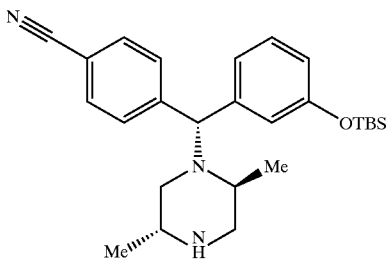

Tris(triphenylphosphine)rhodium(I) chloride (0.77 g) was added to a solution of the compound of Preparation 5 (10 g) in acetonitrile (80 ml) and water (20 ml). The reaction mixture was heated under a gentle reflux and the solvent allowed to distil off slowly. Additional acetonitrile/water (100 ml; 4:1 v/v) was added a such a rate as to maintain a steady distillation. After the addition of solvent was complete the distillation was continued until the volume was reduced to approximately 50 ml. The cooled solution was partitioned between ethyl acetate and saturated aqueous sodium hydrogen carbonate solution. The layers were separated and the organic phase was dried (MgSO4) and evaporated to dryness in vacuo. The residue was purified by column chromatography over silica gel (90/10/2 dichloromethane/methanol/ammonium hydroxide;) to afford the title compound, 8.60 g.

m/z: 436 (NH+). Rf: 0.31 (93/7/1 dichloromethane/methanol/ammonia).

Preparation 15

4-[(R)-1-[(2S,5R)-4-Acetyl-2,5-dimethyl-1-piperazinyl]-1-(3-(tert-butyldimethylsilyl)oxyphenyl)methyl]benzonitrile

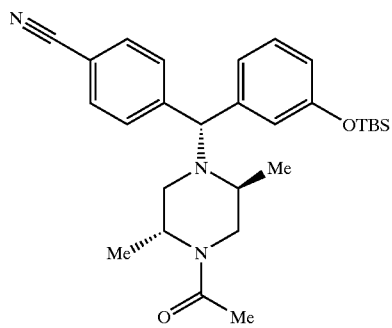

A solution of the compound of Preparation 14 (870 mg), triethylamine (303 mg) and acetic anhydride (224 mg) in dichloromethane (15 ml) was stirred at room temperature for 2 hours. The reaction mixture was poured into water and extracted with dichloromethane (3×50 ml). The combined extracts were dried (MgSO4) and evaporated to dryness in vacuo. The residue was purified by column chromatography over silica gel (ethyl acetate) to give the title compound, 781 mg.

m/z: 478 (MH+). Rf: 0.43 (ethyl acetate).

Preparation 16

4-[(R)-1-[(2S,5R)-4-Acetyl-2,5-dimethyl-1-piperazinyl]-1-(3-hydroxyphenyl)methyl]benzonitrile

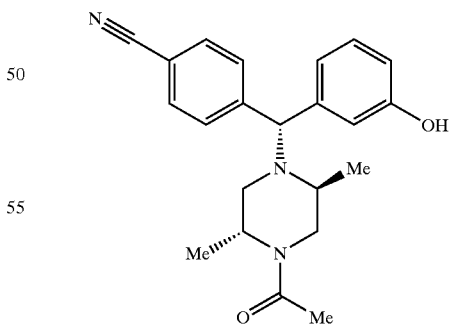

To a solution of the compound of Preparation 15 (775 mg) in tetrahydrofuran (19 ml) was added a solution of tetraethylammonium fluoride (600 mg) in water (1 ml) and the resulting mixture was stirred at room temperature for 22 hours. The mixture was partitioned between ethyl acetate and water and the layers separated. The organic extracts were washed with water and saturated brine solution, dried (MgSO4) and evaporated to dryness in vacuo. The residue was purified by column chromatography over silica gel (ethyl acetate) to afford the title compound, 616 mg.

m/z: 364 (MH+). Rf: 0.27 (ethyl acetate).

Preparation 17

4[(R)-1-[(2S,5R)-4-Cyclopropylmethyl-2,5-dimethyl-1-piperazinyl]-1-(3-(tert-butyldimethylsilyloxy)phenyl)methyl]benzonitrile

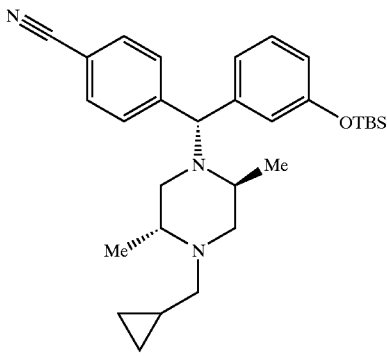

To a solution of the compound of Preparation 14 (870 mg) and cyclopropane carboxaldehyde (168 mg) in tetrahydrofuran (20 ml) containing glacial acetic acid (132 mg) was added sodium triacetoxyborohydride (848 mg). The mixture was stirred at room temperature for 1.5 hours and then poured into ethyl acetate and washed with saturated sodium hydrogen carbonate solution and saturated brine. The organic phase was dried (MgSO$_4$) and evaporated to dryness in vacuo. The residue was purified by column chromatography over silica gel using gradient elution (100% hexane to 50% hexane/ethyl acetate) to afford the title compound as a gum, 798 mg.

m/z: 490 (MH+). Rf: 0.57 (ethyl acetate).

Preparations 18 to 20

The following compounds of the general formula:

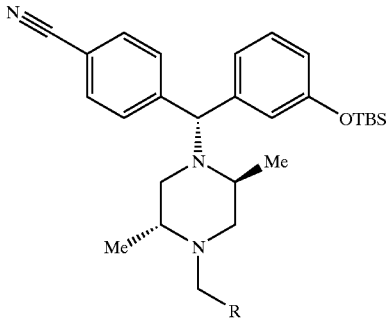

or salts thereof, were prepared from the compound of Preparation 14 by reductive alkylation with the appropriate aldehyde by similar methods to that used in Preparation 17.

| Prep. No. | R | Yield | m/z | Rf (1:1 EtOAc/Hexane) |
|---|---|---|---|---|
| 18 | 4-F-C6H4-CH2- | 76% | 544 | 0.81 |
| 19 | 4-MeO-C6H4-CH2- | 87% | 556 | 0.73 |
| 20 | 4-CF3-C6H4-CH2- | 85% | 594 | 0.81 |

Preparation 18 [(R)-1-[(2S,5R)-4-(4-fluorobenzyl)-2,5-dimethyl-1-piperazinyl]-1-(3-(tert-butyldimethylsilyl)oxyphenyl)methyl]benzonitrile.

Preparation 19 [(R)-1-[(2S,5R)-4-(4-methoxybenzyl)-2,5-dimethyl-1-piperazinyl]-1-(3-(tert-butyldimethylsilyl)oxyphenyl)methyl]benzonitrile.

Preparation 20 [(R)-1-[(2S,5R)-4-(4-trifluoromethylbenzyl)-2,5-dimethyl-1-piperazinyl]-1-(3-(tert-butyldimethylsilyl)oxypehenyl)methyl]benzonitrile.

Preparation 21

4-[(R)-1-[(2S,5R)-4-Cyclopropylmethyl-2,5-dimethyl-1-piperazinyl]-1-(3-hydroxyphenyl)methyl]benzonitrile

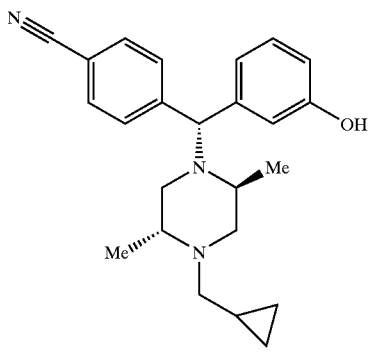

To a solution of the compound of Preparation 17 (786 mg) in tetrahydrofuran (18 ml) was added a solution of tetraethylammonium fluoride (592 mg) in water (2 ml) and the resulting mixture was stirred at room temperature for 20 hours. The mixture was partitioned between ethyl acetate and water and the layers separated. The organic extracts were washed with water and saturated brine solution, dried (MgSO4) and evaporated to dryness in vacuo. The residue was purified by column chromatography over silica gel (ethyl acetate) to afford the title compound, 617 mg.

m/z: 376 (MH+). Rf: 0.35 (ethyl acetate).

Preparations 22 to 24

The following compounds of the general formula:

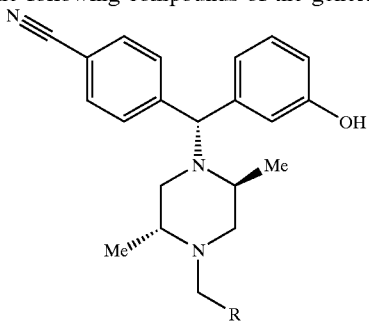

or salts thereof, were prepared by desilylation of the corresponding silyl ethers (see Preparations 18 to 20) by similar methods to that used in Preparation 21.

| Prep. No. | R | Yield | m/z | Rf (1:1 EtOAc/Hexane) |
|---|---|---|---|---|
| 22 | 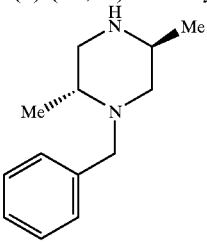 (F-C6H4-CH2-*) | 99% | 430 | 0.5 |
| 23 | MeO-C6H4-CH2-* | 81% | 442 | 0.37 |
| 24 | CF3-C6H4-CH2-* | 90% | 480 | 0.60 |

Preparation 22 [(R)-1-(2S,5R)-2,5-dimethyl-4-[4-fluorobenzyl]-1-piperazinyl-1-(3-hydroxyphenyl)methyl]benzonitrile.
Preparation 23 [(R)-1-(2S,5R)-2,5-dimethyl-4-[4-methoxybenzyl]-1-piperazinyl-1-(3-hydroxyphenyl)methyl]benzonitrile.
Preparation 24 [(R)-1-(2S,5R)-2,5-dimethyl-4-[4-(trifluoromethyl)benzyl]-1-piperazinyl-1-(3-hydroxyphenyl)methyl]benzonitrile.

Preparation 25

(2S,5R)-1-Allyl-4-benzyl-2,5-dimethylpiperazine

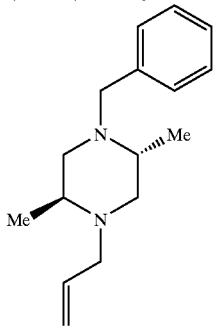

To a suspension of the camphoric acid salt of (+)-(2S,5R)-1-allyl-2,5-dimethylpiperazine from Preparation 1 (78.2 g) and benzaldehyde (26.5 g) in tetrahydrofuran (500 ml) containing glacial acetic acid (2 ml) was added sodium triacetoxyborohydride (93.3 g) portionwise over 10 minutes. The resulting mixture was stirred at room temperature for 4 hours. The reaction was partitioned between ethyl acetate (1500 ml) and aqueous sodium hydroxide (750 ml of 2N solution). The layers were separated and the organic phase was washed with 10% sodium metabisulphite solution (200 ml) and saturated brine solution. The organic layer was dried (MgSO4) and evaporated to dryness in vacuo to give the title compound, 52.1 g.

m/z: 245 (MH+). Rf: 0.63 (93/7/1 dichloromethane/methanol/ammonium hydroxide).

Preparation 26

(−)-(2R,5S)-1-Benzyl-2,5-dimethylylpiperazine

Tris(triphenylphosphine)rhodium(I) chloride (3 g) was added to a solution of the compound of Preparation 25 (52.1 g) in acetonitrile (400 ml) and water (80 ml). The reaction mixture was heated under a gentle reflux and the solvent allowed to distil off slowly. Additional acetonitrile/water (250 ml; 4:1 v/v) was added a such a rate as to maintain a steady distillation. After the addition of solvent was complete the distillation was continued until the volume was reduced to approximately 200 ml. The cooled solution was partitioned between ethyl acetate and 2N hydrochloric acid. The layers were separated and the organic phase extracted with further 0.5N hydrochloric acid. The combined aqueous extracts were basified with 2N sodium hydroxide solution and extracted into dichloromethane. The combined organic extracts were dried (MgSO4) and evaporated to dryness in vacuo, to afford the title compound, 38.2 g.

m/z: 205 (MH+). Rf: 0.27 (93/7/1 dichloromethane/methanol/ammonia). [α]$_D$-113° (c 0.2, methanol).

Preparation 27

[(R)-1-(2S,5R)-2,5-Dimethyl-4-benzyl-1-piperazinyl-1-(3-(tert-butyldimethylsilyl)oxyphenyl)methyl]benzonitrile and

[(S)-1-(2S,5R)-2,5-Dimethyl-4-benzyl-1-piperazinyl-1-(3-(tert-butyldimethylsilyl)oxyphenyl)methyl]benzonitrile

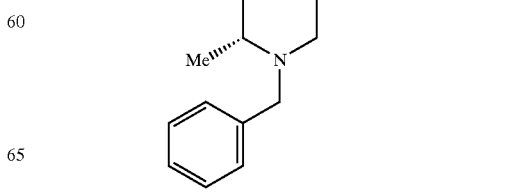

and

-continued

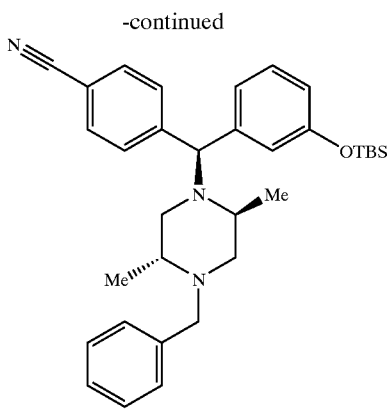

A solution of the compound of Preparation 26 (10.2 g), benzotriazole (5.95 g) and 4-cyanobenzaldehyde (6.55 g) in toluene (150 ml) was heated under reflux with azeotropic removal of water for 3 hours. The solution was cooled to ambient temperature and added to a cold solution (−25° C.) of 3-tert-butyldimethylsilyloxyphenylmagnesium bromide (prepared from 28.7 g of the corresponding bromide and 2.4 g of magnesium turnings) in tetrahydrofuran (100 ml) at such a rate as to maintain the internal temperature at −25° C. The resulting solution was stirred at 0° C. for 15 minutes, ambient temperature for 30 minutes and then quenched with 2N sodium hydroxide solution. The layers were separated and the aqueous solution extracted with ethyl acetate (2×). The combined organic extracts were washed with water, and brine. The organic extracts were dried ($Na_2SO_4$) and evaporated to dryness in vacuo. The residue was purified by column chromatography over silica gel using gradient elution (100% dichloromethane to 10% ethyl acetate/dichloromethane) to afford the title compounds. The αR-diastereomer was the first to elute, 17.38 g.

m/z: 526 (MH+). Rf: 0.62 (3/1 hexane/ethyl acetate).

The αS-diastereomer was also isolated and eluted second, 2.61 g.

m/z: 526 (MH+). Rf: 0.53 (3/1 hexane/ethyl acetate).

Preparation 28

[(R)-α-(2(S),5(R)-4-Benzyl-2,5-dimethyl-1-piperazinyl)-3-(tert-butyldimethylsilyl)oxybenzyl]phenyltetrazole

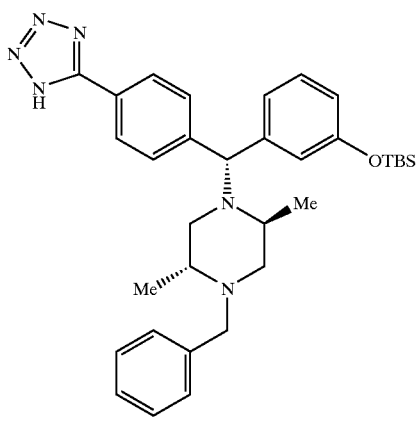

A solution of the first compound of Preparation 27 (7.88 g) dibutyltin oxide (750 mg) and trimethylsilyl azide (3.45 g) in dry toluene (50 ml) were heated together under a gentle reflux for 5.5 hours. The reaction mixture was evaporated to dryness in vacuo and the residue purified by column chromatography over silica gel (85/15/2 dichloromethane/methanol/ammonium hydroxide) to afford the title compound, 7.45 g.

m/z: 569 (MH+). Rf: 0.44 (80/20/3 dichloromethane/methanol/ammonia).

Preparations 29 and 30

2-[2-(5-4-[(R)-1-[(2S,5R)-4-Benzyl-2,5-dimethyl-1-piperazinyl]-1-(3-hydroxyphenyl)methyl]phenyl-2H-1,2,3,4-tetrazol-2-yl)ethoxy]acetonitrile and 2-[2-(5-4-[(S)-1-[(2S,5R)-4-Benzyl-2,5-dimethyl-1-piperazinyl]-1-(3-hydroxyphenyl)methyl]phenyl-2H-1,2,3,4-tetrazol-1-yl)ethoxy]acetonitrile

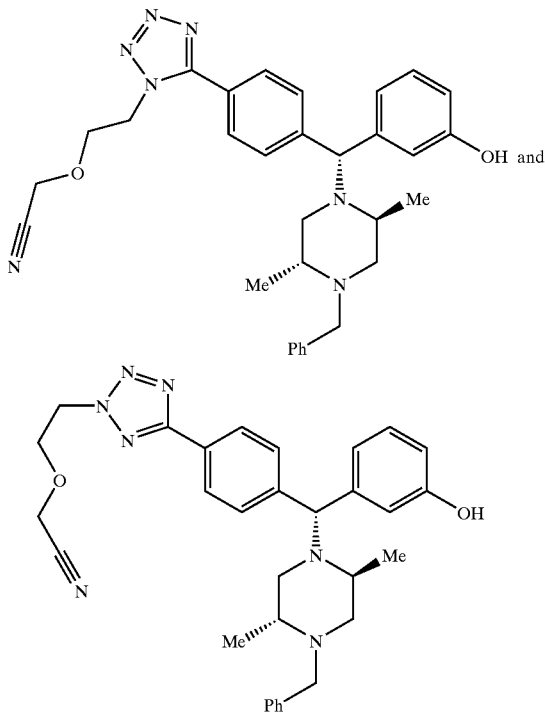

A solution of the compound of Preparation 28 (2.12 g), 5-bromo-3-oxopentanenitrile (620 mg)) and potassium carbonate (1.38 g) in acetonitrile (40 ml)) was heated under a gentle reflux for 2.5 hours. The cooled reaction mixture was partitioned between water and ethyl acetate. The aqueous layer was separated and extracted with further ethyl acetate. The combined organic extracts were washed with water, saturated brine solution, dried ($Na_2SO_4$) and evaporated to dryness in vacuo. The residue was dissolved in tetrahydrofuran (20 ml) and tetraethylammonium fluoride (1.48 g) in water (2 ml) added. The mixture was stirred at room temperature for 20 hours then partitioned between ethyl acetate and water. The layers were separated and the organic phase was washed with water and saturated brine solution, dried ($MgSO_4$) and evaporated to dryness in vacuo. The residue was purified by column chromatography over silica gel (100% hexane to 60% ethyl acetate/hexane) to afford the N-2 isomer, 1.43 g, followed by the N-1 isomer, 137 mg.

Data for N-2 Isomer: m/z: 538 (MH+). Rf: 0.26 (1/1 ethyl acetate/hexane).

Data for N-1 Isomer: m/z: 538 (MH+). Rf: 16 (1/1 ethyl acetate/hexane).

Preparation 31

4-{5-[(R)-α-(2(S),5(R)-4-Allyl-2,5-dimethyl-1-piperazinyl)-3-tert-butyldimethylsilyloxybenzyl]-tetrazolyl}benzene

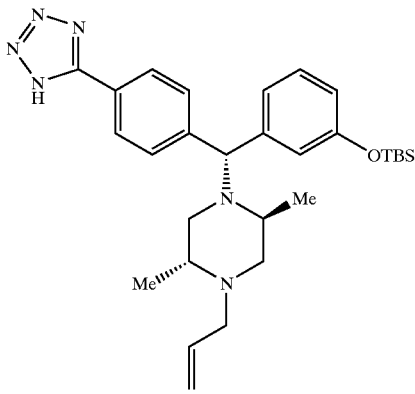

A solution of the compound of Preparation 5 (8.1 g), dibutyltin oxide (3.0 g) and trimethylsilyl azide (9.96 g) in dry toluene (60 ml) was heated at 80° C. for 72 hours under nitrogen. To the cooled reaction mixture was added 880 ammonium hydroxide solution and the layer separated. The aqueous solution was diluted with water (100 ml) and extracted with ethyl acetate (2×100 ml). The combined organic extracts were washed with water and saturated brine, dried (Na2SO4) and evaporated to dryness in vacuo. The residue was purified by column chromatography over silica gel using gradient elution (90/10/2 to 80/20/3 dichloromethane/methanol/ammonia) to afford the title compound, 7.76 g.

m/z: 519 (MH+). $R_f$: 0.40 (80/20/3 dichloromethane/methanol/ammonia).

Preparation 32

3-cyano-[(R)-α-(2(S),5(R)-4-Allyl-2,5-dimethyl-1-piperazinyl)-3-tert-butyldimethylsilyloxybenzyl]benzene The compound of the following formula:

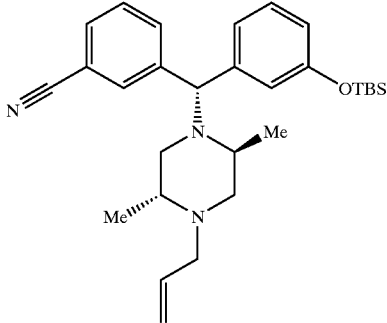

was prepared by a similar method to that used in Preparation 5 but using 3-cyanobenzaldehyde.

m/z: 476 (MH+). Rf. 0.35 (90/10/2; hexane/isopropanol/ammonium hydroxide). Found: C, 72.68; H, 8.71; N, 8.28. $C_{29}H_{41}N_3OSi$ requires C, 73.21; H, 8.69; N, 8.83%.

Preparation 33

(+)-3-{5-[(R)-α-(2(S),5(R)-4-Allyl-2,5-dimethyl-1-piperazinyl)-3-tert-butyldimethylsilyloxybenzyl]-tetrazolyl}benzene

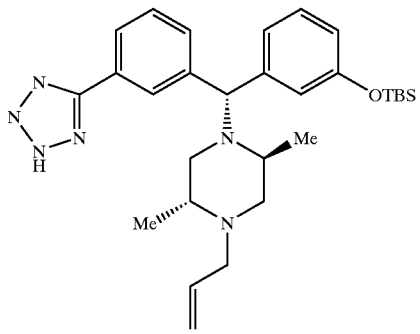

A mixture of the compound of Preparation 32 (5 g), azidotrimethylsilane (2.67 g) and dibutyltin oxide (0.94 g) in toluene (40 ml) was heated, with stirring, at 70° C. for 72 hours. The cooled reaction mixture was poured into ammonium hydroxide and ethyl acetate and the layers separated. The ammonium hydroxide solution was diluted with water and extracted with further ethyl acetate (2×). The combined organic extracts were washed with saturated brine, dried (Na2SO4), and evaporated in vacuo. The residue was purified by column chromatography over silica gel (dichloromethane/methanol/ammonium hydroxide; 80/20/3) to afford the title compound, 4.91 g.

m/z: 519 (MH+). Rf. 0.25 (80/20/3; ethyl acetate/methanol/ammonium hydroxide). $[\alpha]_D$+22.6° (c=0.124, methanol). Found: C, 64.71; H, 8.16; N, 15.70. $C_{29}H_{42}N_6OSi \cdot H_2O$ requires C, 64.89; H, 8.26; N, 15.66%.

Preparation 34

(+)-Methyl 4-[(R)-1-[(2S,5R)-Allyl-2,5-dimethyl-1-piperazinyl]-1-(3-methoxyphenyl)methyl]benzoate

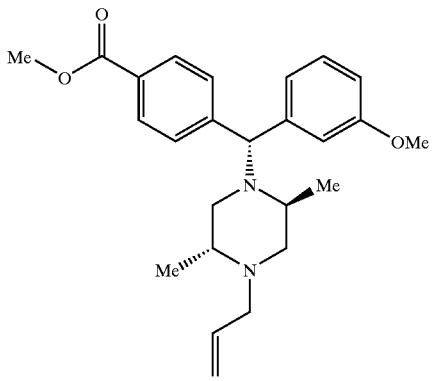

A solution of the compound of Preparation 1 (11.55 g), benzotriazole (8.93 g) and methyl 4-formylbenzoate (12.32 g) in toluene (100 ml) was heated under reflux with azeotropic removal of water for 3 hours. The solution was cooled and added to a cold solution (−20° C.) of 3-methoxyphenylmagnesium bromide (prepared from 28.05 g of the 3-bromoanisole and 3.65 g of magnesium turnings) in tetrahydrofuran (100 ml) at such a rate as to maintain the internal temperature in the range −20 to −15° C. The

Preparation 35

(+)-4-[(R)-1-[(2S,5R)-4-Allyl-2,5-dimethyl-1-pipierazinyl]-1-(3-methoxyphenyl)methyl]benzoic Acid

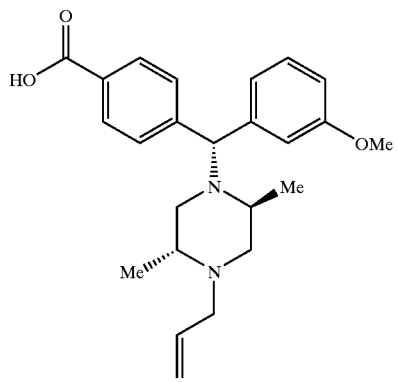

To a solution of the compound from Preparation 34 (27.9 g) in methanol (200 ml) was added 2N aqueous sodium hydroxide solution. The resulting suspension was stirred at room temperature for 20 hours, and then at 50° C. for 2 hours. Solid sodium hydroxide (3.2 g) was added and the mixture warmed at 50° C. for a further hour. The cooled solution was evaporated to dryness and the residue purified by column chromatography over silica gel (dichloromethane/methanol/ammonium hydroxide; 77/20/3) to afford the title compound, 11.06 g $\delta_H$ (300 MHz, CDCl$_3$): 7.97 (2H, d), 7.52 (2H, d), 7.23 (1H, m), 6.79 (3H, m), 6.60 (1H, v br s), 5.91 (1H, m), 5.23 (3H, m), 3.77 (3H, s), 3.41 (1H, dd), 3.02 (1H, dd), 2.90 (1H, m), 2.80 (1H, m), 2.64 (2H, m), 2.28 (1H, m), 2.05 (1H, m), 1.19 (3H, d), 1.05 (3H, d). m/z: 395 (MH$^+$). [α]$_D$+17.1° c=0.105, methanol.

resulting solution was stirred at −20° C. for 5 minutes and then warmed to room temperature, quenched with saturated aqueous ammonium chloride solution (200 ml). The layers were separated and the aqueous solution extracted with ethyl acetate (2×200 ml). The combined organic extracts were dried (MgSO$_4$) and evaporated to dryness in vacuo. The residue was purified by column chromatography over silica gel using gradient elution (Hexane to 50% ethyl acetate/hexane) to afford the title compound, 27.95 g.

m/z: 409 (MH$^+$). Rf: 0.31 (95/5/0.5; hexane/isopropanol/ammonium hydroxide). [α]$_d$+20.7° (c=0.145, methanol). Found: C, 71.12; H, 7.66; N, 6.58. C$_{25}$H$_{32}$N$_2$O$_3$·1/5H$_2$O requires C, 71.13; H, 6.67; N, 6.58%.

Preparation 36

Ethyl 5-(4-[(R)-1-[(2,S,5R)-4-Allyl-2,5-dimethyl-1-piperazinyl]-1-(3-methoxyphenyl)methyl]phenylcarboxamido)pentanoate

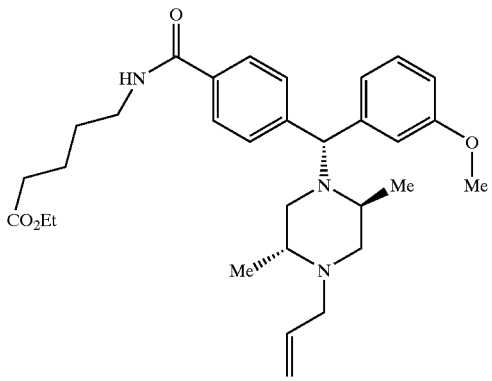

A solution of the compound of Preparation 35 (2.512 g), 1-hydroxybenzotriazole (1.55 g), diisopropylethylamine (2.44 ml) and 1-(3-dimethylaminopropyl)-3-ethylcarbodiimide hydrochloride (1.464 g) in dry dichloromethane (30 ml) was stirred under nitrogen for 1 hour. To this was added ethyl 5-aminovalerate.HCl (1.39 g) and further dichloromethane (10 ml). The reaction mixture was stirred at room temperature overnight, diluted with dichloromethane (100 ml) and washed with water (20 ml). The organic solution was dried (sodium sulphate) and evaporated in vacuo. The brown residue was purified by column chromatography over silica gel (98/2; dichloromethane/methanol) to afford the title compound, 2.965 g.

m/z: 522 (MN+). Rf: 0.31 (95/5; dichloromethane/methanol).

Preparation 37

Methyl 4-[(R)-1-[(2S,5R)-4-Allyl-2,5-dimethyl-1-piperazinyl]-1-(3-tert-butyldimethylsilyloxyphenyl)methyl]benzoate

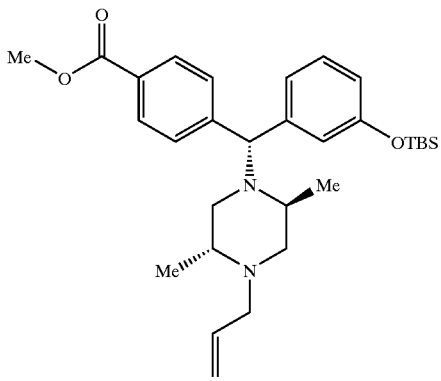

A solution of (−)-(2R,5S)-1-allyl-2,5-dimethylpiperazine (22.26 g), benzotriazole (17.18 g) and methyl 4-formylbenzoate (23.7 g) in toluene (400 ml) was heated under reflux with azeotropic removal of water for 3 hours. The solution was cooled and added to a cold solution (−20° C.) of 3-tert-butyldimethylsilyloxyphenylmagnesium bromide (prepared from 82.9 g of corresponding bromide and 7.29 g of magnesium turnings) in tetrahydrofuran (300 ml)

at such a rate as to maintain the internal temperature in the range −20 to −15° C. The resulting solution was stirred at −20° C. for 1.5 hours and then warmed to room temperature, quenched with saturated aqueous ammonium chloride solution (200 ml). The layers were separated and the aqueous solution extracted with ethyl acetate (2×200 ml). The combined organic extracts were dried (MgSO$_4$) and evaporated to dryness in vacuo. The residue was purified by column chromatography over silica gel (85/15/2 hexane/ethyl acetate/diethyl amine) to afford the title compound, 54.45 g.

m/z: 509 (MH$^+$). R$_f$: 0.44 (93/7/1 dichloromethane/methanol/ammonium hydroxide).

Preparation 38

(+)-4-[(R)-1-[(2S,5R)-4-Allyl-2,5-dimethyl-1-piperazinyl]-1-(3-hydroxyphenyl)methyl]benzoic Acid

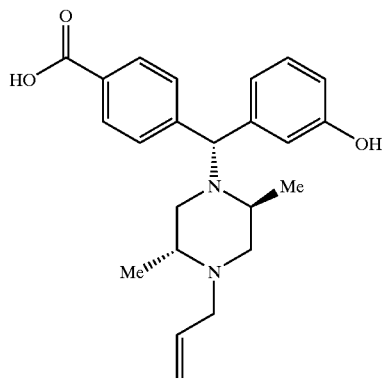

To a solution of the compound of Preparation 37 (54.45 g) in methanol (150 ml) and dioxane (100 ml) was added sodium hydroxide (214 ml of 5N aqueous solution), The resulting solution was stirred at room temperature for 18 hours, cooled to 0° C. and neutralised to pH 7–8 with hydrochloric acid. The solution was evaporated to dryness in vacuo and the residue purified by column chromatography over silica using gradient elution (95/5/0.5 to 80/20/3 dichloromethane/methanol/ammonium hydroxide) to afford the title compound, 25.98 g.

m/z: 381 (MH+). Rf: 0.14 (80/20/3 dichloromethane/methanol/ammonium hydroxide). [α]$_D$+25.4° (c 0.12, methanol).

Preparation 39

(+)-Methyl2-(4-[(R)-1-[(2S,5R)-4-Allyl-2,5-dimethyl-1-piperazinyl]-1-(3-hydroxyphenyl)methyl]phenylcarboxamido)acetate

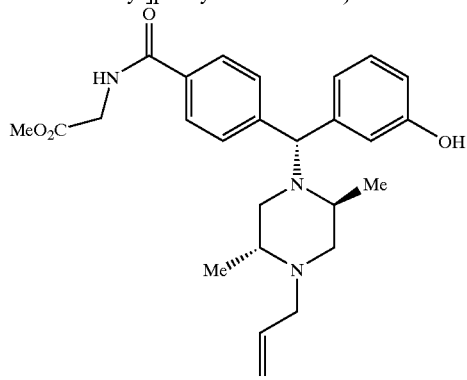

A solution of the compound of Preparation 38 (11.3 g), 1-hydroxybenzotriazole (7.22 g), diisopropylethylamine (21.4 ml), 1-(3-dimethylaminopropyl)-3-ethylcarbodiimide hydrochloride (6.83 g) and glycine methyl ester hydrochloride (4.48 g) in dry dichloromethane (150 ml) was stirred at room temperature for 48 hours. The solution was washed with water and evaporated to dryness in vacuo. The residue was purified by column chromatography over silica gel (93/2/0.5 ethyl acetate/methanol/ammonia) to give the title compound, 12.8 g.

m/z: 452 (MH+). Rf: 0.4 (95/5/0.5 ethyl acetate/methanol/ammonia). [α]$_D$+20.8° (c 0.13, methanol).

Preparation 40

Methyl 2-(4-[(R)-1-[(2S,5R)-4-Allyl-2,5-dimethyl-1-piperazinyl]-1-(3-tert-butyldimethylsilyloxyphenyl)methyl]phenylcarboxamido)acetate

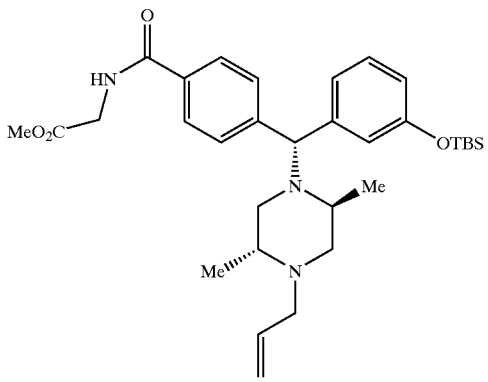

A solution of the compound of Preparation 39 (10 g), imidazole (1.58 g) and chlorotert-butyldimethylsilane (3.5 g) in dichloromethane (60 ml) was stirred under nitrogen for 18 hours. The reaction mixture was diluted with dichloromethane (100 ml) and washed successively with water (50 ml) and saturated aqueous sodium hydrogen carbonate (50 ml), dried over sodium sulphate and evaporated in vacuo to afford the title compound, 12.29 g.

m/z: 566 (MH+). Rf: 0.62 (95/5/0.5 dichloromethane/methanol/ammonia).

Preparation 41

2-[2-(5-4-[(R)-1-[(2S,5R)-4-Allyl-2,5-dimethyl-1-piperazinyl]-1-(3-hydroxyphenyl)methyl]phenyl-2H-1,2,3,4-tetrazol-2-yl)ethoxy]acetonitrile

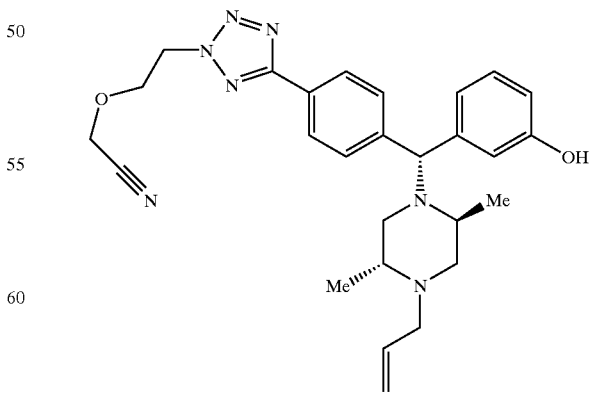

A solution of the compound of Preparation 31 (5.34 g), 2-bromoethoxyacetonitrile (1.47 g) and potassium carbonate (3.88 g) in 2-butanone (60 ml) was heated under a gentle reflux for 18 hours. The cooled reaction mixture was partitioned between water and ethyl acetate. The aqueous layer was separated and extracted with further ethyl acetate. The combined organic extracts were washed with water, saturated brine solution, dried (Na2SO4) and evaporated to dryness in vacuo to give a brown gum. The residue was purified by column chromatography over silica gel (95/5/0.5 diethyl ether/ethanol/ammonia) to afford the title compound, 3.46 g.

m/z: 488 (MH$^+$). R$_f$: 0.61 (95/5/0.5 diethyl ether/ethanol/ammonium hydroxide).

Preparation 42

4-(1H-1,2,3,4-tetraazol-5-yl)benzaldehyde

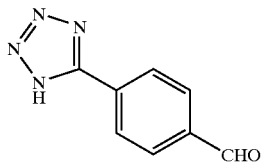

Trimethylsilyl azide (25 g) and dibutyltin oxide (8.8 g) were added to a solution of 4-cyanobenzaldehyde (13 g) in toluene (200 ml). The reaction was stirred with warming to 50° C. over 1 hr, and then warmed to 96° C. over 30 minutes and maintained at that temperature for 3 hours. The solvent was evaporated in vacuo to afford an orange oil which was purified by column chromatography over silica gel (ethyl acetate). The crude product was dissolved in refluxing toluene and allowed to cool with stirring overnight. The resulting slurry was granulated in an ice-bath for 1 hour, filtered and washed with cold toluene. The filtrate was evaporated in vacuo to afford a solid. The solid was dissolved in refluxing ethyl acetate (250 ml) and concentrated to 60 ml by rotary evaporation. The solution was cooled to room temperature and then granulated in an ice bath. The thick slurry was collected by filtration, washed and dried, with warming, in a vacuum oven to afford the title compound, 12 g.

Preparation 43

Ethyl 5-[5-(4-Formylphenyl)-2H-1,2,3,4-tetraazol-2-yl]pentanoate

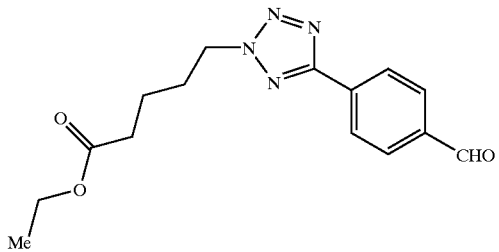

A mixture of the compound of Preparation 42 (450 g), potassium carbonate (715.5 g) and ethyl 5-bromovalerate (593.1 g) in acetonitrile (4500 ml) was heated together under reflux for 5 hours. The suspension was cooled to room temperature and water (4500 ml) added. The aqueous portion was separated and extracted with ethyl acetate (4500 ml). The combined organic portions were washed with water (2000 ml) and evaporated to dryness in vacuo to afford the title compound as a damp pale orange solid, 928 g.

m/z: 303 (MH+). δ$_H$ (300 MHz, CDCl$_3$): 10.1 (1H, s), 8.32 (2H, d), 8.05 (2H, d), 4.70 (2H, t), 4.1 (2H, q), 2.40 (2H, t), 2.15 (2H, m), 1.72 (2H, m), 1.22 (3H, t).

Preparation 44

3-Bromo-(trimethylsilyloxy)benzene

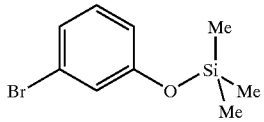

To a stirred solution of 3-bromophenol (382.3 g) in acetonitrile (1725 ml) under nitrogen was added hexamethyldisilazane (235.6 g) over 20 minutes. Chlorotrimethylsilane was added dropwise to the clear solution over 20 minutes with stirring and the resulting white suspension was stirred at room temperature overnight. The slurry was removed by filtration and was washed with acetonitrile (200 ml). The filtrate was evaporated in vacuo to a pale yellow oil which was distilled under vacuum (72° C. at 0.5 mmHg) to give the title compound, 541 g, as a colourless oil.

δ$_H$ (300 MHz, CDCl$_3$): 7.10 (2H, m), 7.04 (1H, m), 6.80 (1H, m), 0.3 (9H, s).

Preparation 45

4-(4,5-Dihydro-4,4-dimethyl-2-oxazolyl)-benzaldehyde

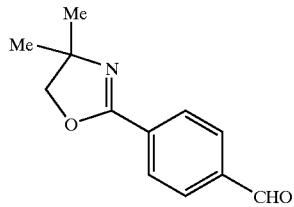

n-Butyl lithium (9.44 ml, 2.5N solution in hexanes) was added to a solution of 2-(4-bromophenyl)-4,5-dihydro-4,4-dimethyl-oxazole [A. I. Meyers et al., J.O.C., 1974, 39, 2787] (5 g) in tetrahydrofuran (80 ml) at −78° C. The reddish solution was stirred at −78° C. for 15 minutes before dimethylformamide (2.3 g) was added dropwise. The resulting deep red solution was allowed to warm to room temperature, quenched with ammonium chloride solution and extracted into ether. The combined extracts were washed with brine, dried (sodium sulphate) and evaporated to dryness in vacuo. The residue was purified by column chromatography (30% ethyl acetate/hexane) to afford the title compound as a colourless liquid, 3.01 g.

m/z: 204 (MH+). δ$_H$ (300MHz, CDCl$_3$): 10.04 (1H, s), 8.10 (2H, d), 7.88 (2H, d), 4.12 (2H, s),1.38 (6H, s).

Preparation 46

4-[(R)-α-(2(S),5(R)-4-Allyl-2.5-dimethyl-1-piperazinyl)-3-(2.5-dimethylpyrrol-1-yl)benzyl]benzonitrile

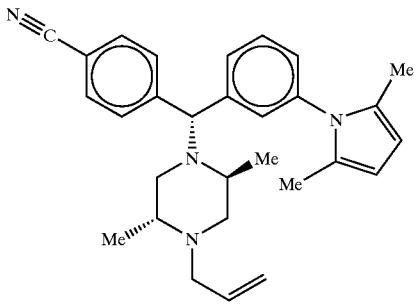

The title compound was prepared in a similar manner to Preparation 5 using the same starting materials except that the 3-(2,5-dimethylpyrrol-1-yl)phenylmagnesium bromide was used.

m/z: 439(MH$^+$). δ$_H$(300 MH, d$_6$-DMSO): 7.76 (2H, d), 7.58 (2H, d), 7.50 (1H, t), 7.32 (1H, d), 7.18 (1H, d), 702 (1H, d), 5.84–5.70 (3H, m), 5.32 (1H, s), 5.14 (1H, d), 5.08 (1H, d), 3.30 (1H, s), 3.18 (1H, m), 2.84 (1H, dd), 2.66 (1H, d), 2.60–2.42 (2H, m), 2.10 (1H, dd), 1.92 (6H, s), 1.72 (1H, m), 1.10 (3H, d), 0.92 (3H, d).

Preparation 47

4-[(R)-α-(2(S),5(R)-4-Allyl-2.5-dimethyl-1-piperazinyl)-3-(2.5-dimethylpyrrol-1-yl)benzyl]phenyltetrazole

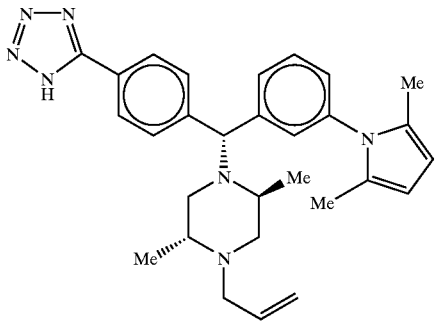

The title compound was prepared in a similar manner to the method of Example 52 using the compound of Preparation 46.

m/z: 482 (MH$^+$). δ$_H$ (300 MHz, d$_6$-DMSO): 7.94 (2H, d), 7.60–7.44 (3H, m), 7.40 (1H, d), 7.20 (1H, d), 7.08 (1H, s), 5.82 (1H, m), 5.76 (2H, s), 5.36–5.18 (3H, m), 3.36 (1H, dd), 3.10 (1H, m), 2.90 (1H, d), 2.80 (1H, m), 2.72 (1H, d), 2.62 (1H, d), 2.36 (1H, m), 2.00–1.90 (8H, m), 1.18 (3H, d), 1.02 (3H, d).

Preparation 48

4-[(R)-α-(2(S),5(R)-4-Allyl-2.5-dimethyl-1-piperazinyl)-3-aminobenzyl]phenyltetrazole

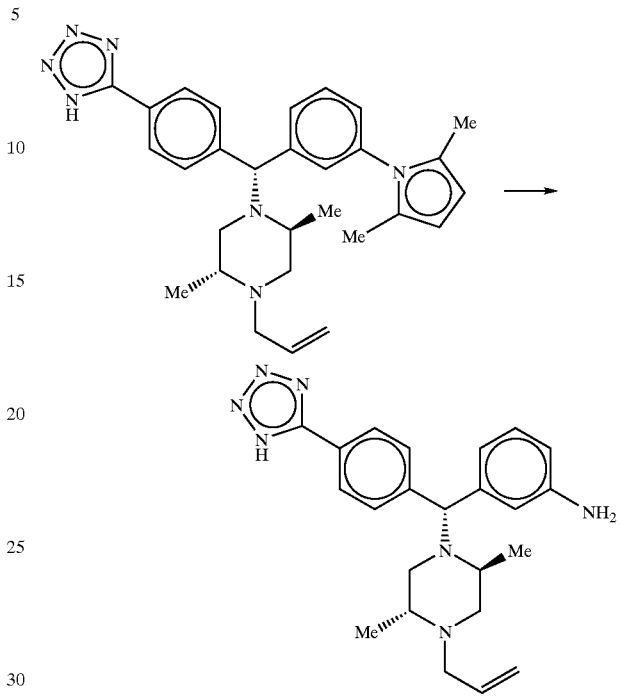

A mixture of the dimethylpyrrole starting material from Preparation 47, (170 mg; 0.00035 mole) and hydroxylamine hydrochloride (74 mgs; 0.00105 mole) in ethanol (3 ml) was heated at reflux for three days. The solvent was removed by rotary evaporation. The brown residue was then flash chromatographed on silica; eluant 90/10/1→85/15/2→80/20/3 CH$_2$Cl$_2$/MeOH/NH$_4$OH to give 54 mg (38%) of the desired product.

m/z: 404 (MH$^+$). δ$_H$ (300 mhz, DMSO-d$_6$): 7.92 (2H, d); 7.50 (2H, d); 6.97 (1H, t), 6.45 (3H, m); 5.80 (1H, m); 5.25 (2H, m); 4.92 (1H, bs); 2.55→3.50 (7H, m); 2.20→2.40 (2H, m); 1.95 (2H, m); 1.00 (6H, 2×d).

Preparation 49

(±)-4-Cyano-[(R,S)-α-(4-allyl-1-piperazinyl)-3-tert-butyldimethylsilyloxybenzyl]benzene

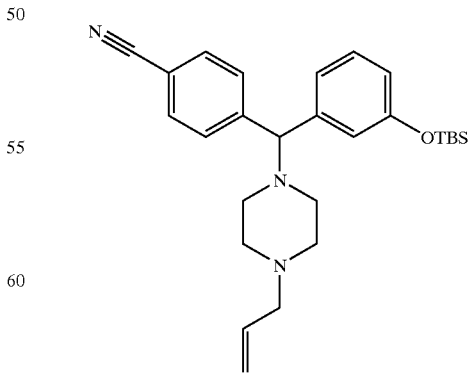

A solution of 1-allyl piperazine (12.9 g), benzotriazole (11.9 g) and 4-cyanobenzaldehyde (13.1 g) in toluene (350 ml) was heated under reflux with azeotropic removal of water for an hour. The solution was allowed to cool to room temperature, and then added to a cooled solution (−10° C.) of 3-tert-butyldimethylsilyloxyphenylmagnesium bromide (prepared from 57.2 g of the corresponding bromide and 4.86 g of magnesium turnings) in tetrahydrofuran (350 ml), at such a rate that the internal temperature did not exceed 0° C. The resulting solution was stirred at 0° C. for 15 minutes, followed by 30 minutes at room temperature. Aqueous saturated ammonium chloride solution was then carefully added, the phases separated and the aqueous layer extracted with diethyl ether (2×500 ml), The combined organic extracts were dried ($Na_2SO_4$) and evaporated to dryness in vacuo to give a brown oil. The residue was purified by column chromatography over silica gel (95/5/0.25 hexane/isopropanol/ammonium hydroxide) to afford the title compound (40 g).

m/z: 447 ($M^+$). $R_f$: 0.46 (90/10/0.75 hexane/isopropanol/ammonium hydroxide). $\delta_H$ (400 MHz, $CDCl_3$): 7.49–7.65 (4H, m), 7.12 (1H, dd), 6.82(1H, d), 6.84 (1H, s), 6.68 (1H, d), 5.84 (1H, m), 5.15 (2H, m), 4.20 (1H, s), 3.00 (2H, d), 2.44 (8H, m), 0.9 (9H, s), 0.15 (6HK s).

Preparation 50

(±)-[(R,S)-α-(4Allyl-1-piperazinyl)-3-tert-butyldimethylsilyl]oxybenzyl)phenyltetrazole

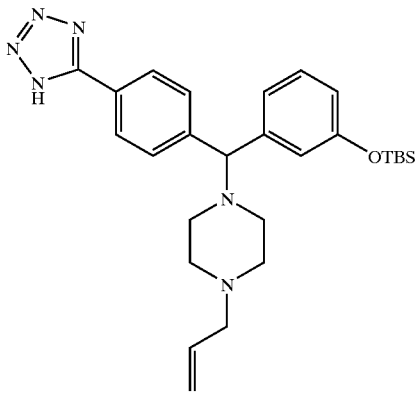

A solution of the compound of Preparation 49 (11 g), dibutyl tin oxide (2.86 g) and trimethylsilyl azide (9.22 g) in toluene (100 ml) were heated together under reflux for 48 hours. On cooling, the reaction mixture was partitioned between ammonium hydroxide solution and ethyl acetate. The phases were separated, and the aqueous layer, extracted with further ethyl acetate (2×200 ml). The combined organic extracts were dried ($Na_2SO_4$) and evaporated to dryness in vacuo. The residue was purified by column chromatography over silica gel using gradient elution (90/1012–85/15/2.5 dichloromethane/methanollammonium hydroxide) to afford the title compound.

m/z: 491 ($MH^+$). $R_f$: 0.35 (80/20/3 dichloromethane/methanol/ammonium hydroxide). $\delta_H$ (400 MHz, DMSO-$d_6$): 7.90 (2H, d), 7.50 (2H, d), 7.12 (1H, m), 6.87 (1H, d), 6.90 (1H, s), 6.63 (1H, d), 5.77 (1H, m), 5.20 (2H, m), 4.34 (1H, s), 3.16 (2H, d), 2.61 (4H, m), 2.36 (4H, m), 0.88 (9H, s), 0.11 (6H, s).

Preparation 51

(±)-Ethyl 4-(5-{4-[(R,S)-α-(4-Allyl-1-piperazinyl)-3-tert-butyldimethylsilyloxybenzyl]phenyl}-1-tetrazolyl)butyrate and (±)-Ethyl 4-(5-{4-[(R,S)-α-(4-Allyl-1-piperazinyl)3-tert-butyldimethylsilyloxybenzyl]phenyl}-2-tetrazolyl)butyrate

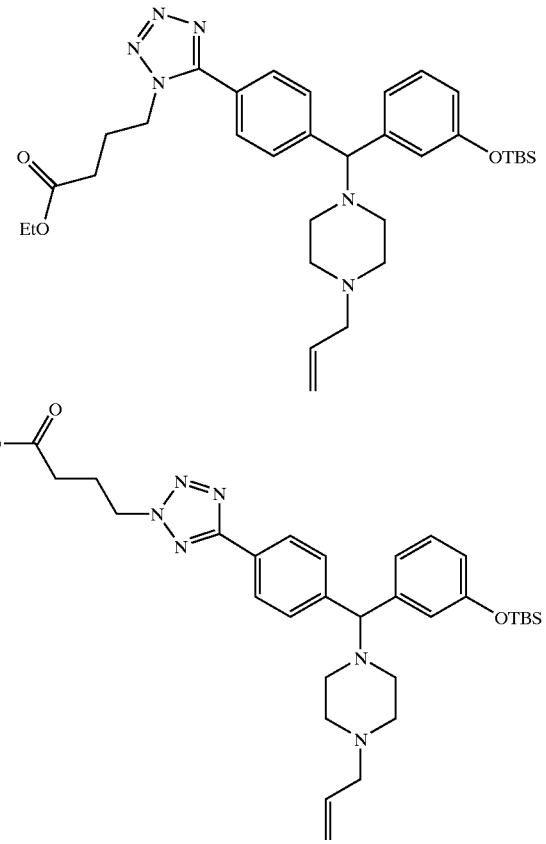

A suspension of the compound of Preparation 50 (1 g) and bis(tri-n-butyltin) oxide (596 mg) in ethanol (5 ml), was stirred under reflux for 2 hours. On cooling, the reaction mixture was evaporated to dryness in vacuo to afford a brown oil. This material was then heated under reflux in ethyl 4-bromobutyrate (16 ml) for 90 minutes and on cooling the mixture was evaporated to dryness in vacuo. The residue was purified by column chromatography over silica gel using gradient elution (50/50–100/0 ethyl acetate/hexane) to afford the N2 isomer, 550 mg.

m/z: 605 ($MH^+$). $R_f$: 0.19 (50150 ethyl acetate/hexane). $\delta_H$ (300 MHz, DMSO-$d_6$): 7.95 (2H, d), 7.56 (2H, d), 7.14 (1H, dd), 6.99 (1H, d), 6.93 (1H, s), 6.64 (1H, d), 5.76 (1H, m), 5.10 (2H, m), 4.72 (2H, t), 4.32 (1H, s), 4.00 (2H, q), 2.92 (2H, d), 2.37 (10H, m), 2.19 (2H, m), 1.14 (3H, t), 0.88 (9H, s), 0.15 (6H, s).

and the N1 isomer, 200 mg. m/z: 605 ($MH^+$). $R_f$: 0.06 (50/50 ethyl acetate/hexane). $\delta_H$ (300 MHz, DMSO-$d_6$): 7.72 (2H, d), 7.61 (2H d), 7.16 (1H, dd), 7.00 (1H, d), 6.84 (1H, s), 6.66 (1H, d), 5.78 (1H, m), 5.12 (2H, m), 4.47 (2H, t), 4.38 (1H, s), 3.82 (2H, q), 2.93 (2H, d), 2.34 (10H, m), 2.03 (2H, m), 1.08 (3H, t), 0.90 (9H, s), 0.14 (6H, s).

Preparation 52

(±)-4-Bromo-α-(3-methoxybenzene)benzyl Alcohol

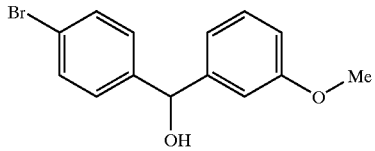

A solution of n-butyl lithium in tetrahydrofuran (10.8 ml, 2.5M), was added dropwise to a cooled solution (−78° C.) of 3-bromoanisole (50.5 g) in tetrahydrofuran (200 ml), and the resulting suspension stirred at −78° C. under a nitrogen atmosphere for an hour. This suspension was then cannulated into a cooled solution (−78° C.) of 4-bromobenzaldehyde (50 g) in tetrahydrofuran (200 ml) and the reaction maintained at this temperature for 3 hours. Saturated aqueous ammonium chloride solution was added and the mixture allowed to warm to room temperature. The layers were separated, and the aqueous phase extracted with diethyl ether. The combined organic extracts were washed with water, and evaporated to dryness in vacuo. The residue was suspended between diethyl ether (200 ml) and saturated aqueous sodium metabisulphite solution (200 ml) and the mixture filtered to remove the resulting white precipitate. The filtrate was separated and the organic layer dried (MgSO$_4$), and evaporated to dryness in vacuo, to give a yellow oil. This was triturated with pentane, to afford the title compound as a yellow crystalline solid, 42 g.

m/z: 293 (MH$^+$). $\delta_H$ (300 MHz, CDCl$_3$): 7.46 (2H, d), 7.26 (3H, m), 6.90 (2H, m), 6.81 (1H, d), 5.76 (1H, s), 3.80 (3H, s), 2.25 (1H, s).

Preparation 53

(±)-4-Bromo-α-(3-methoxybenzene)benzyl Chloride

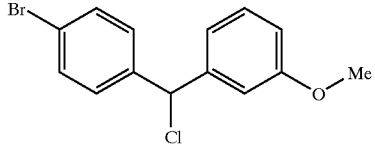

A solution of thionyl chloride (21 mim) in dichioromethane (80 ml) was added dropwise to an ice-cooled solution of the compound of Preparation 52 (42 g) in dichioromethane (400 ml), and the reaction stirred at room temperature for 90 minutes. The mixture was then evaporated to dryness in vacuo, and azeotroped with toluene, to afford the title compound as a brown solid, 45 g.

$\delta_H$ (300 MHz, CDCl$_3$): 7.48 (2H d), 7.29 (3H, m), 6.95 (2H, m), 6.84 (1H, d), 6.03 (1H, s), 3 80 (3H, s).

Preparation 54

(±)-4-Bromo-[(R,S)-α-(4-allyl-1-piperazinyl)-3-methoxybenzl]benzene

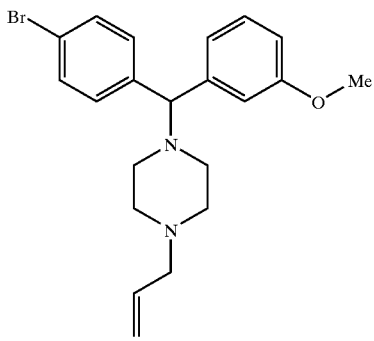

A suspension of 1-allyl piperazine (2.65 g), the compound of preparation 53 (7.85 g) and potassium carbonate (14.5 g) in acetonitrile (50 ml) was heated under a nitrogen atmosphere under reflux for 18 hours. On cooling, diethyl ether was added and the mixture filtered to remove residual solids. The filtrate was washed with water, then brine and the product extracted using 2N aqueous hydrochloric acid solution (4×25 ml). This aqueous solution was then basified with 5N aqueous sodium hydroxide solution and extracted with diethyl ether (3×50 ml). These combined organic extracts were dried (Na$_2$SO$_4$) and evaporated to dryness in vacuo to give the title compound as a brown gum, 7.0 g.

m/z: 401 (M$^-$). $\delta_H$ (300 MHz, CDCl$_3$): 7.38 (2H, d), 7.28 (2H, d), 7.16 (1H, dd), 6.94 (2H, m), 6.71 (1H, d), 5.85 (1H, m), 5.14 (2H, m), 4.17 (1H, s), 3.76 (3H, s), 3.00 (2H, d), 2.44 (8H, m).

Preparation 55

(±)-4-[(R,S)-α-(4-Allyl-1-piperazinyl)-3-methoxybenzyl]benzoic Acid

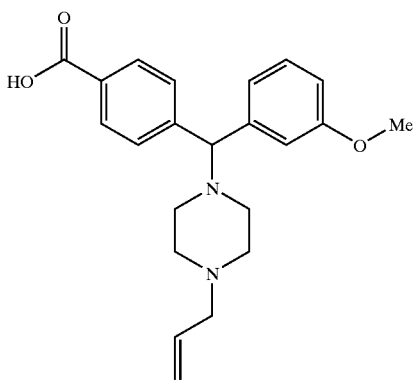

A solution of n-butyl lithium in tetrahydrofuran (1.15 ml, 2.5M) was added dropwise to a cooled (−78° C.) solution of the compound of Preparation 54 (968 mg) in tetrahydrofuran (10 ml), and the resulting orange solution stirred for 15 minutes. Carbon dioxide was bubbled through the reaction mixture and it was then allowed to warm to room temperature and stirring continued under a nitrogen atmosphere for 72 hours. 2N aqueous hydrochloric acid was added, and the resulting mixture basified with ammonium hydroxide solution and evaporated to dryness in vacuo. The residue was purified by column chromatography over silica gel (80120/3 dichloromethane/methanol/ammonium hydroxide) to afford the title compound as a white powder, 470 mg.

m/z: 367 (MH+). $\delta_H$ (300 MHz, CDCl$_3$): 7.88 (2H, d), 7.39 (2H, d), 7.09 (1H, dd), 6.88 (2H, m), 6.64 (1H, d), 5.90 (1H, m), 5.10 (3H, m), 4.20 (1H, s), 3.70 (3H, s), 3.00 (2H, d), 2.50 (4H, m), 2.40 (4H, m).

Preparation 56

Ethyl 5-Aminoyalerate Hydrochloride

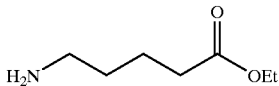

Hydrogen chloride gas was bubbled through a suspension of 5-aminovaleric acid (12 g) in ethanol (100 ml) and the reaction stirred under reflux for 90 minutes. On cooling, the mixture was evaporated to dryness in vacuo, to give an off-white solid. This material was recrystallised from ethanol/diethyl ether to afford the title compound, 15.1 g.

m/z: 145 (M+). $\delta_H$ (300 MHz, CDCl$_3$): 8.25 (2H, br.s), 4.12 (2H, t), 3.06 (2H, m), 2.36 (2H, t), 1.79 (4H, m), 1.23 (3H, t).

Preparation 57

(±)-Ethyl 5-{4-[(R,S)-(4-allyl-1-piperazinyl)-1-(3-methoxyphenyl)methyl]phenylcarboxamido}valerate

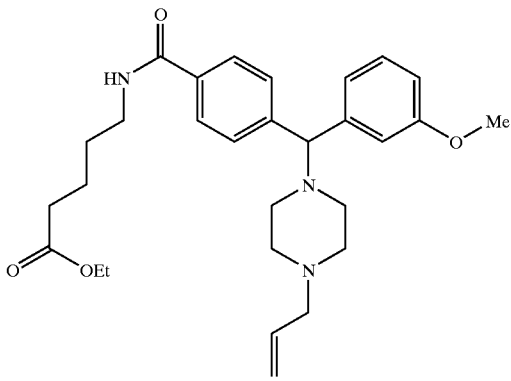

A solution of the compound of Preparation 55 (470 mg), diisopropylamine (492 μl), 1-(3-dimethylaminopropyl)-3-ethylcarbodiimide hydrochloride (295 mg), 1-hydroxybenzotriazole (312 mg) and the compound of Preparation 56 (280 mg) in dry dichloromethane (20 ml), was stirred under a nitrogen atmosphere, at room temperature for 18 hours. Water (20 ml) was added and the mixture extracted with dichloromethane (2×25 ml). The combined organic extracts were dried (Na$_2$SO$_4$) and evaporated to dryness in vacuo. The residue was purified by column chromatography over silica gel (95/5/0.5 dichloromethane/methanol/ammonium hydroxide) to afford the title compound as an oil, 590 mg.

m/z: 494 (MH+). R$_f$: 0.47 (95/5/0.5 dichloromethane/methanol/ammonium hydroxide). $\delta_H$ (300 MHz, CDCl$_3$): 7.67 (2H, d), 7.50 (2H, d), 7.19 (1H, dd), 6.98 (2 H, m), 6.72 (1H, d), 5.85 (1H, m), 5.16 (2H, m), 4.22 (1H, s), 4.13 (2H, q), 3.77 (3H, s), 3.44 (2H, m), 3.00 (2H, d), 2.48 (8H, m), 2.36 (2H, t), 1.67 (4H, m), 1.28 (3H, t).

Preparation 58

2-Bromoethoxy Acetonitrile

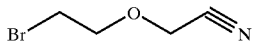

Triphenylphosphine (6.80 g) was added portionwise to an ice-cooled solution of 2-hydroxyethoxyacetonitrile (J.Org.Chem. 20; 1990; 5337) (2.50 g) and carbon tetrabromide (8.62 g) in acetonitrile under a nitrogen atmosphere. The reaction mixture was stirred at room temperature for 18 hours and then evaporated to dryness in vacuo. The residue was triturated with a hexane/dichloromethane solution, the resulting mixture filtered and the filtrate evaporated to dryness in vacuo to give an oil. This material was purified by column chromatography over silica gel using gradient elution (66/34–50150 hexane/dichloromethane) to afford the title compound as a colourless oil, 3.17 g.

m/z: 163 (M+). $\delta_H$ (300 MHz, CDCl$_3$): 4.35 (2H, s), 3.94 (2H, t), 3.51 (2H, t).

Preparation 59

(±)-2-(5-{4-[(RS)-α-(4-Allyl-vinerazinyl)-3-hydroxybenzyl]phenyl}-2-tetrazolyl)ethoxy Acetonitrile

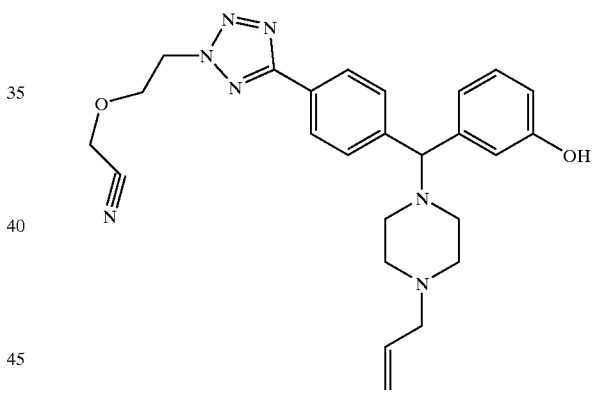

A suspension of the compound of Example 55 (3.9 g), the compound of Preparation 58 (1.26 g) and potassium carbonate (3.3 g) in 2-butanone (120 ml) was heated under reflux for 72 hours. On cooling, water was added and the reaction mtixture extracted with ethyl acetate (3×100 ml). The combined organic extracts were dried (Na$_2$SO$_4$) and evaporated to dryness in vacua. The residue was purified by column chromatography over silica gel using gradient elution (97/3–95/5 dichloromethane/methanol) and then again with (97/3/0–90/10/2 diethyl ether/ethanol/ammonium hydroxide) to afford the title compound, 1.74 g.

mz: 460 (MH+). R$_f$: 0.36 (95/5/0.5 diethyl ether/ethanol/ammonium hydroxide). $\delta_H$ (400 MHz, CDCl$_3$): 8.06 (2H, d), 7.54 (2H, d), 7.15 (1H, dd), 6.98 (1H, d), 6.91 (1H, s), 6.66 (1H, d), 5.88 (1H, m), 5.32 (1H, s), 5.17 (2H, m), 4.88 (2H, t), 4.22 (5H, m), 3.04 (2H, d), 2.51 (8H, m). Found: C, 64.68; H, 6.33; N, 21.07. C$_{25}$H$_{29}$N$_2$O$_2$.1/5H$_2$O requires C, 64.83; H, 6.40; N, 21.17%. The N1 isomer was also isolated, 160 mg.

Preparation 60

2-(5-{4-(±)-[(R,S)-α-(4-Benzyl-1-piperazinyl)-3-hydroxybenzyl]phenyl}-1-tetrazolyl)ethoxyacetonitrile and 2-(5-{4-(±)-[(R,S)-α-(4-Benzyl-1-piperazinyl)-3-hydroxybenzyl]phenyl}-2-tetrazolyl)ethoxyacetonitrile

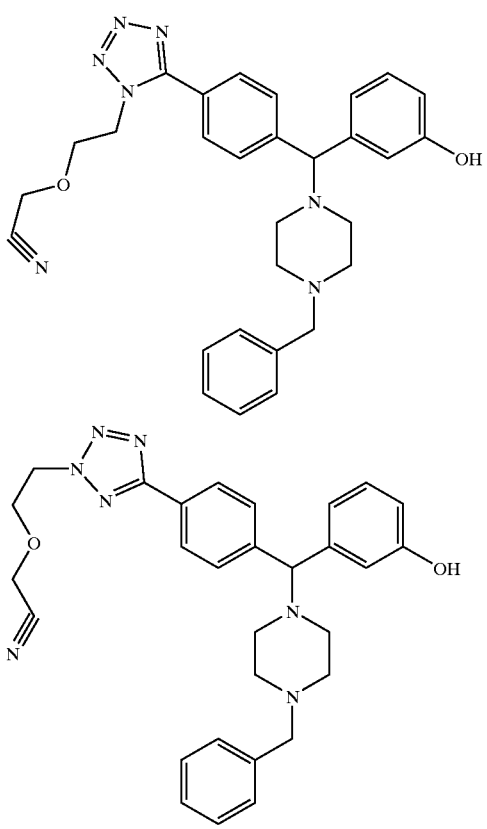

A suspension of the compound of Preparation 4 b (2.16 g), the compound of Preparation 58 (670 mg) and potassium carbonate (1.66 g) in acetonitlile (40 ml), was stirred under reflux for 20 hours. On cooling, the reaction mixture was concentrated in vacuo, and the residue partitioned between ethyl acetate and water. The layers were separated and the aqueous solution extracted with ethyl acetate (2×50 ml). The combined organic extracts were washed with brine, dried ($Na_2SO_4$) and evaporated to dryness in vacuo to give a brown oil. This material was then dissolved in tetrahydrofuran (20 ml), tetraethylammonium fluoride (1.23 g) added and the reaction stirred at room temperature for 18 hours. Water was added and the mixture extracted with ethyl acetate (3×30 ml). The combined organic extracts were washed with brine, dried ($Na_2SO_4$) and evaporated to dryness in vacuo. The residue was purified by column chromatography over silica gel using gradient elution (75/25–65/35 hexane/ethyl acetate) and then again with (95/5 dichloromethane/methanol) to afford the N2 isomer, 1.55 g.

m/z: 510 (MH$^+$). $\delta_H$ (400 MHz, DMSO-d$_6$): 9.34 (1H, s), 7.98 (2H, d), 7.57 (2H, d), 7.26 (5H, m), 7.08 (1H, dd), 6.83 (2H, m), 6.56 (1H, d), 4.94 (2H, t), 4.48 (2H, s), 4.24 (1H, s), 4.10 (2H, t), 3.44 (2H, s), 2.22–2.48 (8H, m).

and the N1 isomer, 180 mg. m/z: 510(MH$^+$). $\delta_H$ (400MHz, DMSO-d$_6$): 9.36 (1H, s), 7.72 (2H, d), 7.61 (2H, d), 7.26 (5H, m), 7.08 (1H, dd), 6.83 (2H, m), 6.57 (1H, d), 4.65 (2H, t), 4.40 (2H, s), 4.30 (1H, s), 3.98 (2H, t), 3.47 (2H, s), 2.30–2.62 (8H, m).

Preparation 61

Ethyl 5-(4-[(R)-1-[(2S,5R)-2,5-Dimethyl-1-piperazinyl]-1-(3-methoxythenyl)methyl]phenylcarboxamido)valerate

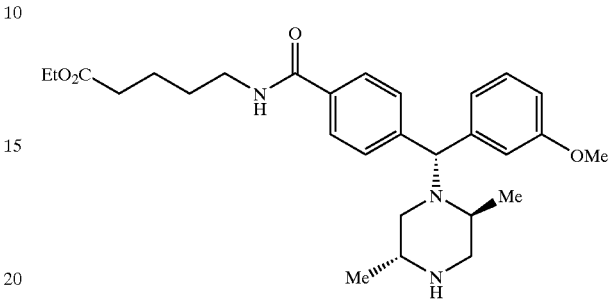

Tris(triphenylphosphine)rhodium(I) chloride (1.0 g) was added to a solution of the compound of Preparation 36 (8.12 g) in acetonitrile (160 ml) and water (40 ml). The reaction mixture was heated under a gentle reflux and the solvent allowed to distil off slowly. Additional acetonitrile/water (100 ml; 4:1 v/v) was added at such a rate as to maintain a steady distillation. After the addition of solvent was complete the distillation was continued until the volume was reduced to approximately 60 ml. The cooled solution was poured into ethyl acetate and washed with saturated aqueous sodium bicarbonate solution and saturated brine. The solution was dried (magnesium sulphate), evaporated to dryne,ss in vacuo and the residue was purified by column chromatography over silica gel using gradient elution (100% dichloromethane to 60/40/1 dichloromethane/methanol/amnmonium hydroxide) to afford the title compound, 6.35 g.

m/z: 482(MH$^+$). R$_f$: 0.34 (93/711 dichloromethane/methanol/ammonium hydroxide).

Preparation 62

Ethyl 5-(4-[(R)-1-[(2S,5R)-4-Propyl-2,5-dimethyl-1-piperazinyl]-1-(3-methoxythenyl)methyl]phenylcarboxamido)pentanoate

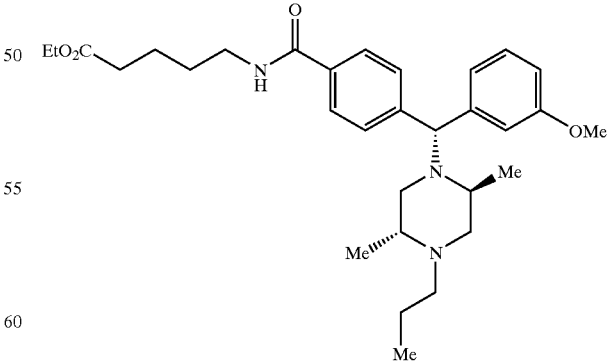

To a solution of the compound of Preparation 61 (600 mg), propionaldehyde (102 μg) and glacial acetic acid (100 mg) in dry tetrahydrofuran (20 ml) was added, with stirring, sodium triacetoxyborohydride (636 mg). The resulting mixture was stirred at room temperature for 18 hours after which time it was poured into ethyl acetate. The organic phase was washed with saturated aqueous sodium hydrogen carbonate solution, saturated brine, dried (magnesium sulphate) and evaporated to dryness in vacuo. The residue was purified by column chromatography over silica gel using gradient elution (100% dichloromethane to 95/5 dichloromethane/methanol) to afford the title compound, 611 mg.

m/z: 524 (MH+). $R_f$: 62 (93/741 dichloromethane/methanol/ammonium hydroxide).

Preparations 63 to 65

The following compounds of the general formula:

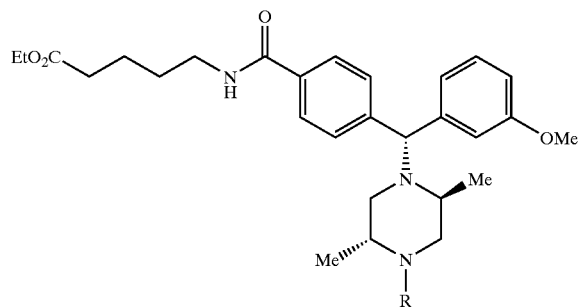

were prepared from the compound of Preparation 61 by reductive alkylation with the appropriate aldehyde using a similar method to that described in Preparation 62.

| Preparation number | R | $R_f$ | m/z (MH+) |
|---|---|---|---|
| 63 | *~~Me | 0.64 | 538 |
| 64 | *~△ | 0.70 | 538 |
| 65 | *~CH(Me)Me | 0.76 | 536 |

Preparation 63: Ethyl 5-(4-[(R)-1-[(2S,5R)-4-butyl-2,5-dimethyl-1-piperazinyl]-1-(3-methoxyphenyl)methyl]phenylcarboxamido)pentanoate Preparation 64: Ethyl 5-(4-[(R)-1-[(2S,5R)-4-cyclopropylmethyl-2,5-dimethyl-1-piperazinyl]-1-(3-methoxyphenyl)methyl]phenylcarboxamido)pentanoate Preparation 65: Ethyl 5-(4-[(R)-1-[(2S,5R)-4-iso-butyl-2,5-dimethyl-1-piperazinyl]-1-(3-methoxyphenyl)methyl]phenylcarboxamido)pentanoate Preparation 66

(3S)-1-Benzyl-3-methylpiperazine

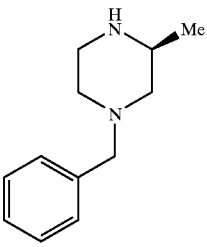

(S)-(+)-2-Methylpiperazine (2.63 g), benzylbromide (3.12 ml) and potassium carbonate (5.4 g) were heated together in acetonitrile (120 ml) at 40° C. for 3 days. The mixture was evaporated to dryness in vacuo and the residue partitioned between aqueous sodium bicarbonate solution and ethyl acetate. The organic phase was separated, dried (magnesium sulphate) and evaporated to dryness in vacuo. The residue was purified by column chromatography over silica gel using gradient elution (95/510 to 92/7/1 dichloromethane/methanol/ammonium hydroxide) to afford the title compound as a solid, 1.12 g.

$R_f$: 0.25 (92/7/1; dichloromethane/methanol/ammonium hydroxide). $\delta_H$ (300 MHz, CDCl$_3$): 7.3 (5H, m), 3.5 (2H, s), 2.9 (3H, m), 2.77 (2H, m), 2.02 (1H, m), 1.65 (2H, m), 1.02 (3H, m).

Preparations 67 and 68

Methyl 3-[5-(4-Formylphenyl)-2H-1,2,3,4-tetrazolyl-2-yl]methylbenzoate and

Methyl 3-[5-(4-Formylphenyl)-1H-1,2,3,4-tetrazolyl-2-yl]methylbenzoate

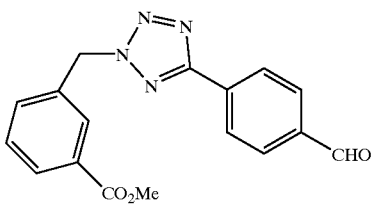

and

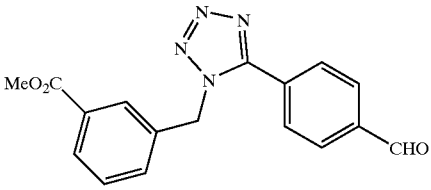

A mixture of the compound of Preparation 42 (3 g), potassium carbonate (7.2 g) and methyl 2-bromomethylbenzoate (4.35 g) in dry acetonitrile (75 ml) was heated together under reflux for 5 hours. The reaction mixture was cooled to room temperature and evaporated to dryness in vacuo. The residue was partitioned between water and ethyl acetate, and the organic layer separated, dried (sodium sulphate) and evaporated in vacuo. The residue was purified by column chromatography over silica gel using gradient elution (80/20 to 50/50 hexane/ethyl acetate) to afford the title compounds.

The N-2 isomer eluted first (2.92 g).

m/z: 323 (MH+). mp: 113–114° C. $\delta_H$ (400 MHz, CDCl$_3$): 10.08 (1H, s), 8.35 (2H, d), 8.15 (1H, s), 8.08 (1H, d), 8.00 (2H, d), 7.63 (1H, d), 7.49 (1H, t), 5.88 (2H, s), 3.95 (3H, s). Found: C, 63.29; H, 4.33; N, 17.19. C$_{17}$H$_{14}$N$_4$O$_3$ requires C, 63.35; H, 4.38; N, 17.3%.

followed by the N-1 isomer (212 mg).

m/z: 323 (MH+). $\delta_H$ (400 MHz, CDCl$_3$): 10.12 (1H, s), 8.04 (3H, m), 7.83 (1H, s), 7.78 (2H, d), 7.47 (1H, t), 7.35 (1H, d), 5.71 (2H, s), 3.92 (3H, s).

Preparation 69

Ethyl 3-[5-(4-Formylphenyl)-2H-1,2,3,4-tetrazolyl-2-yl]propionate

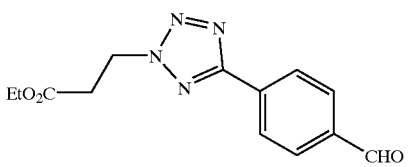

A mixture of the compound of Preparation 42 (3 g), potassium carbonate (8.3 g) and ethyl 3-bromopropionate (4.68 g) in dry acetonitrile (70 ml) was heated together at 50° C. for 16 hours. The reaction mixture was cooled to room temperature and evaporated to dryness in vacuo. The residue was partitioned between water and ethyl acetate, and the organic layer separated, dried (sodium sulphate) and evaporated in vacuo. The crude residue containing both N-1 and N-2 isomers was purified by column chromatography over silica gel (½ pentane/ethyl acetate) to afford the title compound as a colourless oil, 1 g.

$\delta_H$ (300 MHz, CDCl$_3$): 10.1 (1H, s), 8.35 (2H, d), 8.00 (2H, d), 4.98 (2H, t), 4.20 (2H, q), 3.16 (2H, t), 1.15 (3H, t).

Preparations 70 and 71

Ethyl 4-[5-(4-Formylphenyl)-2H-1,2,3,4-tetrazolyl-2-yl]butanoate and

Ethyl 4-[5-(4-Formylphenyl)-1H-1,2,3,4-tetrazolyl-2-yl]butanoate

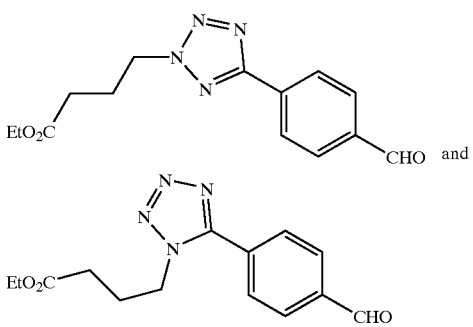

A mixture of the compound of Preparation 42 (3 g), potassium carbonate (5.9 g) and methyl 4-bromobutanoate (4.68 g) in dry acetonitrile (70 ml) was heated together at 50° C. for 16 hours. The reaction mixture was cooled to room temperature and evaporated to dryness in vacuo. The residue was partitioned between water and ethyl acetate, and the organic layer separated, dried (sodium sulphate) and evaporated in vacuo. The crude residue containing both N-1 and N-2 isomers was purified by column chromatography over silica gel (½ pentane/ethyl acetate) to afford the title compounds as a colourless oils. The N-2 isomer eluted first (3.9 g): R$_f$: 0.5 (1:2; ethyl acetate/pentane). $\delta_H$ (300MHz, CDCl$_3$): 10.1 (1H s), 8.33 (2H, d), 8.01 (2H, d), 4.79 (2H, t), 3.70 (3H, s), 2.50–2.35 (4H, m).

Followed by the N-1 isomer (0.35 g). R$_f$: 0.1 (1:2; ethyl acetate/pentane). $\delta_H$ (300 MHz, CDCl$_3$): 10.13 (1H, s), 8.10 (2H, d), 7.95 (2H, d), 4.58 (2H, t), 3.63 (3H, s), 2.42 (2H, t), 2.28 (2H, m).

What is claimed is:

1. A compound of the formula:

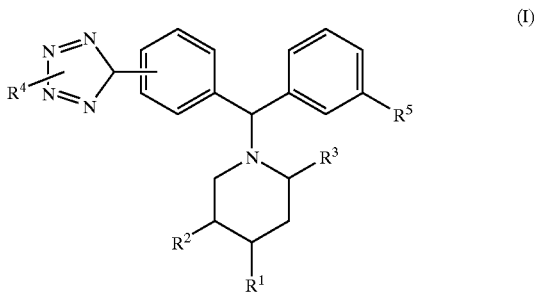

(I)

or a pharmaceutically acceptable salt thereof, wherein

R$^1$ is H, C$_2$–C$_6$ alkanoyl, C$_1$–C$_6$ alkyl, C$_2$–C$_6$ alkenyl, C$_2$–C$_6$ alkynyl, C$_3$–C$_7$ cycloalkyl, (C$_3$–C$_7$ cycloalkyl)-(C$_1$–C$_4$ alkyl), (C$_1$–C$_4$ alkoxy)-(C$_1$–C$_4$ alkyl), carboxy-(C$_1$–C$_4$ alkyl), aryl-(C$_1$–C$_4$ alkyl) or heteroaryl-(C$_1$–C$_4$ alkyl);

R$^2$ and R$^3$ are each independently H or C$_1$–C$_4$ alkyl;

R$^4$ is selected from (i) H (ii) a group of the formula R$^6$—(CH$_2$)$_m$—Z—(CH$_2$)$_n$—, where m is 0, 1, 2 or 3, n is 1, 2 or 3, Z is a direct link or O, and R$^6$ is —CO$_2$H or —CO$_2$(C$_1$–C$_4$ alkyl), or (iii) a group of the formula

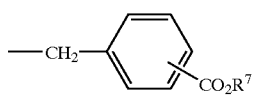

where R$^7$ is H or C$_1$–C$_4$ alkyl;

and R$^5$ is hydroxy, C$_1$–C$_4$ alkoxy or —NHSO$_2$(C$_1$–C$_4$ alkyl);

with the proviso that when Z is O, m is 1, 2 or 3 and n is 2 or 3;

and wherein (a) "aryl" is phenyl or naphthyl, both optionally substituted by up to three substituents each independently selected from halo, trifluoromethyl, C$_1$–C$_4$ alkyl and C$_1$–C$_4$ alkoxy, and (b) "heteroaryl" is thiazolyl, oxazolyl, oxadiazolyl, thiadiazolyl, pyridinyl, pyrimidinyl or pyrazolyl.

2. A compound of claim 1, wherein aryl is phenyl optionally substituted by one or two substituents each independently selected from halo, trifluoromethyl, C$_1$–C$_4$ alkyl and C$_1$–C$_4$ alkoxy.

3. A compound of claim 2, wherein R$^1$ is H, allyl, benzyl, C$_1$–C$_4$ alkyl or (C$_3$–C$_7$ cycloalkyl)methyl.

4. A compound of claim 3, wherein R$^1$ is allyl.

5. A compound of claim 4 where R$^2$ and R$^3$ are each independently H or CH$_3$.

6. A compound of claim 5, wherein R$^2$ and R$^3$ are either both H or both methyl.

7. A compound of claim 6, wherein R$^2$ and R$^3$ are both methyl.

8. A compound of claim 7, wherein $R^5$ is hydroxy, methoxy or —$NHSO_2Me$.

9. A compound of claim 8, wherein $R^5$ is hydroxy.

10. A compound of claim 9 wherein $R^4$ is H or a group of the formula (a) —$(CH_2)_pCO_2H$ or —$(CH_2)_pCO_2(C_1-C_4$ alkyl) wherein p is 1, 2, 3 or 4 (b) —$(CH_2)_2$—O—$CH_2CO_2H$ (c) —$(CH_2)_2$—O—$CH_2CO_2(C_1-C_4$ alkyl) or (d)

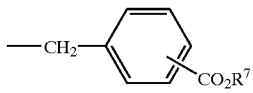

where $R^7$ is H or $C_1-C_4$ alkyl.

11. A compound of claim 10 which has the stereochemistry:

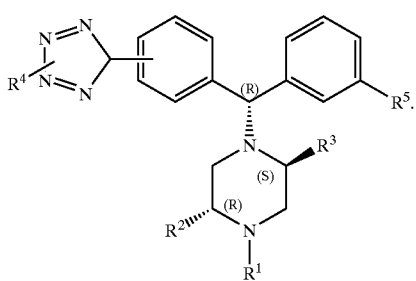

(IA)

12. A compound of claim 11 in which the tetrazole ring is attached to the 3- or 4-position of the adjacent phenyl ring.

13. A compound of the formula (I) which is:

(+)-5-{4-[(R)-α-(2S),5(R)-4-allyl-2,5-dimethyl-1-piperazinyl-3-hydroxybenzyl]phenyl}-1H-tetrazole;

(−)-5-{4-[(R)-α-(2S),5(R)-4-benzyl-2,5-dimethyl-1-piperazinyl)-3-hydroxybenzyl]phenyl}-1H-tetrazole;

3-(5-{4-[(R)-α-(2S),5(R)-4-allyl-2,5-dimethyl-1-piperazinyl)-3-hydroxybenzyl]phenyl}-2-tetrazolyl) propionic acid;

(+)-5-(5-{4-[{R}-α-(2S), 5(R)-4-allyl-2,5-dimethyl-1-piperazinyl)-3-hydroxybenzyl]phenyl}-1-tetrazolylvaleric acid;

(+)-5-(5-{4-[(R)-α-(2S), 5(R)-4-allyl-2,5-dimethyl-1-piperazinyl)-3-hydroxybenzyl]phenyl}-2-tetrazolylvaleric acid;

(5-{4-[(R)-α-(2S),5(R)-4-benzyl-2,5-dimethyl-1-piperazinyl)-3-hydroxybenzyl]phenyl}-2-tetrazolyl)-4-methylbenzoic acid;

(5-{4-[(R)-α-(2S),5(R)-4-benzyl-2,5-dimethyl-1-piperazinyl)-3-hydroxybenzyl]phenyl}-2-tetrazolyl)-4-methylbenzoic acid;

(5-{4-[(R)-α-(2S),5(R)-4-benzyl-2,5-dimethyl-1-piperazinyl)-3-hydroxybenzyl]phenyl}-1-tetrazolyl-4-methylbenzoic acid;

(5-{4-[(R)-α-(2S),5(R)-4-benzyl-2,5-dimethyl-1-piperazinyl)-3-hydroxybenzyl]phenyl}-2-tetrazolyl)-4-methylbenzoic acid; or (5-{4-[(R)-α-(2S),5(R)-4-benzyl-2,5-dimethyl-1-piperazinyl}-3-hydroxybenzyl]phenyl}-1-tetrazolyl)-3-methylbenzoic acid.

14. A method of treating a gastro-intestinal disorder or a functional GI disorder in a mammal, which comprises administering to said mammal a compound of claim 1 in which $R^4$ is other than H or a pharmaceutically acceptable salt thereof.

15. A method of claim 14 wherein said gastro-intestinal disorder is functional bowel disease.

16. A method of claim 14 wherein said functional GI disorder is irritable bowel syndrome, functional diarhoea, functional distension, functional pain or non-ulcerogenic dyspepsia.

17. A method of claim 16 wherein said functional GI disorder is irritable bowel syndrome.

* * * * *